(12) United States Patent
Melnick et al.

(10) Patent No.: US 9,943,506 B2
(45) Date of Patent: Apr. 17, 2018

(54) BCL6 INHIBITORS AS ANTICANCER AGENTS

(71) Applicants: Cornell University, Ithaca, NY (US); University of Maryland, Baltimore, Baltimore, MD (US)

(72) Inventors: Ari Melnick, New York, NY (US); Leandro Carlos A. Cerchietti, New York, NY (US); Mariano G. Cardenas, New York, NY (US); Fengtian Xue, New York, NY (US); Alexander D. MacKerell, Baltimore, MD (US)

(73) Assignees: Cornell University, Ithaca, NY (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 14/899,083

(22) PCT Filed: Jun. 16, 2014

(86) PCT No.: PCT/US2014/042556
§ 371 (c)(1),
(2) Date: Dec. 16, 2015

(87) PCT Pub. No.: WO2014/204859
PCT Pub. Date: Dec. 24, 2014

(65) Prior Publication Data
US 2016/0166549 A1 Jun. 16, 2016

Related U.S. Application Data

(60) Provisional application No. 61/836,043, filed on Jun. 17, 2013, provisional application No. 61/845,255, filed on Jul. 11, 2013, provisional application No. 61/939,827, filed on Feb. 14, 2014.

(51) Int. Cl.
| | | |
|---|---|---|
| A61K 31/427 | (2006.01) |
| A61K 45/06 | (2006.01) |
| A61K 31/4166 | (2006.01) |
| A61K 31/496 | (2006.01) |
| A61K 31/53 | (2006.01) |

(52) U.S. Cl.
CPC ........ *A61K 31/427* (2013.01); *A61K 31/4166* (2013.01); *A61K 31/496* (2013.01); *A61K 31/53* (2013.01); *A61K 45/06* (2013.01)

(58) Field of Classification Search
CPC .. A61K 31/427; A61K 45/06; A61K 31/4166; A61K 31/496; A61K 31/53

USPC ............................ 514/34, 283, 369; 534/375
See application file for complete search history.

(56) References Cited

U.S. PATENT DOCUMENTS

| 8,338,464 B2 * | 12/2012 | Melnick ............... A61K 31/415 514/360 |
| 2010/0130564 A1 | 5/2010 | Melnick et al. |
| 2012/0014979 A1 | 1/2012 | Dent |

FOREIGN PATENT DOCUMENTS

| WO | WO-2014204859 A2 | 12/2014 |
| WO | WO-2014204859 A3 | 12/2014 |

OTHER PUBLICATIONS

Glossary of medical education terms, Institute of International Medical Education. http://www.iime.org/glossary.htm Accessed in Mar. 2013.*
West et al. New and emerging HDAC inhibitors for cancer treatment. J Clin Invest. 2014;124(1):30-39.*
Furdas et al. Rhodanine carboxylic acids as novel inhibitors of histone acetyltransferases. Med. Chem. Commun., 2012, 3, 305-311.*
"International Application Serial No. PCT/US2014/042556, International Search Report dated Dec. 10, 2014", 5 pgs.
"International Application Serial No. PCT/US2014/042556, Invitation to Pay Additional Fees and Partial Search Report dated Oct. 1, 2014", 2 pgs.
"International Application Serial No. PCT/US2014/042556, Written Opinion dated Dec. 10, 2014", 6 pgs.
Cerchietti, L. C, et al., "A small-molecule inhibitor of BCL6 kills DLBCL cells in vitro and in vivo", Cancer Cell, 17(4), (2010), 400-411.

* cited by examiner

*Primary Examiner* — Yih-Horng Shiao
(74) *Attorney, Agent, or Firm* — Schwegman Lundberg & Woessner, P.A.

(57) ABSTRACT

The invention provides compositions and methods for blocking the BCL6 BTB domain with small molecule, non-peptide compounds as disclosed and claimed herein. BCL6 is a transcriptional repressor of the BTB-POZ (brie a brae, tramtrack, broad complex/pox virus zincfinger) family of proteins. It is required for normal development of germinal center (GC) B-cells and is also the most commonly involvedoncogene in diffuse large B-celllymphomas (DLBCLs), and constitutive expression of BCL6 in GC B-cells causes DLBCL in mice.

7 Claims, 36 Drawing Sheets

| | Bcl6 dependent | | | | Bcl6 independent | | | | | IC50(reporter) |
|---|---|---|---|---|---|---|---|---|---|---|
| | GI 50 (μM) | | | | | | | | | |
| | Ly3 | Ly1 | Ly10 | SUDHL6 | Ly7 | Toledo | K422 | WSUDL CL2 | Ly4 | Ly1850 | |
| 355 | 54 | 37 | 62 | 1 | 45 | 35 | 38 | 52 | 81 | 55 | 361=7 μM |
| 357 | 79 | 81 | 60 | 1 | 25 | 51 | 58 | 100 | >125 | 56 | 362=34 μM |
| 358 | >125 | >125 | >125 | 2 | 20 | 69 | >125 | >125 | >125 | >125 | 363=37 μM |
| 361 | 56 | 24 | 166 | 7 | 26 | 39 | 20 | 41 | 98 | 103 | 364=49 μM |
| | | | | | | | | | | | 365=30 μM |
| | | | | | | | | | | | 366=54 μM |
| | | | | | | | | | | | 367=31 μM |
| | | | | | | | | | | | 369=46 μM |
| | | | | | | | | | | | 370=57 μM |

Fig.6B

IC50(reporter)
396 = 30 µM

| Compound | Kd (µM) | BCL6 independent | BCL6 dependent | |
|---|---|---|---|---|
| | | GI50Toledo (µM) | GI50Ly7 (µM) | GI50SUDHL6 (µM) |
| 397 | 122±10 | >125 | >125 | 55±10 |

Fig. 7B

| | Bcl6 dependent | | | | | Bcl6 independent | | | |
|---|---|---|---|---|---|---|---|---|---|
| | GI 50 (μM) | | | | | | | | |
| | Ly3 | Ly1 | Ly10 | SUDHL6 | Ly7 | Toledo | K422 | WSUDLCL2 | Ly4 | Ly1850 |
| 3055 | 5 | 4 | 68 | 0.2 | 11 | 11 | 2 | 8 | 27 | 13 |
| 3061 | 5 | 2 | >125 | 4 | 1 | 4 | 0.4 | 0.2 | 32 | 0.2 |
| 3063 | >125 | 56 | >125 | 35 | >125 | 50 | >125 | >125 | >125 | >125 |
| 3065 | >125 | >125 | >125 | >125 | >125 | >125 | >125 | >125 | >125 | >125 |

IC50(reporter)
3055 = 4 μM
3061 = 2 μM
3063 = 22 μM
3065 = 24 μM
3079 = 77 μM

*Fig. 9B*

Scaffold 5, SEB1001 analogs

VIII $X_1 = O, S$
$n = 0, 1, 2,$ or $3$
$X_2 =$ halogen, alkyl, alkoxy, $NO_2$, $CF_3$

Example and docking:

5a

| Cmpd | LGFE$_{ave}$ | LGFE$_{low}$ |
|---|---|---|
| 5a | -19.38 | -19.58 |

Scaffold 6, ID 01335 analogs

6

X = S, O, NH
R = alkyl
A ring = substituted phenyl, pyridinyl, and other heterocycles

Example and docking:

6a

| Cmpd | LGFE ave | LGFE low |
|------|----------|----------|
| 6a   | -21.89   | -22.86   |

BCL6 INHIBITORS AS ANTICANCER AGENTS

CROSS-REFERENCE TO RELATED APPLICATIONS

This application is a U.S. National Stage filing under 35 U.S.C. 371 from International Application No. PCT/US2014/042556, filed Jun. 16, 2014, and published as WO 2014/204859 and published on Dec. 24, 2014, which claims the priority of U.S. Ser. Nos. 61/836,043, filed Jun. 17, 2013; 61/845,255, filed Jul. 11, 2013; and 61/939,827, filed Feb. 14, 2014; the disclosures of which are incorporated by reference in their entireties.

BACKGROUND

BCL6 is a transcriptional repressor of the BTB-POZ (bric à brac, tramtrack, broad complex/pox virus zinc finger) family of proteins. It is required for normal development of germinal center (GC) B-cells and is also the most commonly involved oncogene in diffuse large B-cell lymphomas (DLBCLs), and constitutive expression of BCL6 in GC B-cells causes DLBCL in mice. DLBCLs are aggressive tumors that arise from germinal center (GC) B-cells and are the most common form of non-Hodgkin's lymphomas. BCL6 is required for survival of DLBCL cells and can limit their ability to respond to DNA damaging agents. It is also frequently expressed in follicular lymphomas (FLs), and may be required for survival of these tumors as well. DLBCL and FL collectively constitute ~60-70% of B-cell lymphomas and the incidence of these tumors has been rising in recent decades. BLC6 binds to the SMRT co-repressor through a tight and unique interaction mediated by the N-terminal BTB/POZ domain of BCL6. Peptides that mimic the SMRT interface can displace SMRT from BCL6, de-repress BCL6 target genes and kill DLBCL cells. BCL6 has an N-terminal BTB domain that mediates transcriptional repression and a C-terminal C2H2 zinc finger that binds to a specific DNA consensus sequence. The two regions are linked by a second repression domain (RD2) that also has repressor activity. The BTB domain of BCL6 recruits the SMRT, N-CoR, and BCoR corepressors. The minimal binding domain of the SMRT, N-CoR, and BCoR corepressors maps to a conserved 17 amino acid sequence (BBD, BCL6 Binding Domain) that binds to a "lateral groove" motif on the BCL6 BTB domain dimer. This lateral groove/BBD interaction is required for the BCL6 domain to recruit the SMRT, N-CoR, and BCoR corepressors, and is essential for the repression activity of BCL6. The peptides contain a common aromatic residue that fits into a pocket within the lateral groove and they adopt a similar pseudo-structure upon binding. Also, the SMRT, N-CoR, and BCoR BBDs bind specifically to the BCL6-BTB but not to other BTB domains from any other protein member of the family.

Approximately 80% of patients with DLBCL responded to conventional chemotherapy consisting of cyclophosphamide, doxorubicin, vincristine, and prednisone (CHOP), but less than 40% were likely to be cured. Randomized trials showed that the addition of rituximab (R) to conventional CHOP chemotherapy improves outcomes including overall survival, establishing R-CHOP as the standard of care. A recent analysis of outcomes on the US Intergroup Trial (E4494) comparing CHOP to R-CHOP and maintenance rituximab indicated that the benefit observed with the addition of rituximab was attributable to a powerful effect on the BCL6 negative cases only. Cases positive for BCL6 did not benefit from the addition of rituximab to CHOP chemotherapy. The mechanism by which the addition of rituximab to CHOP improves outcomes selectively in the BCL6 negative cases is unknown but could be related to antibody-dependent cellular cytotoxicity, complement-mediated cytotoxicity, induction of apoptosis or an as yet uncharacterized effect unique to BCL6 negative DLBCL. These findings underscore the fact that the DLBCLs represent at least two biologically distinct diseases that will require different treatment approaches to improve upon current outcomes. To date, clinical trials for DLBCL have not distinguished between the different subgroups. Therapeutic strategies must be designed to specifically target BCL6 positive and negative DLBCL based upon their unique biological differences.

SUMMARY

The invention provides, in various embodiments, a method of disrupting BCL6 BTB domain interactions with corepressors, in B-cells, comprising exposing the B cells to an effective concentration of a compound that blocks the lateral groove of BCL6; a method of inhibiting DLBCL tumor growth, or causing DLBCL tumor regression, or both, in a mammal, comprising administering to the mammal an effective dose of a compound that blocks the BTB lateral groove of BCL6; a method of inhibiting transcriptional repression induced by a complex of BCL6 with SMRT or other corepressor proteins in cancer cells, comprising exposing the cancer cells to an effective concentration of a compound that blocks the BTB lateral groove of BCL6; and a method of treatment of a patient afflicted with cancer, comprising administering to the patient an effective dose of a compound that blocks the BTB lateral groove of BCL6. The practice of these methods can be accomplished using BCL6-binding compounds of the invention as disclosed herein.

The invention further provides compounds of various formulas, effective for carrying out a method of the invention, as disclosed and claimed herein.

BRIEF DESCRIPTION OF THE FIGURES

FIGS. 5, 6A and 6B show graphs of bioactivities of compounds of the 3033 series analogous to the results shown for FIG. 1.

FIGS. 7A and 7B shows graphs of bioactivities of compounds of the 3033 series and other compounds analogous to the results shown for FIG. 1.

FIGS. 9A and 9B shows biodata for compounds of the 3077 irreversible inhibitor series.

DETAILED DESCRIPTION

Figure 1:
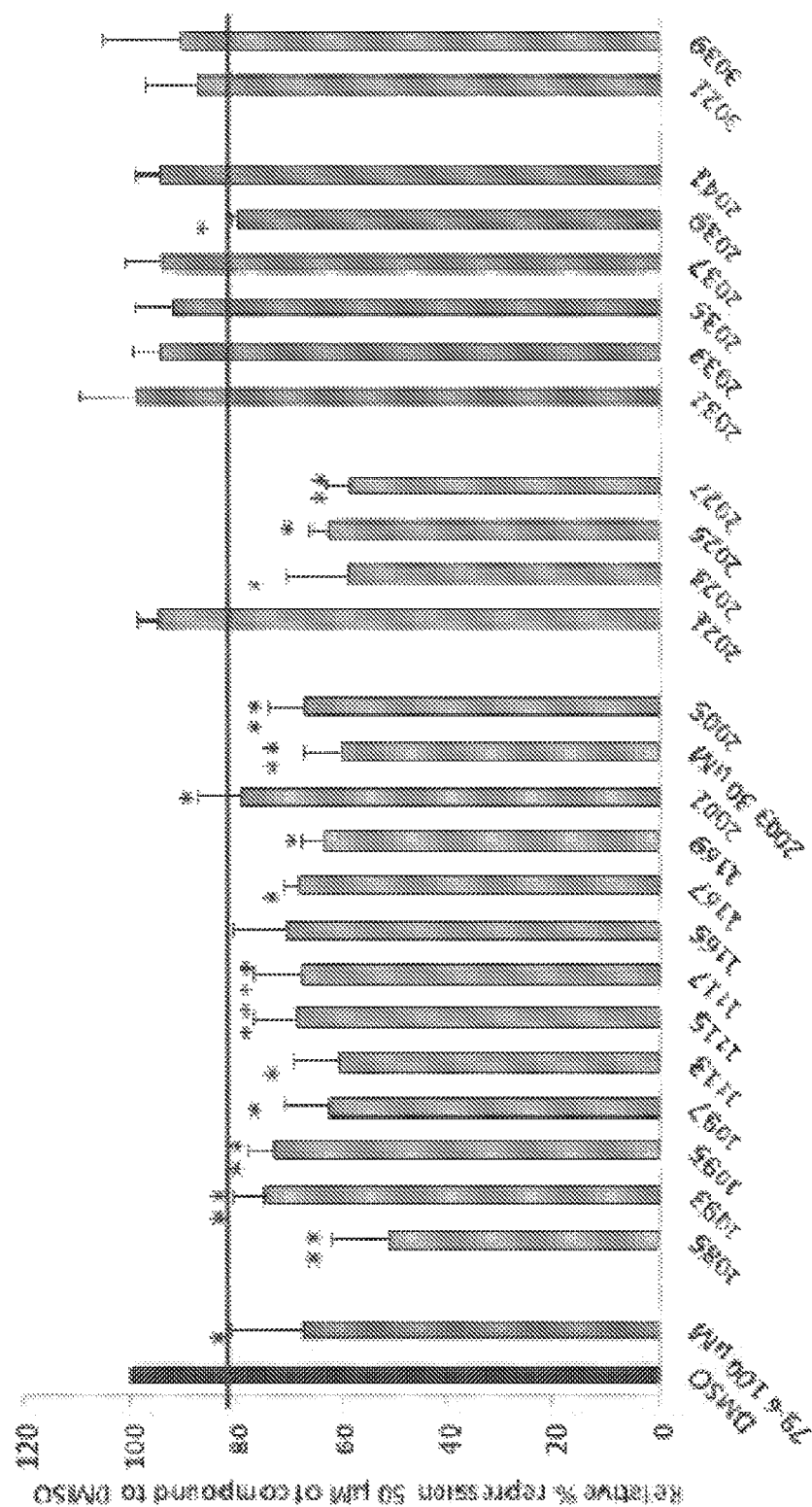
FIG. 1 shows a graph of bioactivities of compounds of the 1085 series in a reporter assay in which a GAL4-DNA binding domain (DBD)-BCL6$^{BTB}$ fusion construct was co-transfected with a luciferase reporter plasmid containing GAL4 DBD binding sites, (GAL4)5TK-Luc in 293T cells. The fold change in the repressor activity of the BCL6$^{BTB}$ domain, shown in graphic form, was determined in the presence of either the compounds at different concentrations, or DMSO alone (2 μL/mL), used as a vehicle of dilution of the compounds, and was controlled for nonspecific effects on transcription by normalizing to the activity of the GAL4-DBD alone. The results presented are the average and standard deviation of three independent experiments (**=p<0.005; *=p<0.05 t-test).

BCL6 was first identified as the most frequently deregulated gene in diffuse large B-cell lymphomas (DLBCL). The translocations of this gene cause BCL6 to be constitutively expressed downstream of heterologous promoter regions. DLBCLs are aggressive tumors that arise from germinal center (GC) B-cells and are the most common form of non-Hodgkin's lymphomas. GCs are transient structures that form within lymphoid follicles triggered by exposure to antigenic stimulation. The current standard treatment of DLBCL involves the RCHOP regimen. This polychemotherapy regimen can cure approximately 80% of GCB-type DLBCLs and 40% of ABC-DLBCLs. Hence many DLBCL patients still relapse from chemotherapy and need better treatments. BCL6 inhibitors are effective in both ABC and GCB type DLBCLs, and are highly active even in lymphoma cells from chemo-resistant patients. Moreover BCL6 inhibitors synergize with chemotherapy and could be used to help eradicate DLBCLs that would otherwise relapse. Given how powerful and yet non-toxic BCL6 targeted therapy appears to be, it seems that BCL6 inhibitors could serve as an anchor for combination therapies without fear of significant cross-toxicities. Also, BCL6 inhibitors are active in two of the worst subtypes of Acute B-Lymphoblastic leukemia (B-ALL), those with MLL translocations and those with BCR-ABL translocations. Most of these patients die of their disease. There is a clear need for a meaningful therapeutic agent that could help these patients.

Likewise, the therapy of acute myeloid leukemia (AML) has changed little over the past 30 years and most patients still die of their disease. Again BCL6 therapy may provide an important new modality for these patients. Targeting BCL6 requires disrupting protein-protein interactions and our BCL6 inhibitors approach is one of the first or possibly the first example where this has been achieved for therapeutic effect against an oncogenic transcription factor. The only known BCL6 inhibitors that target the lateral groove are the BPI (BCL6 peptide inhibitor) peptides and 79-6, described below. However, BPI suffers from lack of oral bioavailability, potential immunogenicity, and high cost while 79-6 is limited with respect to affinity and stability. This study is innovative in two aspects: novel sweet spots on the BTB lateral groove of BCL6 were identified, including the aromatic, arene, and HDCH pockets, and exploited to facilitate the first truly rational design of small molecule BCL6 inhibitors. Pocket characterization and inhibitor design were driven by a novel target-based CADD method, Site Identification by Ligand Competitive Saturation (SILCS, see Guvench, O., and MacKerell, A. D., Jr. "Computational Fragment-Based Binding Site Identification by Ligand Competitive Saturation, *PLoS Computational Biology*, 5: e1000435, 2009, PMC2700966), which can be used together with medicinal chemistry, structural studies and biological assays in an iterative approach to optimize the pharmacodynamic (PD) and pharmacokinetic (PK) properties of the inhibitors. Second, a cysteine residue located in the novel HDCH binding pocket in the lateral groove was targeted to develop specific, irreversible BCL6 inhibitors. The proposed research has the potential to treat other important human cancer such as FLs, various forms of leukemia and breast cancer, and teach us how the inhibition of BCL6 and subsequent gene repression affects cancer To identify novel BCL6 inhibitors, we first used applied the SILCS methodology using the crystal structure of the BCL6-BTB/SMRT-BBD complex (PDB ID 1R2B). The resulting SILCS FragMaps, which represent the affinity pattern of the protein for different types of functional groups, was used to design novel compounds targeting the BTB lateral groove. Top scoring designed compounds were then synthesized and evaluated using functional assays including microscale thermophoresis protein binding, NMR, DLBCL differential killing and BCL6 BTB domain reporter assays. We therefore synthesized different groups of compounds.

A retro-inverso peptide that blocks the oncogenic activity of BCL6 was developed; studies done by certain of the inventors herein have led to the development of a recombinant peptide containing the SMRT BBD and a pTAT protein transduction domain that occupies the BCL6 BTB lateral groove and prevents binding of the SMRT, N-CoR, and BCoR corepressors. The BPI (BCL6 peptide inhibitor) was specific to BCL6 and shown to activate BCL6-target genes in DLBCL cells. Intraperitoneal injections of BPI in mice reproduced the BCL6 null phenotype. BPI also had specific and potent anti-lymphoma activity, inducing apoptosis in a panel of BCL6 expressing DLBCL cell lines but no effect for BCL6 negative cell lines. The BPI peptide analog is disclosed in PCT/US2009/003483, published as WO 2010/008436.

These data demonstrate that BCL6 is a therapeutic target that can be effectively and specifically blocked by occluding its BTB domain lateral groove. Although the peptide is very stable, it is extremely expensive and difficult to produce due to the need for D-aminoacid series in a pure state. Therapeutic targeting of the BCL6 lateral groove is disclosed in PCT/US2004/042418, published as WO2005/058939, (and corresponding U.S. application Ser. No. 10/582,662, now U.S. Pat. No. 7,919,578), filed Dec. 16, 2004, the disclosure of which is incorporated herein by reference in its entirety.

A small molecule inhibitor of BCL6 that kills DLBCL cells in vitro and in vivo was then developed. Compound 79-6 specifically inhibits BCL6 but not other BTB domains such as HIC1 (hypermethylated in cancer 1), PLZF (promyeloctic zinc finder), and Kaiso.

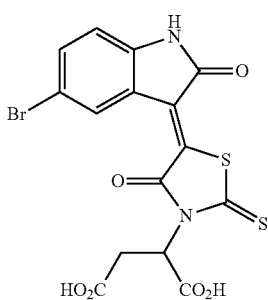

79-6

Compound 79-6, shown above, is disclosed in PCT/US2007/024571, filed Nov. 30, 2006, published as WO2008/066887, and in U.S. Ser. No. 12/312,800, now U.S. Pat. No. 8,338,464; the disclosures of which publications are incorporated herein by reference in their entireties. Compound 79-6 disrupts BCL6 transcriptional complexes and reactivates BCL6 target genes. Compound 79-6 selectively kills BCR DLBCL sells. It is not toxic and suppresses human DLBCL xenografts in mice. Compound 79-6 selectively kills primary BCL6+ DLBCL cells. The X-ray crystallographic structure of the BCL6$^{BTB}$/79-6 complex shows one molecule of compound 79-6 to bind in each of lateral grooves of the BLC6 BTB dimer. This compound provided a very good structural lead, but novel compounds that are more potent, and that are soluble and stable in water solution are needed in order to improve efficacy in the treatment of lymphomas in humans. Reference is made to publications cited herein, the disclosures of which are incorporated by reference in their entireties.

The present invention describes, in various embodiments, novel inhibitors of BCL6 repression activity that act through binding to the lateral groove motif of the BLC6 BTB domain thereby preventing its interaction with the co-repressor complex, that are effective for use as anti-lymphoma agents. Various classes have compounds have been devised, as disclosed and claimed herein, that can be used for treatment of lymphomas such as BCL6+ Diffuse Large B-Cell lymphomas. We identified novel inhibitors with improved potency that were structurally similar to the previously discovered lead 79-6.

Based on the X-ray structure of 79-6 with BCL6, we designed analogs that queried 1) the substituent(s) on the indolin-2-one ring, and 2) the linker length between the rhodanine and the carboxylic acid tail, with the goal of identifying a ligand with one acid group, thereby likely having improved PK properties. These efforts identified 79-6 analog 1085, which contains a 5-Cl substituent on the indolin-2-one ring and a mono carboxylic acid.

To map the functional group requirement of the 79-6 binding pocket to direct ligand design we have applied the SILCS methodology. In the SILCS method a collection of small molecules representative of different classes of functional groups compete with each other and with water for the surface of the protein during a series of MD simulations. From these simulations 3D probability distribution maps, termed FragMaps, are obtained which identify regions of the protein surface with which different types of functional groups have favorable interactions with the protein, information that can direct ligand design. Notably, SILCS allows for 1) qualitative analysis of the protein-binding pocket to allow visualization and subsequent prediction of synthetically accessible modifications of ligands that should improve activity and for 2) quantitative estimates of changes in binding affinity associated with the addition of the predicted functional groups. Evident is the overlap of aromatic and aliphatic FragMaps, which defines the aromatic pocket, with the indolin-2-one ring of 79-6 and of charged acceptor FragMaps with the acid groups, which defines the acid site. These results emphasize the importance of these functional groups for the activity of 79-6. Notably, the aromatic and aliphatic FragMaps are extended to encompass the Br atom on the 5 position of the indolin-2-one, indicating that this position is the most likely position for a substituent as validated in compound 1085. The lack of FragMaps coinciding with the rhodanine ring indicates that it is acting as a scaffolding element in the ligand rather than making a significant contribution to binding. The FragMaps also indicate that only one of the two carboxylate groups is necessary to form the key charge-charge interaction with the acid site associated with the side chain of Arg28, a result that has been subsequently validated by the activity of FX-1085. With respect to future design options, adjacent to the indolin-2-one ring is an aromatic/aliphatic FragMap, defining the arene pocket.

After testing the effect of 25 different derivatives in a reporter assay (FIG. 1), we identified the new compound 1085 as the most potent and selective one (FIG. 2), with better affinity to the BCL6-BTB domain compared to 79-6 and even to the natural ligand peptide SMRT. Under the assay conditions, 1085 had a Kd of (5±4)µM, whereas 79-6 had a Kd ~120 µM. The superposition of the 15N-1H HSQC spectra for Bcl6 BTB alone and spectra in the presence of 1085 shows a similar pattern to the one observed with the 79-6 BCL6-BTB interaction, confirming that the binding site is similar for both compounds. The novel compound also shows differential gene expression similar to the silencing of the protein induces the derepression of BCL6 target genes and prevents the corepressor complex proteins SMRT or BCOR to be bound to BCL6 that is interacting with the target sequences. BCL6 is also required for normal development of germinal center (GC) B-cells. Treatment of immunized mice for 10 days with 100 mg/kg 1085 inhibited the germinal center, confirming the effect of 1085 as a BCL6 inhibitor. This compound has favorable pharmacokinetics in vitro and in vivo, is very stable in solution and didn't induce any toxic effects in mice after 10 days of treatment with 125 mg/kg. As expected, 1085 is a very effective and selective inhibitor of BCL6 dependent GCB DLBCLs in vitro and in vivo that induces tumor regression in 95% of the tumors. Noteworthy, BCL6 dependent aggressive ABC DLBCLs were also sensitive to the in vitro and in vivo treatment with 1085, and even primary human ABC DLBCL samples were sensitive to the treatment with the new BCL6 inhibitor.

Thus, the invention provides, in various embodiments, a compound of the 1085 series, exemplified as shown in Table 1, below, based on the lead structure of 1085. A reporter assay in which a GAL4-DNA binding domain (DBD)-BCL$^{BTB}$ fusion construct was co-transfected with a luciferase reporter plasmid containing GAL4 DBD binding sites, (GAL4)5TK-Luc in 293T cells. The fold change in the repressor activity of the BCL6$^{BTB}$ domain, shown in graphic form in FIG. 1, was determined in the presence of either the compounds at different concentrations, or DMSO alone (2 µL/mL), used as a vehicle of dilution of the compounds, and was controlled for nonspecific effects on transcription by normalizing to the activity of the GAL4-DBD alone. The results presented are the average and standard deviation of three independent experiments (**=p<0.005; *=p<0.05 t-test).

TABLE 1

Examples of the 1085 series

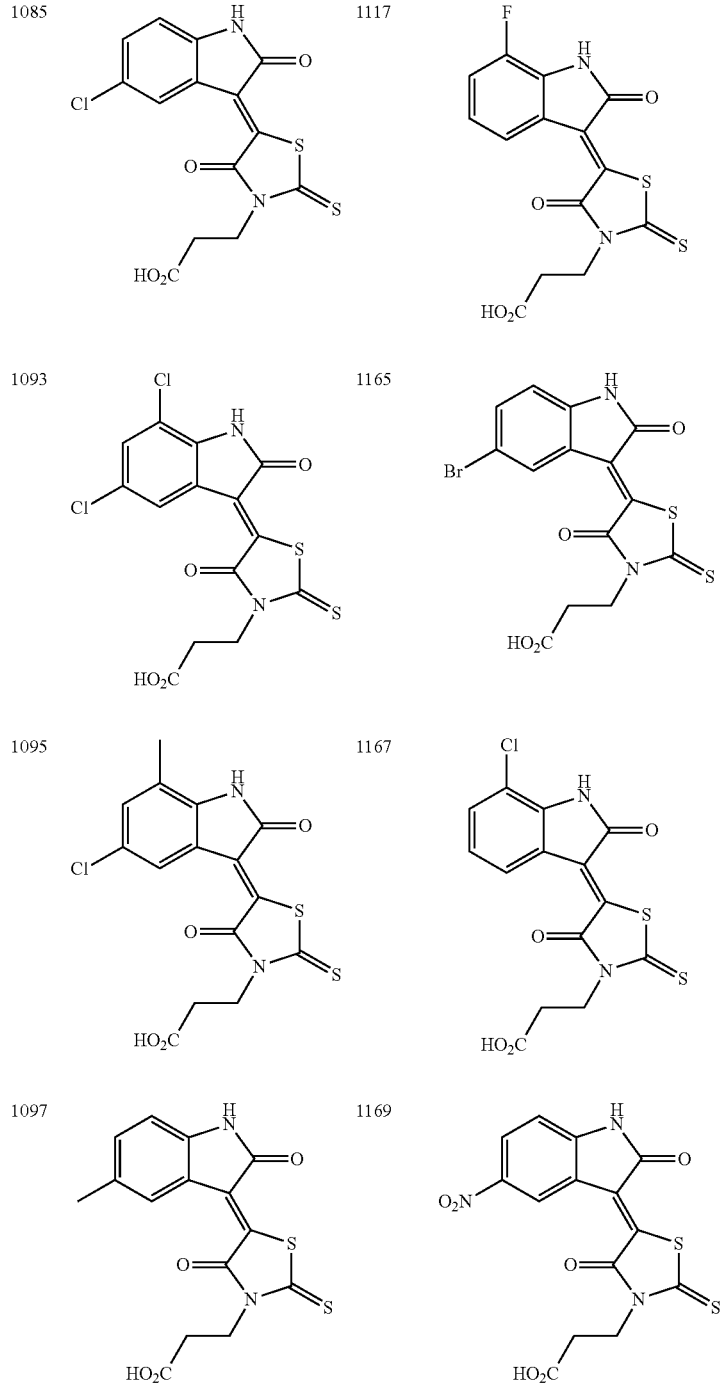

TABLE 1-continued

Examples of the 1085 series

TABLE 1-continued

Examples of the 1085 series 2027, 2039, 2031, 2041, 2033, 3021, 3039 [chemical structures]

Most of the compounds of this family were active in the reporter assay, being able to inhibit the repression activity of BCL6 more than 20%. The most active compound was 1085, inhibiting the repression activity of BCL6 approximately 50%. In this assay, the compounds are tested by their capacity to inhibit the repressor activity of BCL6-BTB, but also need to penetrate the cell membrane and interact with the protein in order to produce the inhibition, so the permeability of the cell is also tested.

Figure 2:
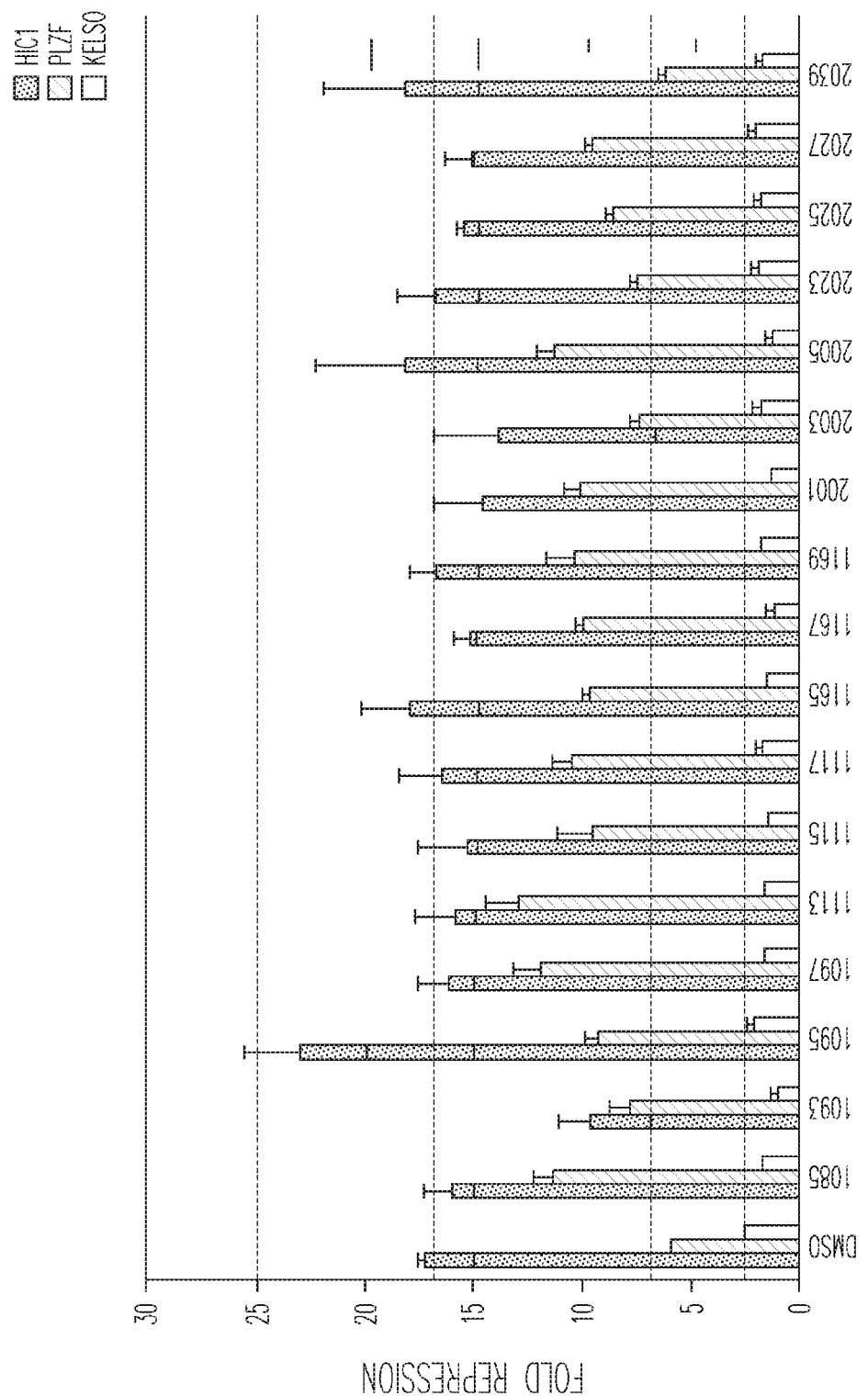
FIG. 2 shows a graph of the compounds of the 1085 series in a reporter assay performed under the same conditions as in the assay of FIG. 1, but transfecting cells either with GAL4 DNA binding domain (DBD)-HIC1-BTB, PLZF-BTB, or Kaiso-BTB fusion constructs instead of BCL6-BTB.

To test the selectivity of the compounds a similar reporter assay was performed under the same conditions as in the assay of FIG. 1, but transfecting cells either with GAL4 DNA binding domain (DBD)-HIC1-BTB, PLZF-BTB, or Kaiso-BTB fusion constructs instead of BCL6-BTB. Results are shown in FIG. 2, suggesting that none of the tested compounds significantly affected the repression activity of the HIC1, PLZF, or Kaiso BTB domains.

50,000 cells per well were treated for 48 hours with different concentrations of the compounds in 96 well plates, using DMSO as a control. Then, viability was determined with Cell Titer Blue™ (Promega) and growth inhibition was calculated as the percentage of viable cells with respect to cells treated with DMSO alone. $GI_{50}$ values were determined by dose-response curves. Results are presented in Table 2, below.

TABLE 2
Growth inhibition effects of 1085 compounds on DLBCL cells
| | BCL-6 dependent | | | | BCL-6 independent | | |
| --- | --- | --- | --- | --- | --- | --- | --- |
| | | | | | Karpas | | |
| Compound | Ly3 | Ly7 | Ly10 | SUDH6 | 422 | Toledo | Ly1B50 |
| | | | | GI$_{50}$ (µM) | | | |
| 1085 | >40 | 23 ± 9 | 23.5 ± 0.2 | 14 ± 7 | >40 | >40 | >40 |
| 1093 | >40 | 30 ± 9 | 21 ± 12 | >40 | >40 | >40 | >40 |
| 1095 | >40 | >40 | >40 | >40 | >40 | >40 | >40 |
| 1097 | >40 | >40 | 18 ± 8 | >40 | >40 | >40 | >40 |
| 1113 | >40 | 12 ± 7 | >40 | >40 | >40 | >40 | >40 |
| 1115 | 22 ± 9 | 24 ± 6 | 34 ± 3 | 26 ± 7 | >40 | >40 | >40 |
| 1117 | 21 ± 4 | 36 ± 1 | >40 | 25 ± 4 | >40 | >40 | >40 |
| 1165 | 17 ± 6 | >40 | 25 ± 9 | >40 | >40 | >40 | >40 |
| 1167 | >40 | 22 ± 1 | 24 ± 2 | 29 ± 1 | >40 | >40 | >40 |
| 1169 | 29 ± 5 | 28 ± 7 | 20 ± 10 | 30 ± 3 | 27 ± 8 | >40 | >40 |
| 2001 | >40 | >40 | >40 | >40 | >40 | >40 | >40 |
| 2003 | >6 | >6 | >6 | >6 | >6 | >6 | >6 |
| 2005 | >40 | >40 | 21 ± 2 | 25 ± 6 | >40 | >40 | >40 |
| 2021 | >40 | >40 | >40 | >40 | >40 | >40 | >40 |
| 2023 | >40 | 21 ± 10 | >40 | 21 ± 3 | >40 | >40 | >40 |
| 2025 | >40 | 13 ± 1 | 15 ± 8 | 14 ± 2 | 22 ± 7 | >40 | >40 |
| 2027 | 14 ± 3 | 8 ± 1 | 6 ± 2 | 7 ± 1 | >40 | >40 | >40 |
| 2031 | >40 | >40 | >40 | >40 | >40 | >40 | >40 |
| 2033 | >40 | >40 | >40 | >40 | >40 | >40 | >40 |
| 2035 | >40 | >40 | >40 | >40 | >40 | >40 | >40 |
| 2037 | >40 | >40 | >40 | >40 | >40 | >40 | >40 |
| 2039 | >40 | >40 | >40 | >40 | >40 | >40 | >40 |
| 2041 | >40 | >40 | >40 | >40 | >40 | >40 | >40 |
TABLE 3
Compounds of the 2099 series
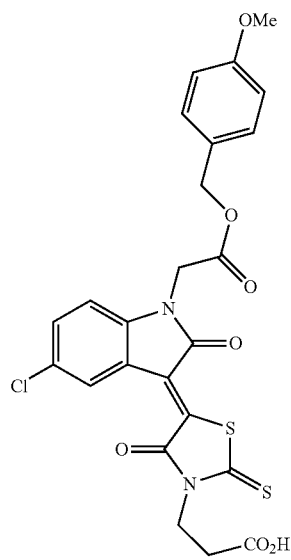 [SMILES: COc1ccc(COC(=O)CN2C(=O)/C(=C3\SC(=S)N(CCC(=O)O)C3=O)c3cc(Cl)ccc32)cc1]
371
TABLE 3-continued
Compounds of the 2099 series
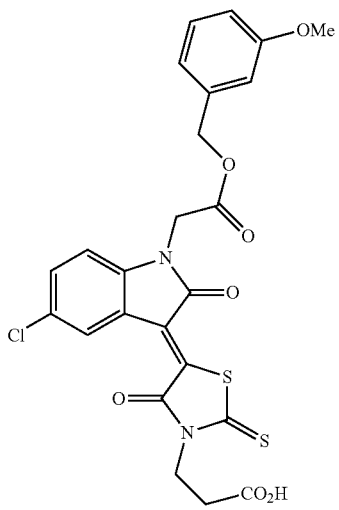 [SMILES: COc1cccc(COC(=O)CN2C(=O)/C(=C3\SC(=S)N(CCC(=O)O)C3=O)c3cc(Cl)ccc32)c1]
372

TABLE 3-continued
Compounds of the 2099 series
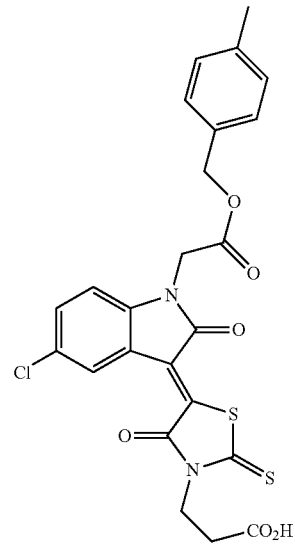 [SMILES: Cc1ccc(COC(=O)CN2C(=O)/C(=C3\SC(=S)N(CCC(=O)O)C3=O)c3cc(Cl)ccc32)cc1]
373
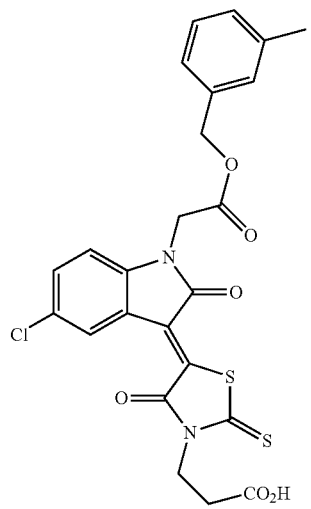 [SMILES: Cc1cccc(COC(=O)CN2C(=O)/C(=C3\SC(=S)N(CCC(=O)O)C3=O)c3cc(Cl)ccc32)c1]
374
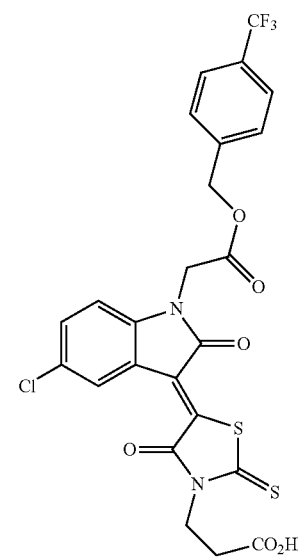 [SMILES: O=C(O)CCN1C(=O)/C(=C2/C(=O)N(CC(=O)OCc3ccc(C(F)(F)F)cc3)c3ccc(Cl)cc32)SC1=S]
375
TABLE 3-continued
Compounds of the 2099 series
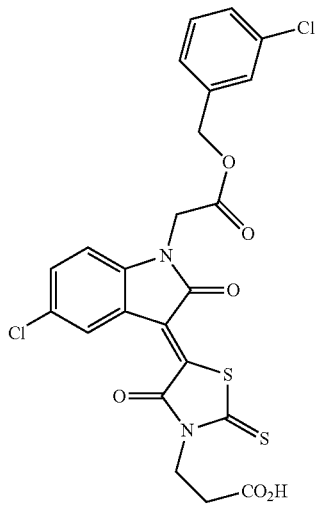 [SMILES: O=C(O)CCN1C(=O)/C(=C2/C(=O)N(CC(=O)OCc3cccc(Cl)c3)c3ccc(Cl)cc32)SC1=S]
376
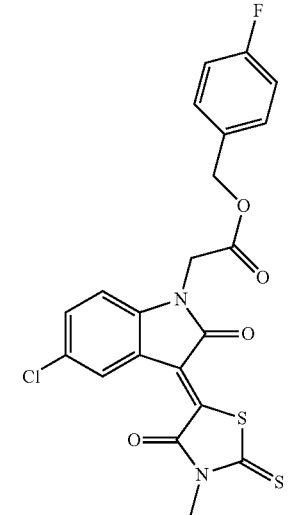
377
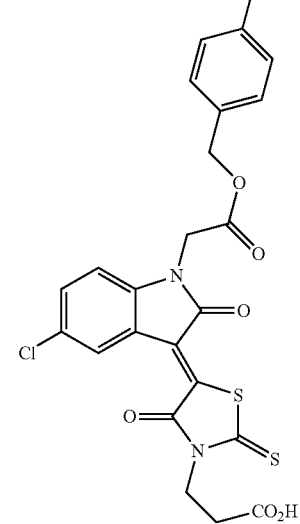
378

TABLE 3-continued
Compounds of the 2099 series
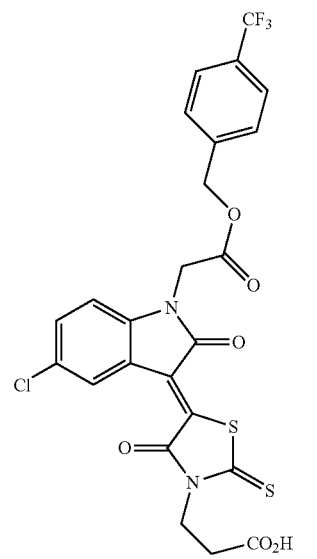 [SMILES: O=C(O)CCN1C(=O)/C(=C2/C(=O)N(CC(=O)OCc3ccc(C(F)(F)F)cc3)c3ccc(Cl)cc32)SC1=S] 379
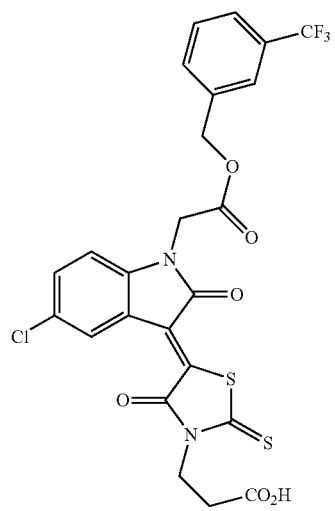 [SMILES: O=C(O)CCN1C(=O)/C(=C2/C(=O)N(CC(=O)OCc3cccc(C(F)(F)F)c3)c3ccc(Cl)cc32)SC1=S] 380
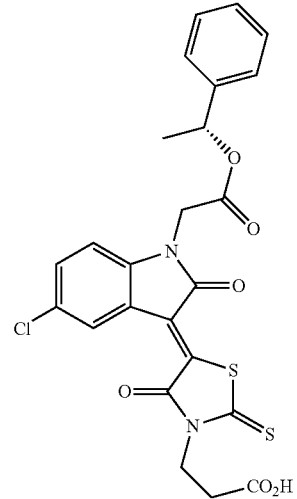 [SMILES: C[C@@H](OC(=O)CN1C(=O)/C(=C2\SC(=S)N(CCC(=O)O)C2=O)c2cc(Cl)ccc21)c1ccccc1] 381
TABLE 3-continued
Compounds of the 2099 series
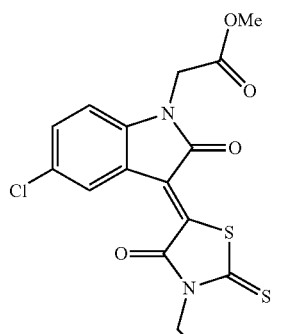 382
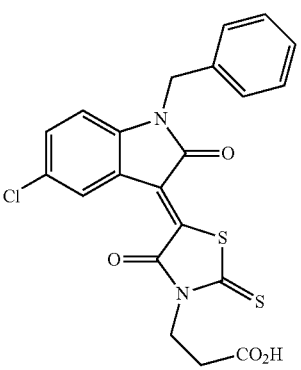 [SMILES: O=C(O)CCN1C(=O)/C(=C2/C(=O)N(Cc3ccccc3)c3ccc(Cl)cc32)SC1=S] 383
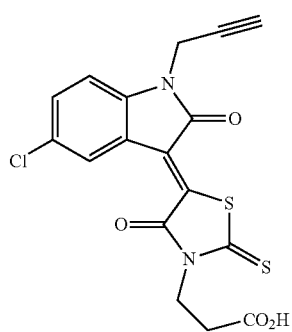 [SMILES: C#CCN1C(=O)/C(=C2\SC(=S)N(CCC(=O)O)C2=O)c2cc(Cl)ccc21] 384
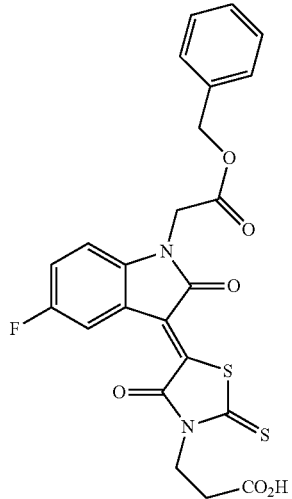 2097

TABLE 3-continued

Compounds of the 2099 series

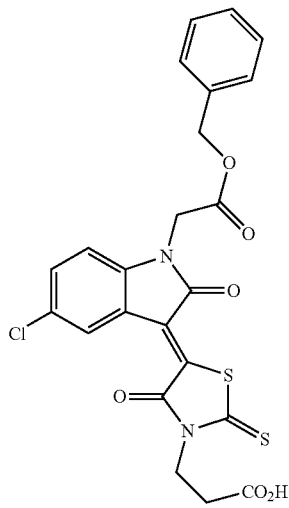 [SMILES: O=C(O)CCN1C(=O)/C(=C2/C(=O)N(CC(=O)OCc3ccccc3)c3ccc(F)cc32)SC1=S]

2099

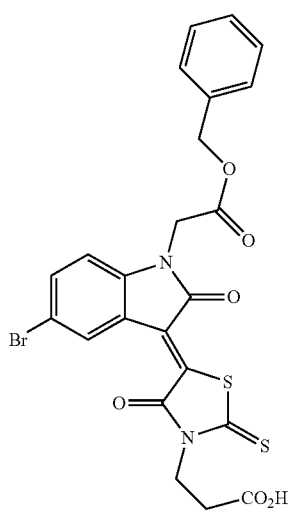

2101

TABLE 3-continued

Compounds of the 2099 series

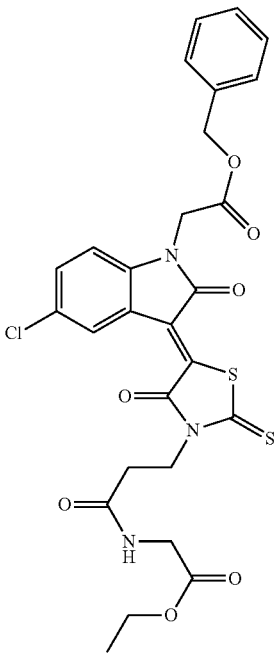 [SMILES: CCOC(=O)CNC(=O)CCN1C(=O)/C(=C2/C(=O)N(CC(=O)OCc3ccccc3)c3ccc(Cl)cc32)SC1=S]

3022

The toxicity of the compound 1085, the most active and specific BCL6 inhibitor of this series, was tested. The compound was found to have a selective BCL6-dependent DLBCL inhibitor activity with a $GI_{50}$ between 14 and 23 µM. First, the stability of the compound in the administration vehicle of 30% PEG-300, 5% Tween-80, and 65% dextrose 5%, was evaluated at room temperature over a period of up to 8 days by NMR spectroscopy.

No significant changes in the structure were observed after the 8 day evaluation. The toxic effects of 1085 on mice were then examined. Five C57BL/6 mice were exposed to daily intraperitoneal (IP) administration of increasing doses of the compound ranging from 50 to 150 mg/kg over the course of 7 days, to a cumulative dose of 750 mg/kg, and another five mice were exposed to vehicle only. No toxic effects or other indicators of sickness, including significant weight loss or tissue damage (macroscopic or microscopic) were noted. Brain, heart, lung, liver, kidney, bowel, spleen, and bone marrow tissues were examined. Complete peripheral blood counts, biochemistry and liver function tests were normal.

A series of N-substituted oxindoles and oxindole analogs was then prepared and tested in the same bioassays. Table 3, above, shows examples of compounds in the series designated the 2099 series.

Figure 3:
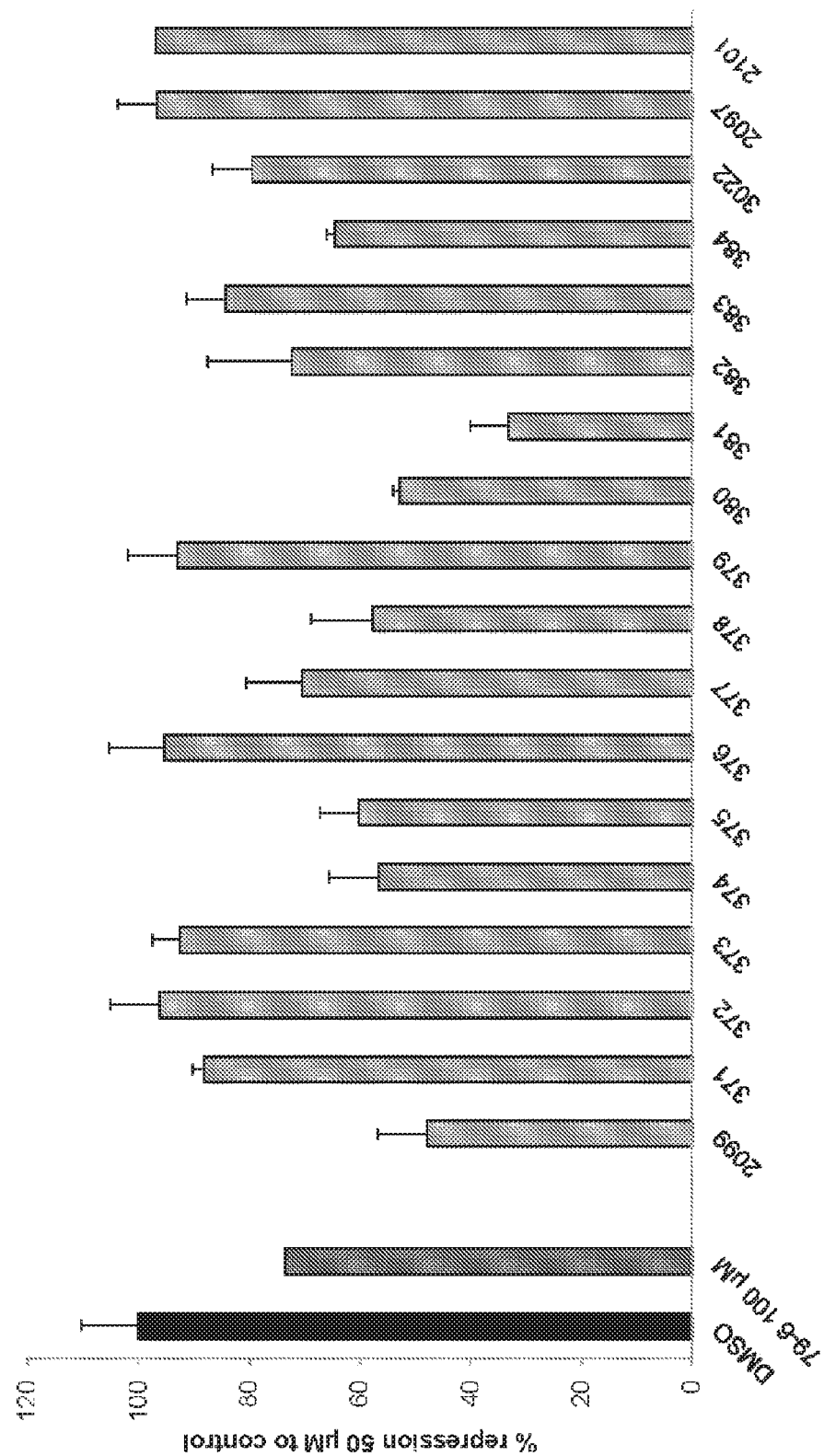
FIG. 3 shows a graph of bioactivities of compounds of the 2099 series analogous to the results shown for FIG. 1.

FIG. 3 shows biodata results indicating the % repression at a 50 µM level of the compound relative to control. Tables 4 and 5 show quantitative results of the bioassays on BCL6-dependent and BCL6-independent cell lines.

TABLE 4

| | Bcl6 dependent | | | | Bcl6 independent | | |
| | | | GI 50 (μM) | | | | |
| | Ly3 | Ly1 | SUDHL6 | Ly7 | Toledo | K422 | WSUDLCL2 | Ly1B50 |
|---|---|---|---|---|---|---|---|---|
| 374 | >125 | >125 | 48 ± 17 | >125 | >125 | >125 | 99 ± 20 | >125 |
| 375 | >125 | >125 | 29 ± 14 | >125 | >125 | >125 | >125 | >125 |
| 377 | >125 | >125 | 104 | >125 | >125 | >125 | >125 | >125 |
| 378 | >125 | >125 | 53.4 | >125 | >125 | >125 | >125 | >125 |
| 380 | 71 ± 18 | 106 ± 20 | 18 ± 7 | 94 ± 19 | 93 ± 23 | 69 ± 4 | 67 ± 12 | 68 |
| 381 | >125 | >125 | 22 ± 8 | >125 | >125 | >125 | >125 | >125 |

TABLE 5

| | | BCL6 | BCL6 dependent | |
| Compound | Kd (μM) | independent GI$_{50}$ Toledo (μM) | GI$_{50}$ Ly7 (μM) | GI$_{50}$ SUDHL6 (μM) |
|---|---|---|---|---|
| 2099 | 5.5 ± 0.7 | 75 | 65 | 30 ± 7 |

Accordingly, the invention provides, in various embodiments, a compound of formula I

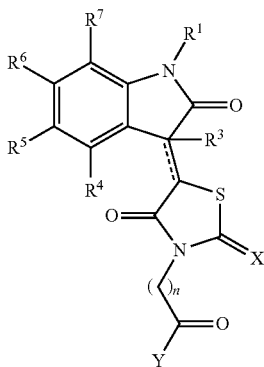

wherein a dashed line indicates that a double bond can be present or absent; when a double bond is present, $R^3$ is absent; $R^1$ is H, (C1-C6)alkyl, benzyl, 2-propenyl or 2-propynyl, or $R^1$ is a group of formula —$CH_2CO_2R$ or of —$CH_2C(=O)OCH(R)$—$Ar^1$, wherein R is H or (C1-C6) alkyl, $Ar^1$ is phenyl substituted with 0, 1, or 2 independently selected substituents from the group consisting of (C1-C6) alkyl, (C1-C6)alkoxy, halo, and (C1-C6)haloalkyl; n=1, 2, or 3; $R^3$ is H or OH; each of $R^4$, $R^5$, $R^6$ and $R^7$ is independently selected H, F, Cl, Br, or I; X is O or S; Y is OH or O(C1-C6)alkyl; or a pharmaceutically acceptable salt thereof; provided that when $R^1$ is H, Y is OH, the double bond indicated by the dashed line is present and $R^3$ is absent, and n=1, 2, or 3, not all of $R^4$, $R^5$, $R^6$ and $R^7$ are H; and when $R^1$ is H, methyl, or 2-propenyl, Y is OH, the double bond indicated by the dashed line is present and $R^3$ is absent, n=1, 2 or 3, and $R^4$, $R^5$ and $R^7$ are H, $R^6$ is not bromo.

The compound can be any of the compounds of Table 1 or Table 3, above, i.e., the compound can be any one of 1085, 1093, 1095, 1097, 1113, 1115, 1117, 1165, 1167, 1169, 2001, 2003, 2005, 2021, 2023, 2025, 2027, 2031, 2033, 2035, 2037, 2039, 2041, 2097, 2099, 2101, 3021, 3022, 3039, 371, 372, 373, 374, 375, 376, 377, 378, 379, 380, 381, 382, 383, or 384, or a pharmaceutically acceptable salt thereof.

The invention also provides, in various embodiments, a method of disrupting BCL6 BTB domain interactions with corepressors, in B-cells, comprising exposing the B cells to an effective concentration of a compound that blocks the lateral groove of BCL6.

The invention also provides, in various embodiments, a method of inhibiting DLBCL tumor growth, or causing DLBCL tumor regression, or both, in a mammal, comprising administering to the mammal an effective dose of a compound that blocks the BTB lateral groove of BCL6.

The invention also provides, in various embodiments, a method of inhibiting transcriptional repression induced by a complex of BCL6 with SMRT or other corepressor proteins in cancer cells, comprising exposing the cancer cells to an effective concentration of a compound that blocks the BTB lateral groove of BCL6.

The invention also provides, in various embodiments, a method of treatment of a patient afflicted with cancer, comprising administering to the patient an effective dose of a compound that blocks the BTB lateral groove of BCL6.

The expressions "effective amount" or "effective dose", when used to describe therapy to an individual suffering from a disorder, refers to the quantity or concentration of a compound of the invention that is effective to inhibit or otherwise act on BCL6 in the individual's tissues wherein BCL6 involved in the disorder, wherein such inhibition or other action occurs to an extent sufficient to produce a beneficial therapeutic effect.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

In carrying out any one of these methods, the compound that blocks the lateral groove of BCL6 can be a compound of formula I, or can be any one of the specific compounds of Table 1 or Table 3, i.e., can be any one of 1085, 1093, 1095, 1097, 1113, 1115, 1117, 1165, 1167, 1169, 2001, 2003, 2005, 2021, 2023, 2025, 2027, 2031, 2033, 2035, 2037, 2039, 2041, 2097, 2099, 2101, 3021, 3022, 3039, 371, 372, 373, 374, 375, 376, 377, 378, 379, 380, 381, 382, 383, or 384, or a pharmaceutically acceptable salt thereof.

SILCS analysis indicated the presence of HDCH binding pocket and, in combination with experimental data on 79-6 analogs, showed that both the indole fragment and the carboxylate end are required for the binding of 79-6, while the rhodanine ring system is not essential.

Based on the SILCS data a new class of inhibitors for BCL6 were designed in which the chemical structure of 1085 was extended with an additional hydrophobic group. A collection of 18 analogs was designed and synthesized to 1) keep the overall planar configuration of the inhibitor and, 2) provide hydrophobic and hydrogen bonding functional groups that would interact with the HDCH pocket and, thus, further improve the potency and specificity of the inhibitors. SILCS calculations indicate that an additional aliphatic or aromatic system (green/purple mesh) added on NH group of the indole ring would increase potency. Accordingly, we have extended the indole fragment with hydrophobic groups such as alkyl, benzyl, phenyl acetate, and benzyl acetate or benzyl acetamide.

Additional compounds were next designed and synthesized with the rhodanine ring removed from the scaffold. These novel inhibitors targeting BCL6 are capable of binding simultaneously to the aromatic pocket and to the HDCH site but omit the rhodanine and carboxylic acid moieties. Omission of the carboxylic acid moiety, though essential for 79-6 and 1085 binding, was performed to determine if addition of moieties targeting the HDCH sites would compensate for the loss of that group.

In various embodiments, the invention provides a compound of formula II, as described below, and in various embodiments provides a compound of formula II for carrying out any of the above-described methods of blocking the BTB lateral groove of BCL6 with an effective amount or concentration of the compound of formula II, including a compound of the 2071/3033 series.

The invention provides a compound of the 2071/3033 series of formula II, or the use of a compound of Table 7, below, for carrying out any of the methods of blocking the BTB lateral groove of BCL6.

Accordingly, the invention provides a compound of formula II

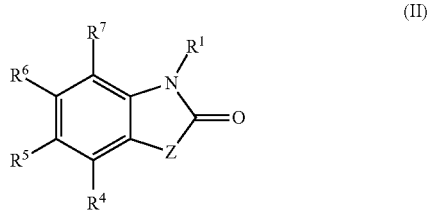

(II)

wherein Z is O, $CH_2$, $CCl_2$, or C(=O); $R^1$ is a group of formula —$CH_2CO_2R$, —$CH_2C$(=O)OCH(R)—$Ar^1$ or —$CH_2C$(=O)N(R)CH(R)—$Ar^1$, wherein each R is independently H or (C1-C6)alkyl, $Ar^1$ is phenyl or heteroaryl substituted with 0, 1, or 2 independently selected substituents from the group consisting of (C1-C6)alkyl, (C1-C6)alkoxy, halo, $NR_2$, N(R)C(=O)O(C1-C6)alkyl, and (C1-C6)haloalkyl; each of $R^4$, $R^5$, $R^6$ and $R^7$ is independently selected H, F, Cl, Br, or I; or a pharmaceutically acceptable salt thereof.

For instance, the compound used for carrying out a method of the invention can be any of compounds 2071, 2073, 2175, 3031, 3033, 3045, 3047, 3049, 3051, 3053, or 3059, or a pharmaceutically acceptable salt thereof.

Figure 4:
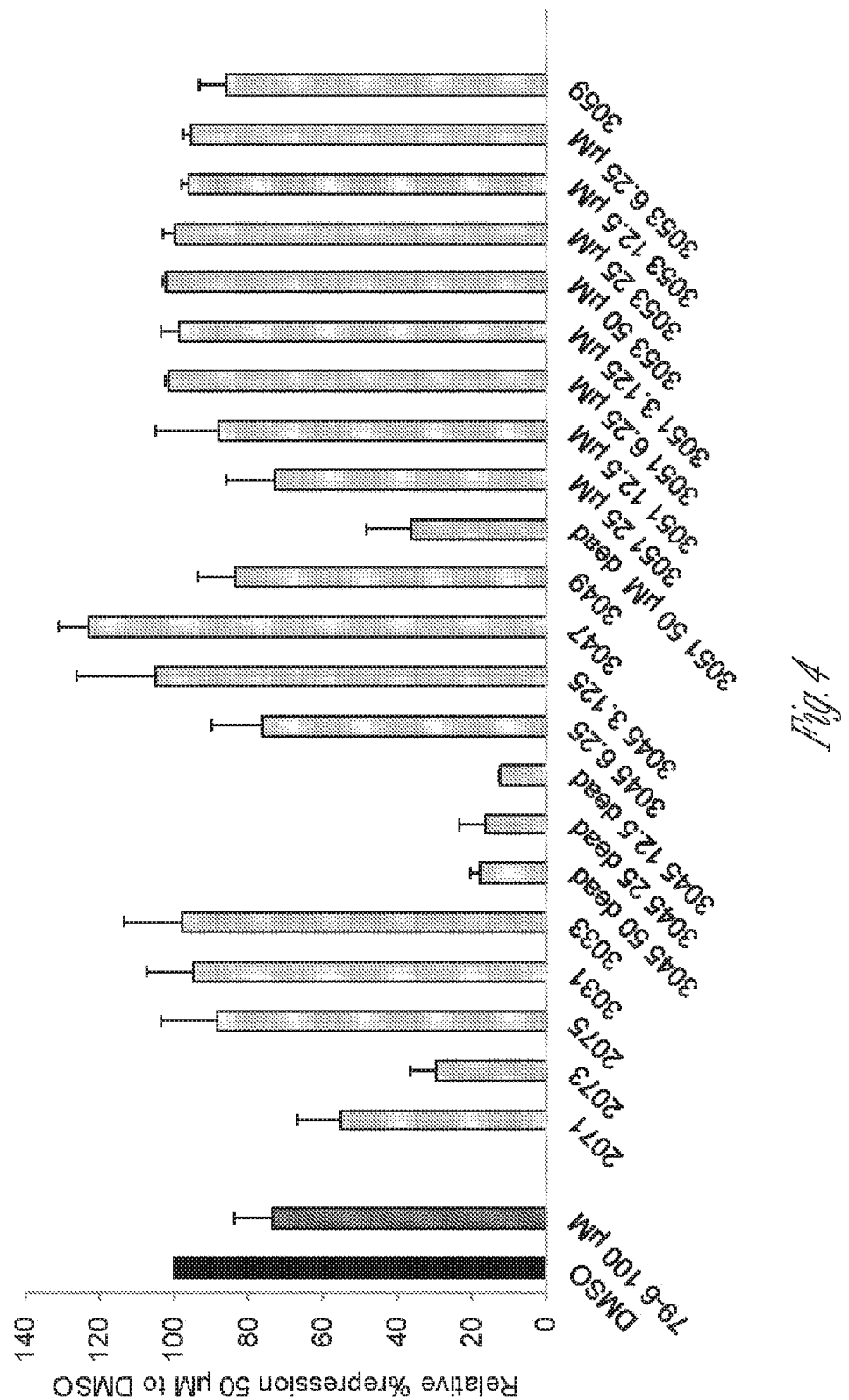
FIG. 4 shows a graph of bioactivities of compounds of the 2071 series analogous to the results shown for FIG. 1.
Figure 5:
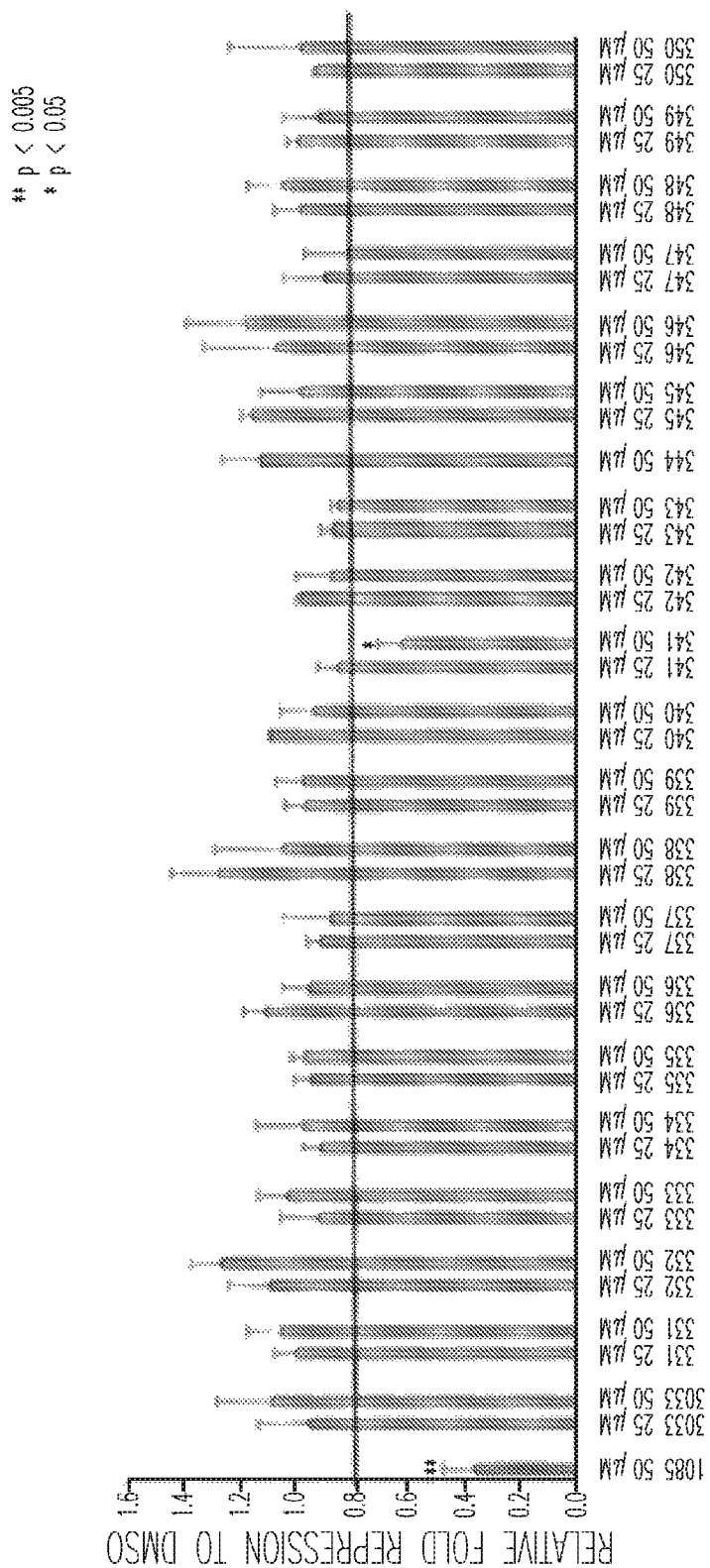
Figure 6A:
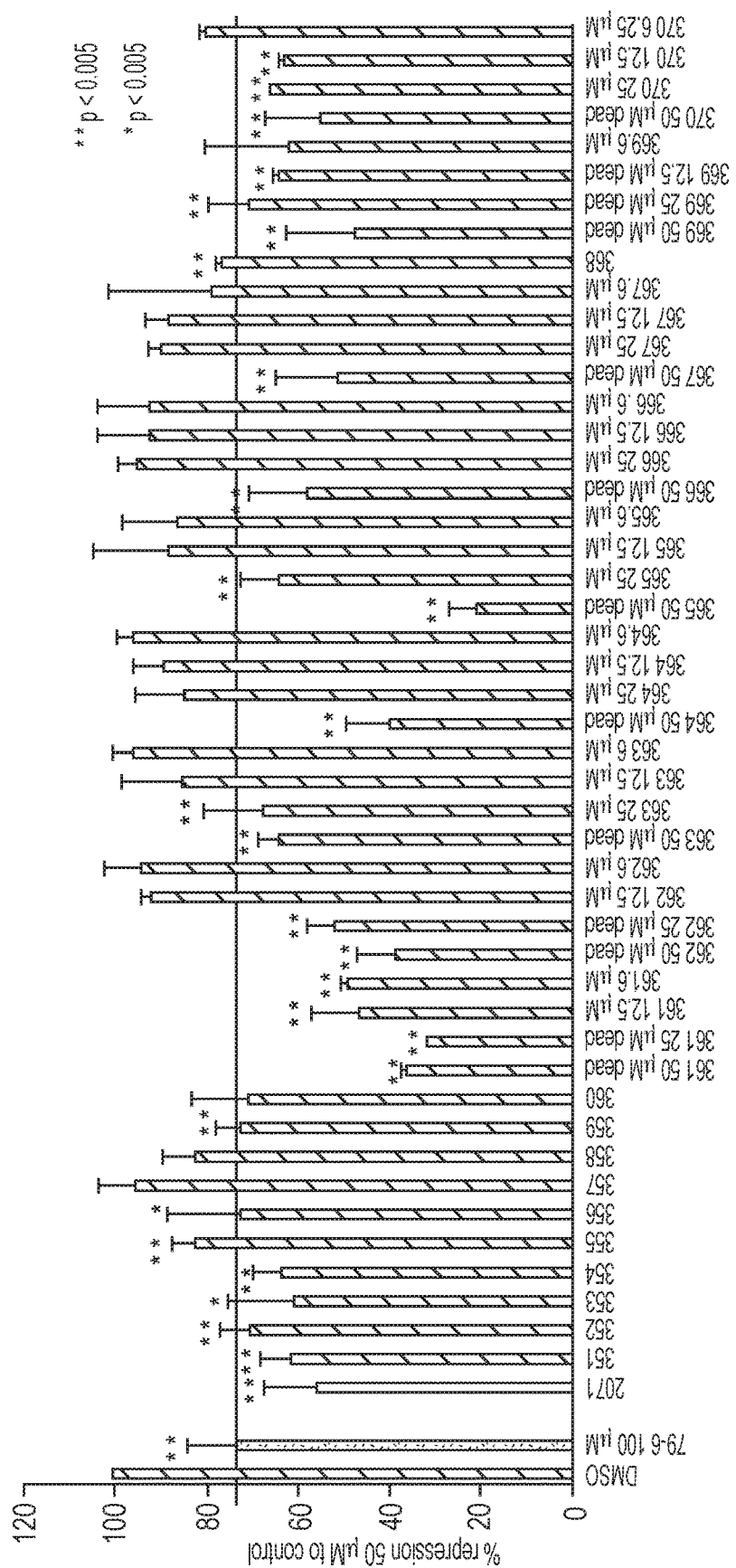
Figure 7A:
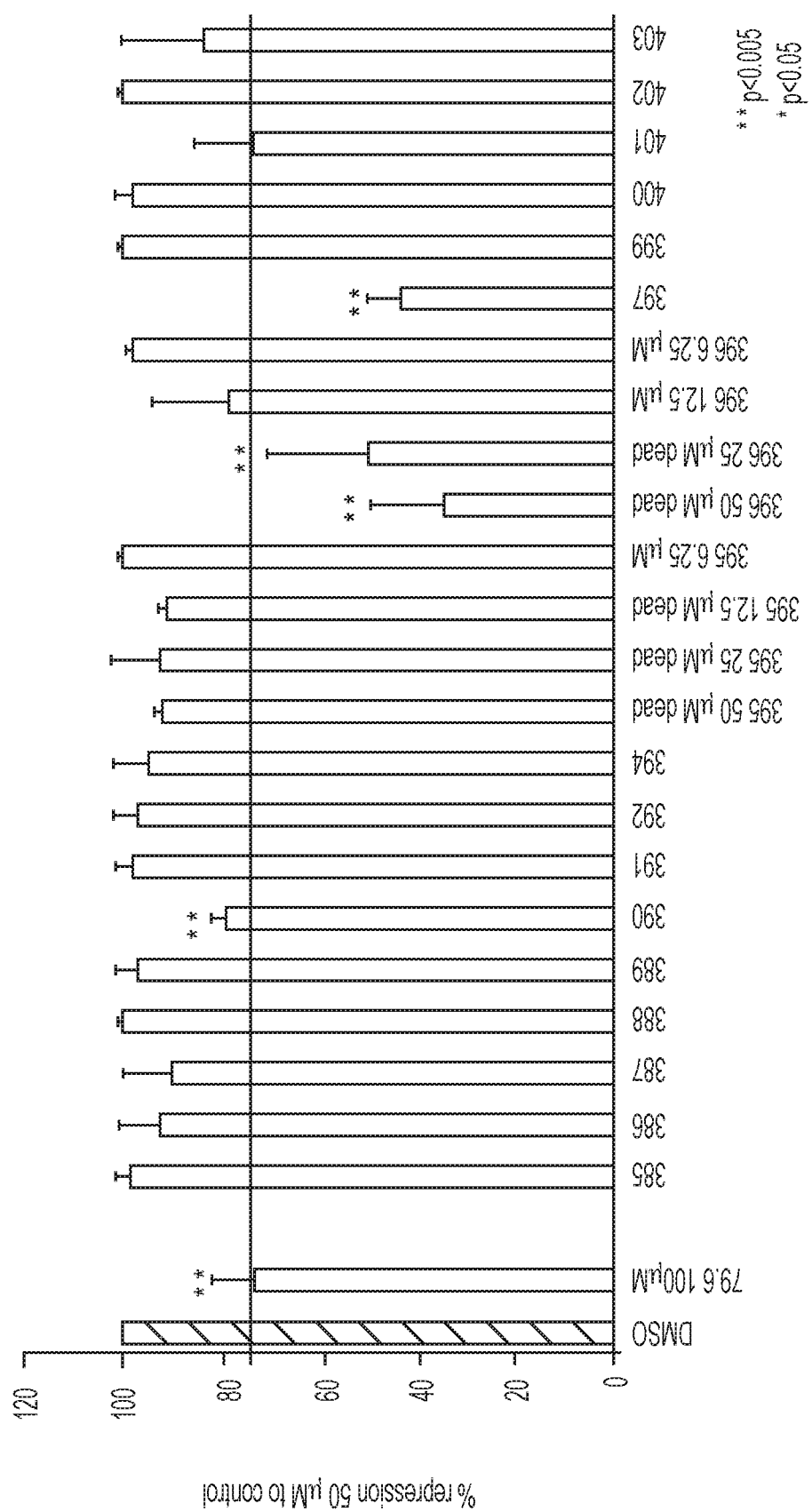
Figure 8A:
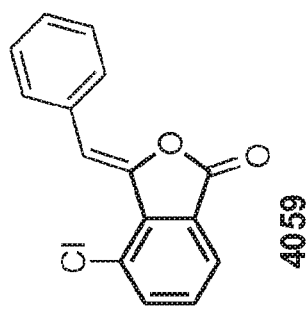
FIGS. 8A and 8B depicts structures and biodata for the 4044 series in comparison with compound 1020.
Figure 8A:
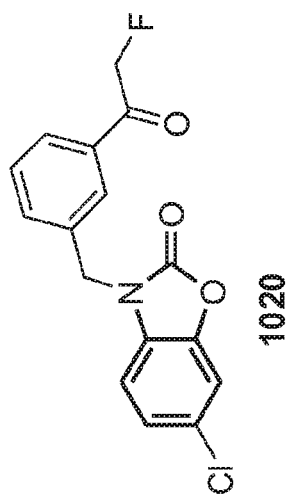
Figure 8A:
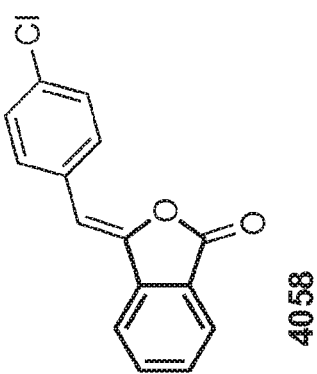
Figure 8A:
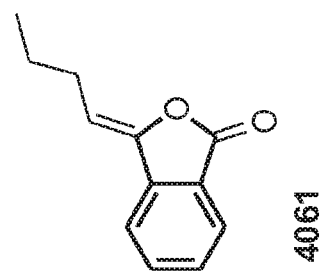
Figure 8A:
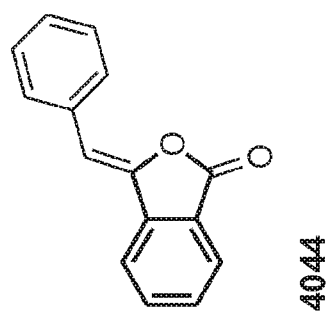
Figure 8A:
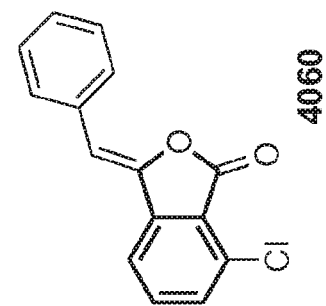
Figure 8B:
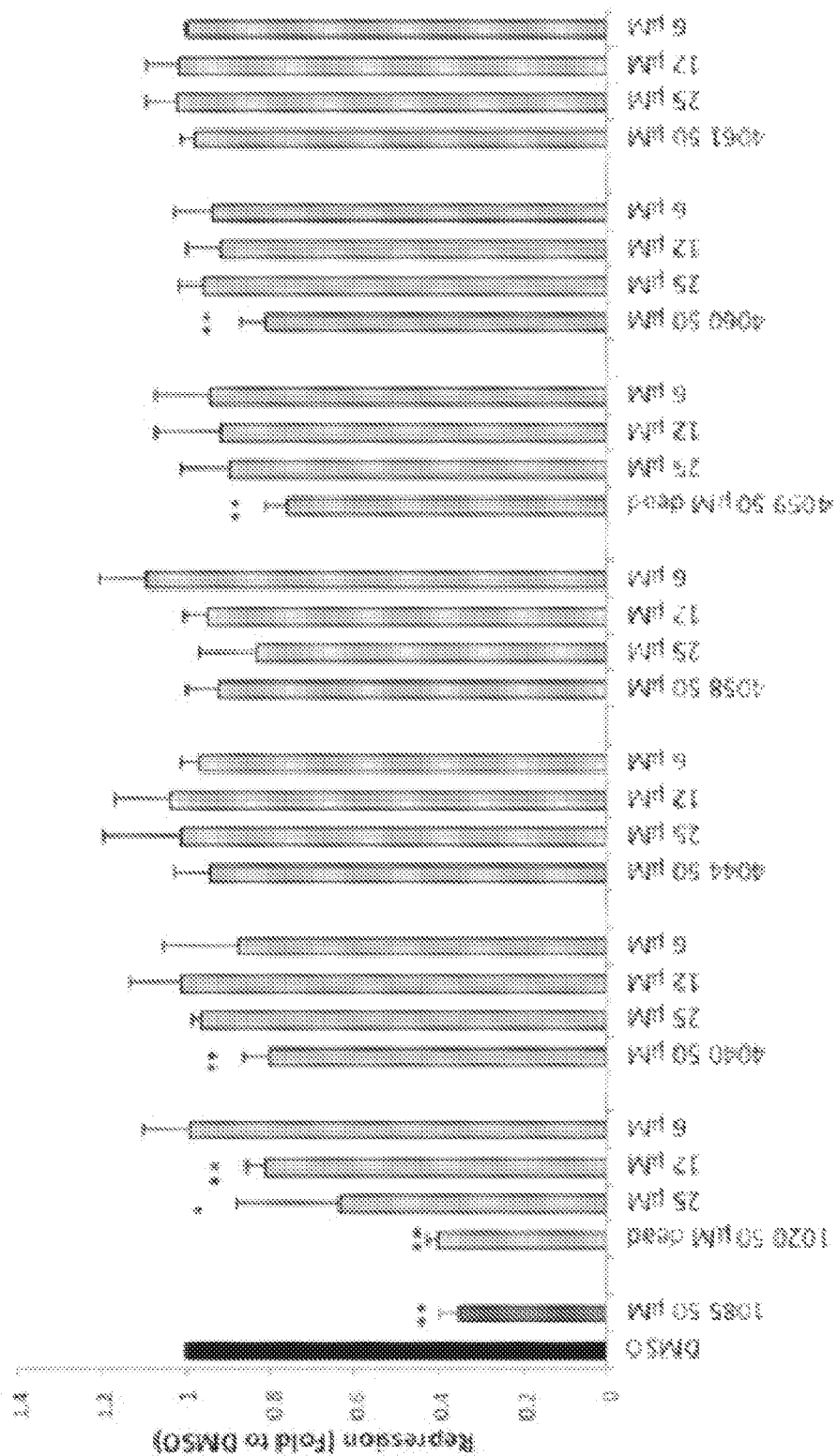

For ease of reference, it is noted that for formula II above, when Z is C=O, the compound is termed the 2071 series, and when Z is O, the compound is termed as belonging to the 3033 series. FIG. 4 shows a graph of bioactivities of compound of the 2071 series analogous to the results shown in FIG. 1 for the 1085 series. FIGS. 5,6, and 7, show graphs of bioactivities of compounds of the 3033 series and some additional compounds of the 1085 and 2071 series, analogous to the results shown in FIG. 1 for the 1085 series.

Accordingly, the invention provides, in various embodiments, a compound of formula II for carrying out a method of disrupting BCL6 BTB domain interactions with corepressors, in B-cells; a method of inhibiting DLBCL tumor growth, or causing DLBCL tumor regression, or both, in a mammal; a method of inhibiting transcriptional repression induced by a complex of BCL6 with SMRT or other corepressor proteins in cancer cells; and, a method of treatment of a patient afflicted with cancer; all comprising administering to the patient an effective dose of a compound of formula II that blocks the BTB lateral groove of BCL6.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

The compounds described herein can be prepared in a number of ways based on the teachings contained in the Synthetic Schemes and Examples provided herein and synthetic procedures known in the art to the ordinary practitioner. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention or for practice of a method of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

It is within ordinary skill to evaluate any compound disclosed and claimed herein for effectiveness in inhibition of BCL6 binding to corepressors and in the various cellular assays using the procedures described above or found in the scientific literature. Accordingly, the person of ordinary skill can prepare and evaluate any of the claimed compounds without undue experimentation.

Any compound found to be an effective inhibitor of BCL6 binding to corepressors can likewise be tested in animal models and in human clinical studies using the skill and experience of the investigator to guide the selection of dosages and treatment regimens.

TABLE 6

Compounds of the 2071/3033 series and others

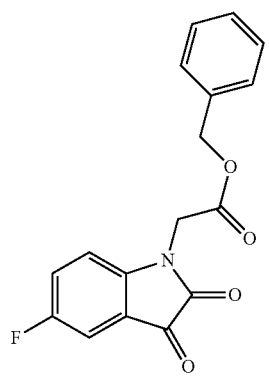 [SMILES: O=C(CN1C(=O)C(=O)c2cc(F)ccc21)OCc1ccccc1]

2073

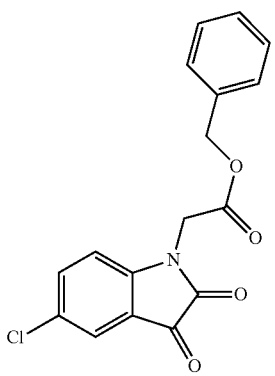

2071

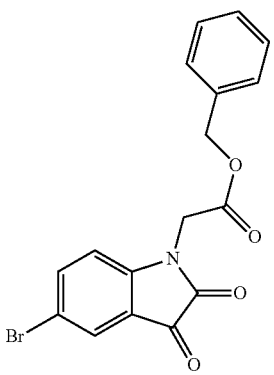 [SMILES: O=C(CN1C(=O)C(=O)c2cc(Cl)ccc21)OCc1ccccc1]

2175

TABLE 6-continued
Compounds of the 2071/3033 series and others
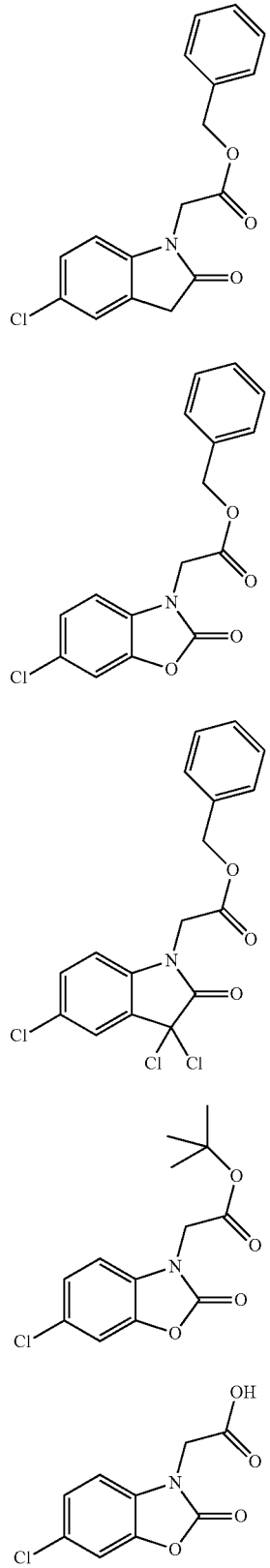
3031
3033
3045
3047
3049
TABLE 6-continued
Compounds of the 2071/3033 series and others
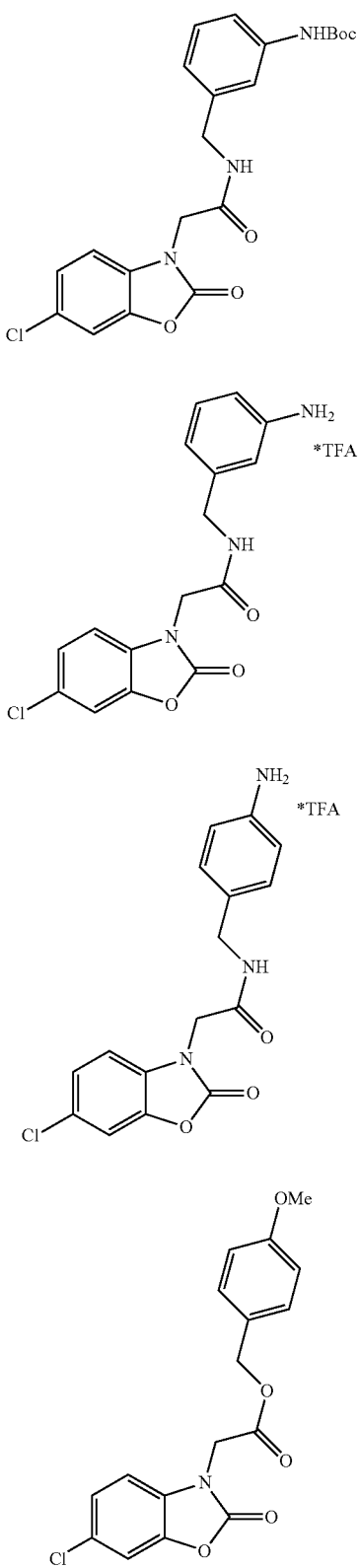
3051
3053
3059
331

TABLE 6-continued
Compounds of the 2071/3033 series and others
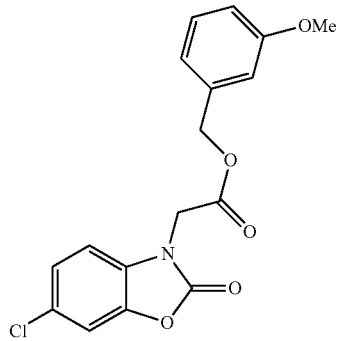 [SMILES: COc1cccc(COC(=O)Cn2c(=O)oc3cc(Cl)ccc32)c1] 332
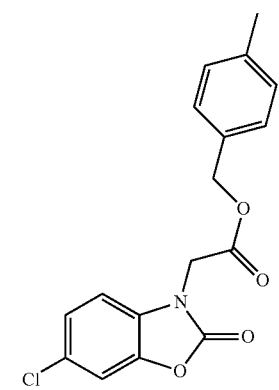 [SMILES: Cc1ccc(COC(=O)Cn2c(=O)oc3cc(Cl)ccc32)cc1] 333
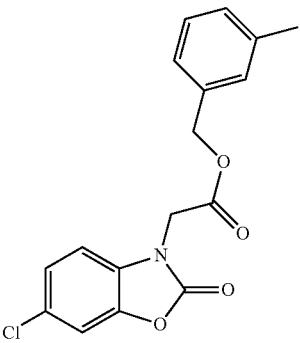 [SMILES: Cc1cccc(COC(=O)Cn2c(=O)oc3cc(Cl)ccc32)c1] 334
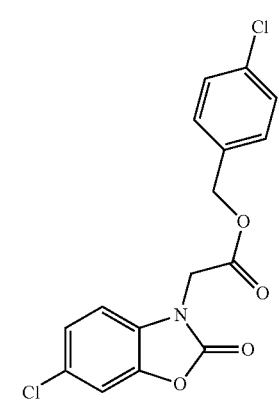 [SMILES: O=C(Cn1c(=O)oc2cc(Cl)ccc21)OCc1ccc(Cl)cc1] 335
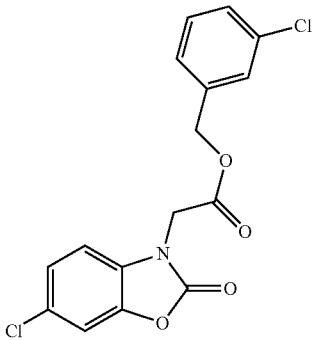 [SMILES: O=C(Cn1c(=O)oc2cc(Cl)ccc21)OCc1cccc(Cl)c1] 336
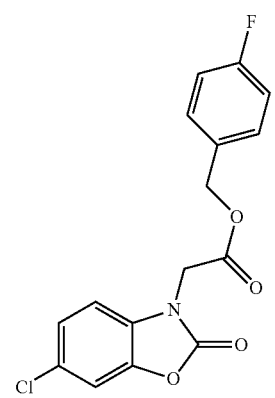 [SMILES: O=C(Cn1c(=O)oc2cc(Cl)ccc21)OCc1ccc(F)cc1] 337
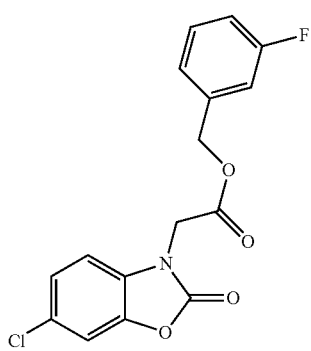 [SMILES: O=C(Cn1c(=O)oc2cc(Cl)ccc21)OCc1cccc(F)c1] 338
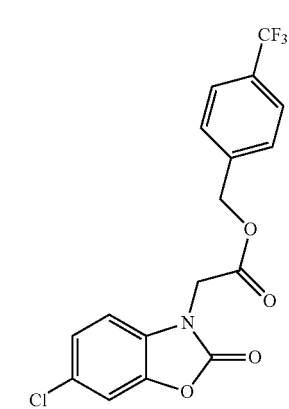 [SMILES: O=C(Cn1c(=O)oc2cc(Cl)ccc21)OCc1ccc(C(F)(F)F)cc1] 339

TABLE 6-continued
Compounds of the 2071/3033 series and others
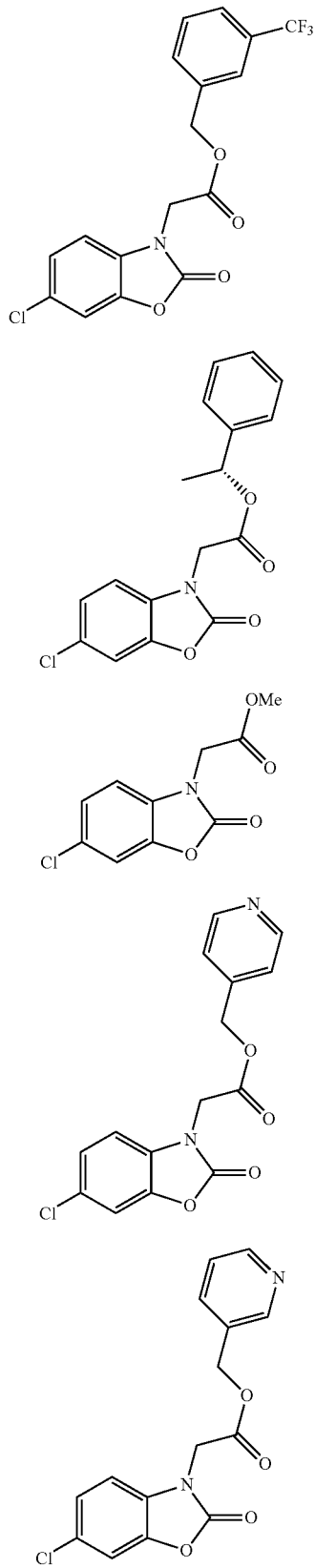
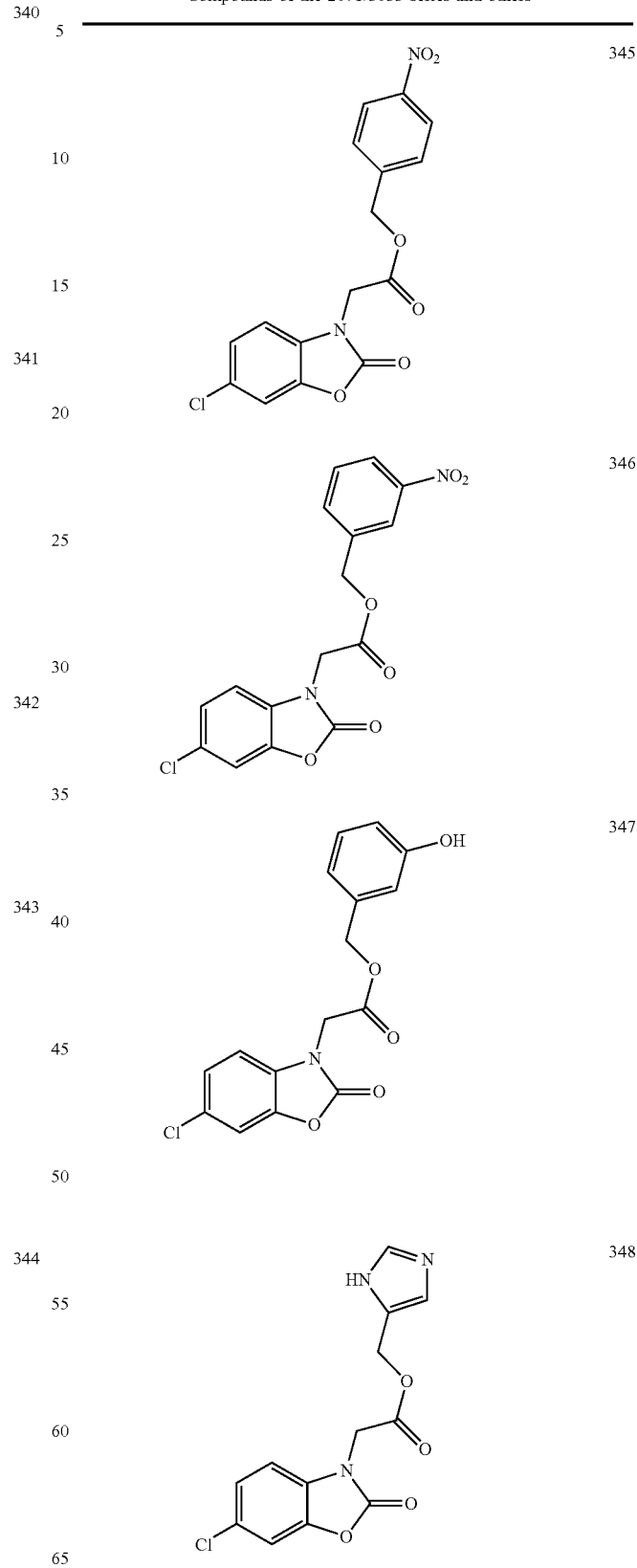

TABLE 6-continued
Compounds of the 2071/3033 series and others
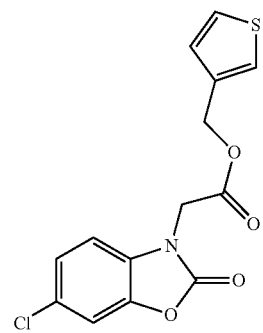 [SMILES: O=C(Cn1c(=O)oc2cc(Cl)ccc21)OCc1ccsc1] 349
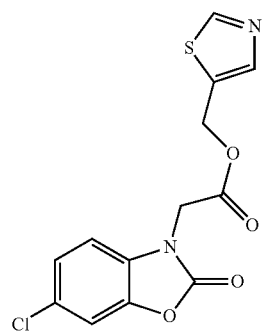 [SMILES: O=C(Cn1c(=O)oc2cc(Cl)ccc21)OCc1cncs1] 350
3033
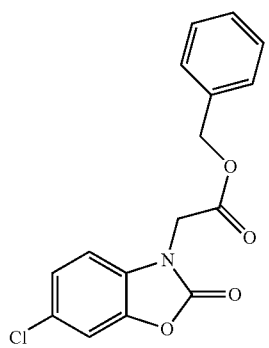 [SMILES: O=C(Cn1c(=O)oc2cc(Cl)ccc21)OCc1ccccc1]
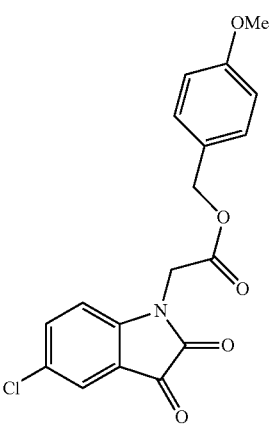 [SMILES: COc1ccc(COC(=O)CN2C(=O)C(=O)c3cc(Cl)ccc32)cc1] 351
TABLE 6-continued
Compounds of the 2071/3033 series and others
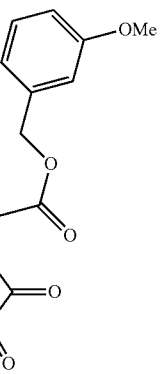 352
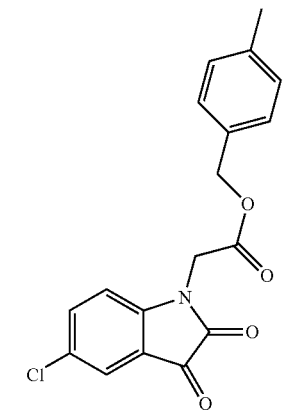 [SMILES: Cc1ccc(COC(=O)CN2C(=O)C(=O)c3cc(Cl)ccc32)cc1] 353
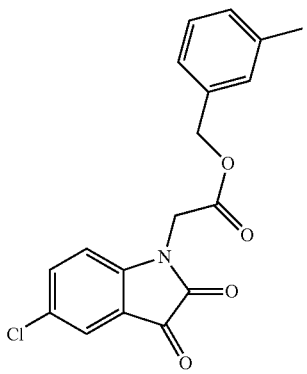 [SMILES: Cc1cccc(COC(=O)CN2C(=O)C(=O)c3cc(Cl)ccc32)c1] 354
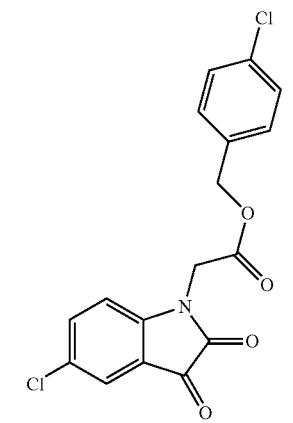 [SMILES: O=C(CN1C(=O)C(=O)c2cc(Cl)ccc21)OCc1ccc(Cl)cc1] 355

TABLE 6-continued
Compounds of the 2071/3033 series and others
356
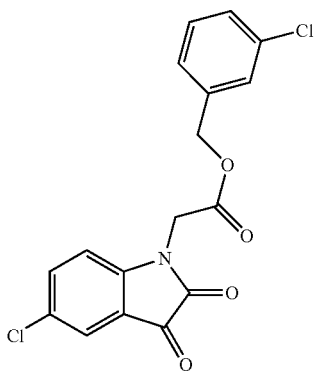 [SMILES: O=C(CN1C(=O)C(=O)c2cc(Cl)ccc21)OCc1cccc(Cl)c1]
357
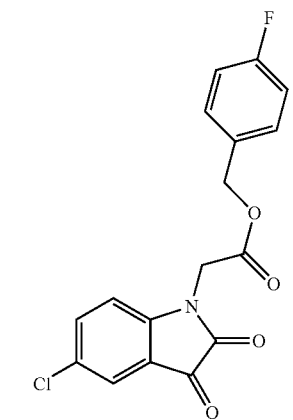 [SMILES: O=C(CN1C(=O)C(=O)c2cc(Cl)ccc21)OCc1ccc(F)cc1]
358
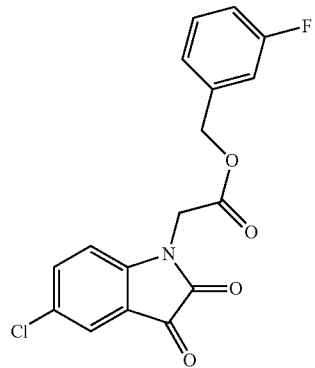 [SMILES: O=C(CN1C(=O)C(=O)c2cc(Cl)ccc21)OCc1cccc(F)c1]
359
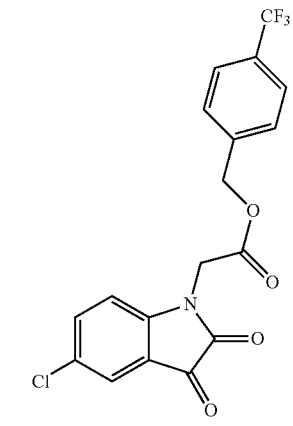 [SMILES: O=C(CN1C(=O)C(=O)c2cc(Cl)ccc21)OCc1ccc(C(F)(F)F)cc1]
TABLE 6-continued
Compounds of the 2071/3033 series and others
360
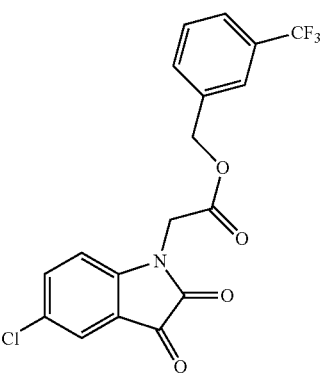 [SMILES: O=C(CN1C(=O)C(=O)c2cc(Cl)ccc21)OCc1cccc(C(F)(F)F)c1]
361
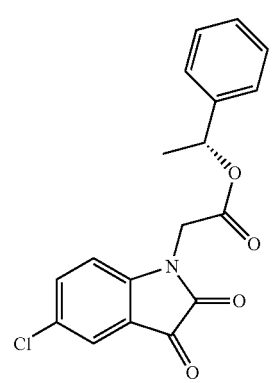 [SMILES: C[C@@H](OC(=O)CN1C(=O)C(=O)c2cc(Cl)ccc21)c1ccccc1]
362
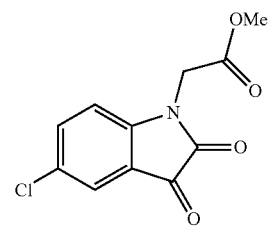 [SMILES: COC(=O)CN1C(=O)C(=O)c2cc(Cl)ccc21]
363
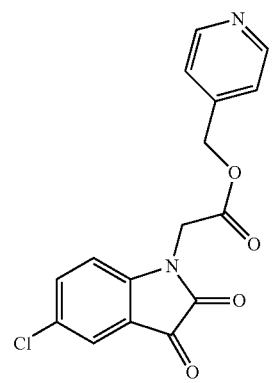 [SMILES: O=C(CN1C(=O)C(=O)c2cc(Cl)ccc21)OCc1ccncc1]

TABLE 6-continued

Compounds of the 2071/3033 series and others

| # | Structure |
|---|---|
| 364 | 5-Cl-isatin N-CH2-C(O)O-CH2-(3-pyridyl) |
| 365 | 5-Cl-isatin N-CH2-C(O)O-CH2-(4-nitrophenyl) |
| 366 | 5-Cl-isatin N-CH2-C(O)O-CH2-(3-nitrophenyl) |
| 367 | 5-Cl-isatin N-CH2-C(O)O-CH2-(3-thienyl) |
| 368 | 5-Cl-isatin N-CH2-CO2H |
| 369 | 5-Cl-isatin N-CH2-phenyl |
| 370 | 5-Cl-isatin N-CH2-C≡CH |
| 2077 | 5-Cl-isatin N-CH2-C(O)O-CH2-phenyl |
| 385 | 5-Cl-benzimidazol-2-one N-CH2-CO2H |
| 386 | 5-Cl-benzimidazol-2-one N-CH2-CO2H |
| 387 | 5-Cl-benzimidazol-2-one N-CH2-CO2H |

TABLE 6-continued
Compounds of the 2071/3033 series and others
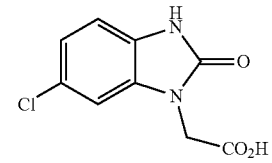 [SMILES: O=C(O)Cn1c(=O)[nH]c2ccc(Cl)cc21] 388
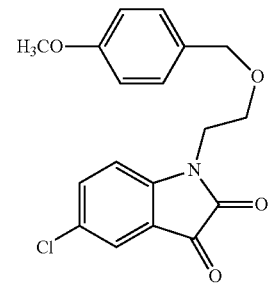 [SMILES: COc1ccc(COCCN2C(=O)C(=O)c3cc(Cl)ccc32)cc1] 389
 390
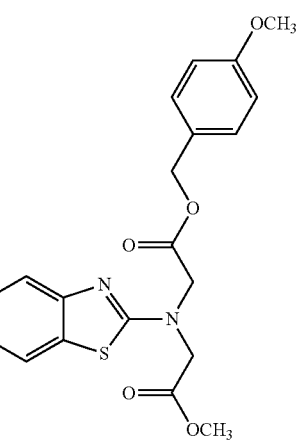 391
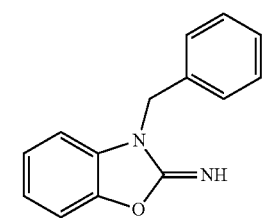 [SMILES: N=c1oc2ccccc2n1Cc1ccccc1] 392
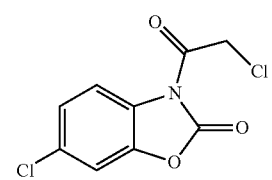 [SMILES: O=C(CCl)n1c(=O)oc2cc(Cl)ccc21] 394
TABLE 6-continued
Compounds of the 2071/3033 series and others
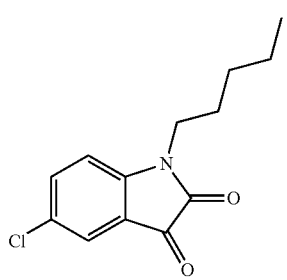 [SMILES: CCCCCN1C(=O)C(=O)c2cc(Cl)ccc21] 395
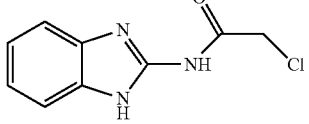 396
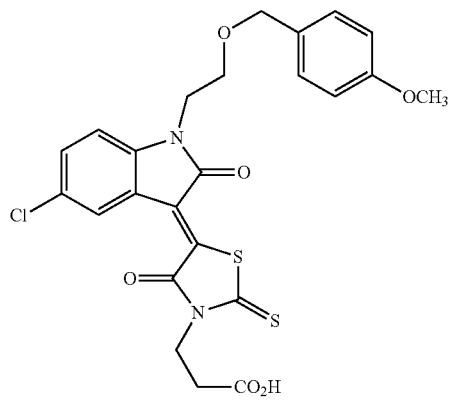 [SMILES: COc1ccc(COCCN2C(=O)/C(=C3\SC(=S)N(CCC(=O)O)C3=O)c3cc(Cl)ccc32)cc1] 397
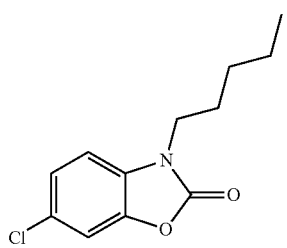 [SMILES: CCCCCn1c(=O)oc2cc(Cl)ccc21] 399
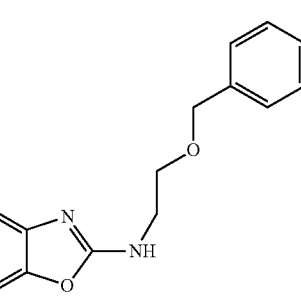 400

TABLE 6-continued

Compounds of the 2071/3033 series and others

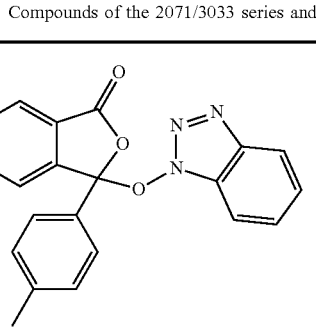

401

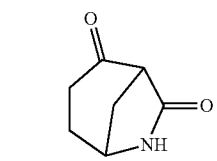

402

TABLE 7

| Compound | Kd (μM) | BCL6 independent GI$_{50}$ Toledo (μM) | BCL6 dependent GI$_{50}$ Ly7 (μM) | GI$_{50}$ SUDHL6 (μM) |
|---|---|---|---|---|
| 2071 | NB | >125 | 53 | 35 |
| 2073 | NB | 40 | 30 | 30 |

TABLE 8

| | Cell line | | | | | |
|---|---|---|---|---|---|---|
| | Bcl-6 dependent | | | Bcl-6 independent | | |
| | Ly3 | Ly7 | SUDH6 | Karpas 422 | Toledo | WSU-DLCL2 |
| Compound | | | GI$_{50}$ (μM) | | | |
| 2071 | >40 | 26 ± 1 | 10 ± 1 | >40 | >40 | >40 |
| 2073 | >40 | 36 ± 7 | 17 ± 1 | >40 | >40 | >40 |
| 2075 | >40 | 4.4 ± 0.7 | 14 ± 8 | >40 | >40 | >40 |
| 2097 | >30 | >30 | >30 | >30 | >30 | >30 |
| 2099 | >30 | >30 | >30 | >30 | >30 | >30 |
| 2101 | >30 | >30 | >30 | >30 | >30 | >30 |

TABLE 9

| | Bcl6 dependent | | | | Bcl6 independent | | | | |
|---|---|---|---|---|---|---|---|---|---|
| | | | | GI 50 (μM) | | | | | |
| | Ly3 | Ly1 | Ly10 | SUDHL6 | Ly7 | Toledo | K422 | WSUDLCL2 | Ly4 | Ly1B50 |
| 355 | 54 | 37 | 62 | 1 | 45 | 35 | 38 | 52 | 81 | 55 |
| 357 | 79 | 81 | 60 | 1 | 25 | 51 | 58 | 100 | >125 | 56 |
| 358 | >125 | >125 | >125 | 2 | 20 | 69 | >125 | >125 | >125 | >125 |
| 361 | 56 | 24 | 166 | 7 | 26 | 39 | 20 | 41 | 98 | 103 |

TABLE 6-continued

Compounds of the 2071/3033 series and others

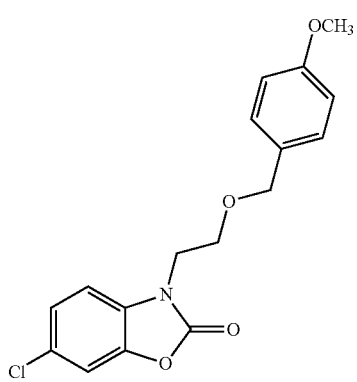 [SMILES: COc1ccc(COCCn2c(=O)oc3cc(Cl)ccc32)cc1]

403

TABLE 10

| Compound | Kd (μM) | BCL6 independent GI$_{50}$ Toledo (μM) | BCL6 dependent GI$_{50}$ Ly7 (μM) | GI$_{50}$ SUDHL6 (μM) |
|---|---|---|---|---|
| 333 | NB | >125 | >125 | >125 |
| 334 | NB | >125 | >125 | >125 |
| 339 | NB | >125 | >125 | >125 |
| 341 | NB | >125 | >125 | >125 |
| 355 | NB | 45 ± 7 | 43 ± 3 | 42 ± 10 |
| 357 | NB | 50 ± 1 | 30 ± 10 | 22 ± 3 |
| 358 | NB | 82 ± 20 | 40 ± 10 | 27 ± 4 |
| 367 | 324 ± 34 | 53 ± 10 | 22 ± 4 | 15 ± 7 |

Tables 7 and 8 show the effects of compounds of the 2071 series on BCL6 dependent and independent cell lines, and Tables 9 and 10 provide analogous data for compounds of the 3033 series.

Figure 9A:
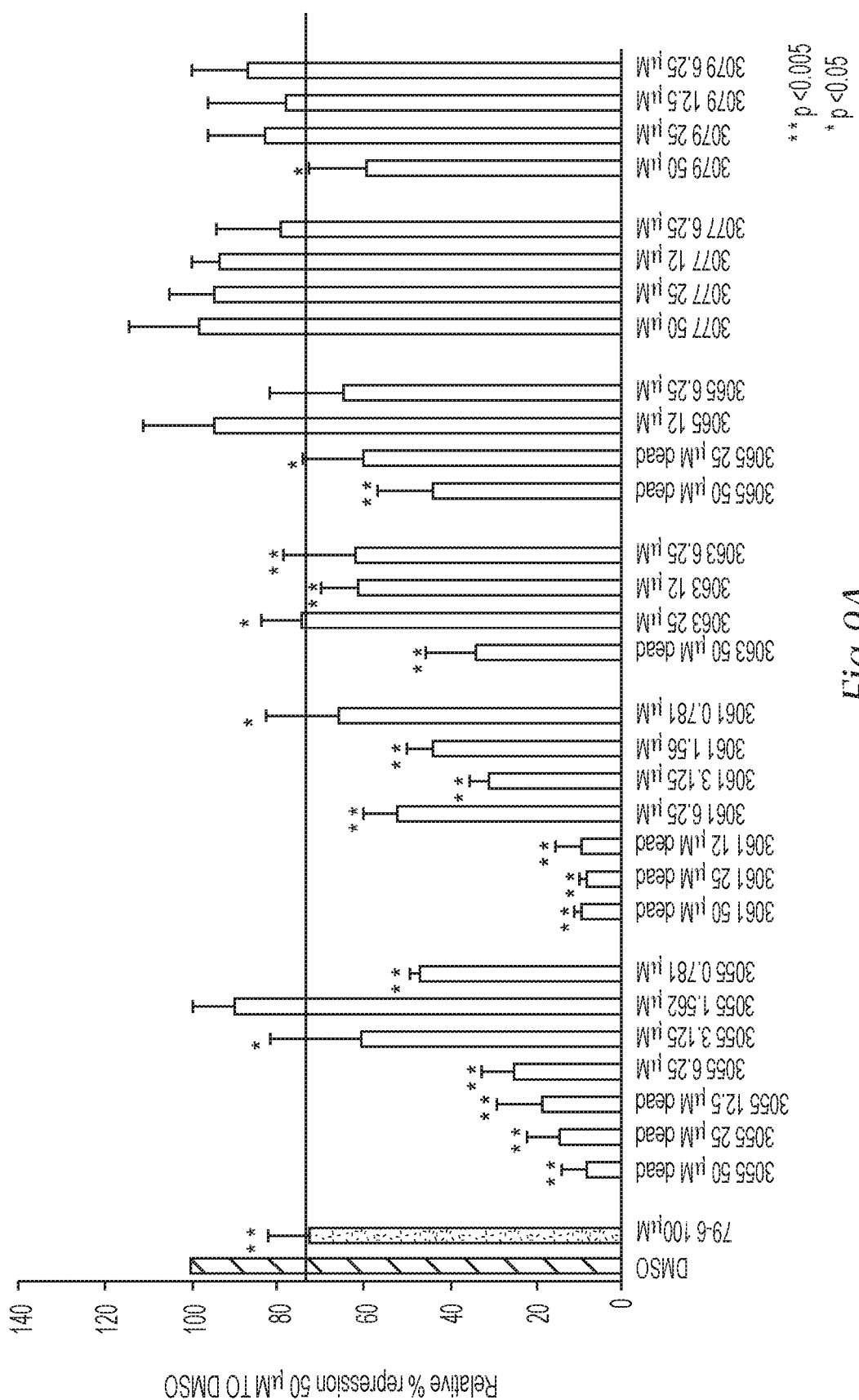

Ligand design next focused on linking a bicyclic aromatic system that binds in the aromatic site with a moiety that interacts irreversibly with the HDCH site. Compounds were designed that include reactive moieties targeting Cys53 on the HDCH site, with the goal of developing of BCL6-specific irreversible inhibitors (compounds 3065, 3061, 3079, 3063, 3055 and 3077, termed the 3055 series). Examples of such irreversible inhibitors are shown in Table 11. Biodata are provided in graphical form in FIG. 9.

TABLE 11

Compounds of the 3055 series: irreversible inhibitors

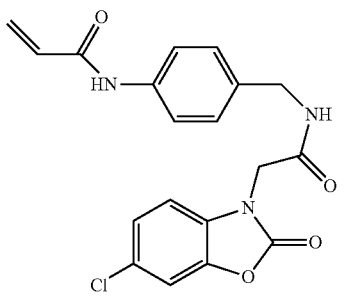 [SMILES: C=CC(=O)Nc1ccc(CNC(=O)Cn2c(=O)oc3cc(Cl)ccc32)cc1]
3066

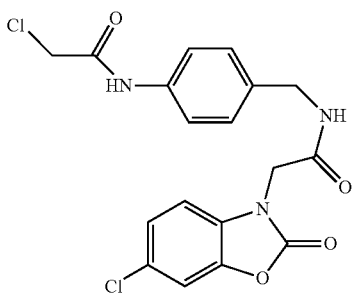 [SMILES: O=C(Cn1c(=O)oc2cc(Cl)ccc21)NCc1ccc(NC(=O)CCl)cc1]
3061

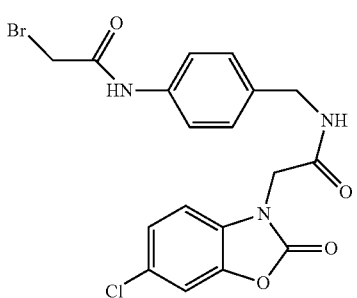
3079

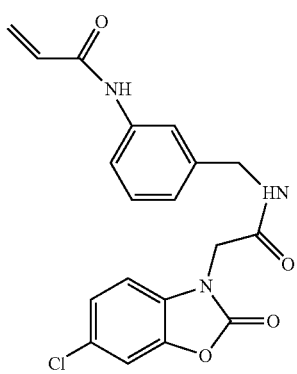 [SMILES: C=CC(=O)Nc1cccc(CNC(=O)Cn2c(=O)oc3cc(Cl)ccc32)c1]
3063

TABLE 11-continued

Compounds of the 3055 series: irreversible inhibitors

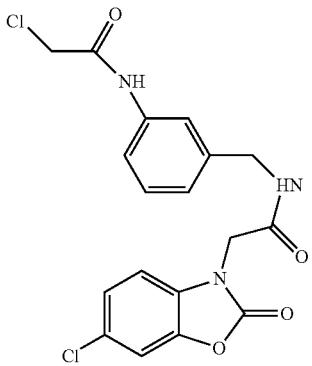 [SMILES: O=C(Cn1c(=O)oc2cc(Cl)ccc21)NCc1cccc(NC(=O)CCl)c1]
3055

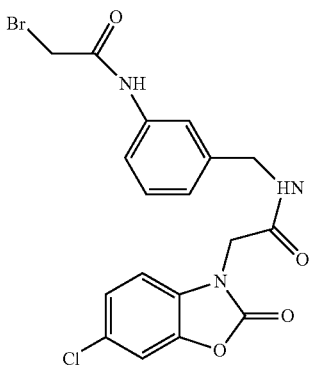
3077

Figure 10:
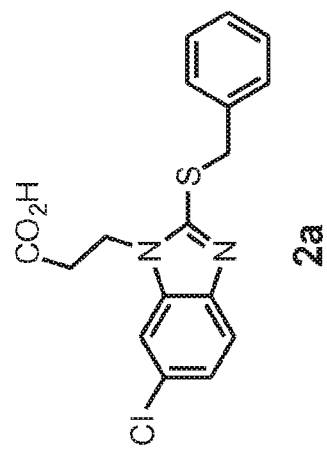
FIG. 10 shows structural and computational data related to compounds of Scaffold 2.
Figure 10:
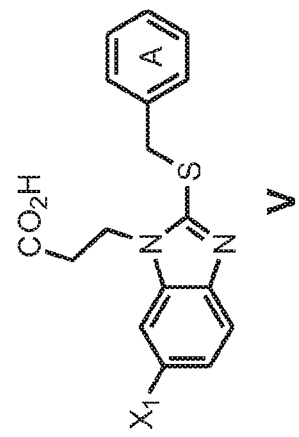

FIG. 10 depicts structural information and computational data for a compound of Scaffold 2, designed to target both the aromatic and arene sites, the compounds of Scaffold 2 being of formula (V)

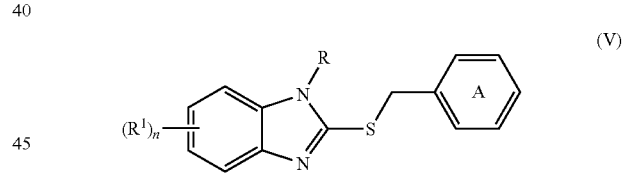
(V)

wherein the ring labeled A is a substituted or unsubstituted aryl or heteroaryl ring, R is H or is $(CH_2)_m CO_2 H$; m=1, 2, or 3; each $R^1$ is independently selected halo, (C1-C6)alkyl, (C1-C6)alkoxy, nitro, or trifluoromethyl; n=0, 1, 2, or 3; or a pharmaceutically acceptable salt thereof.

Figure 11A:
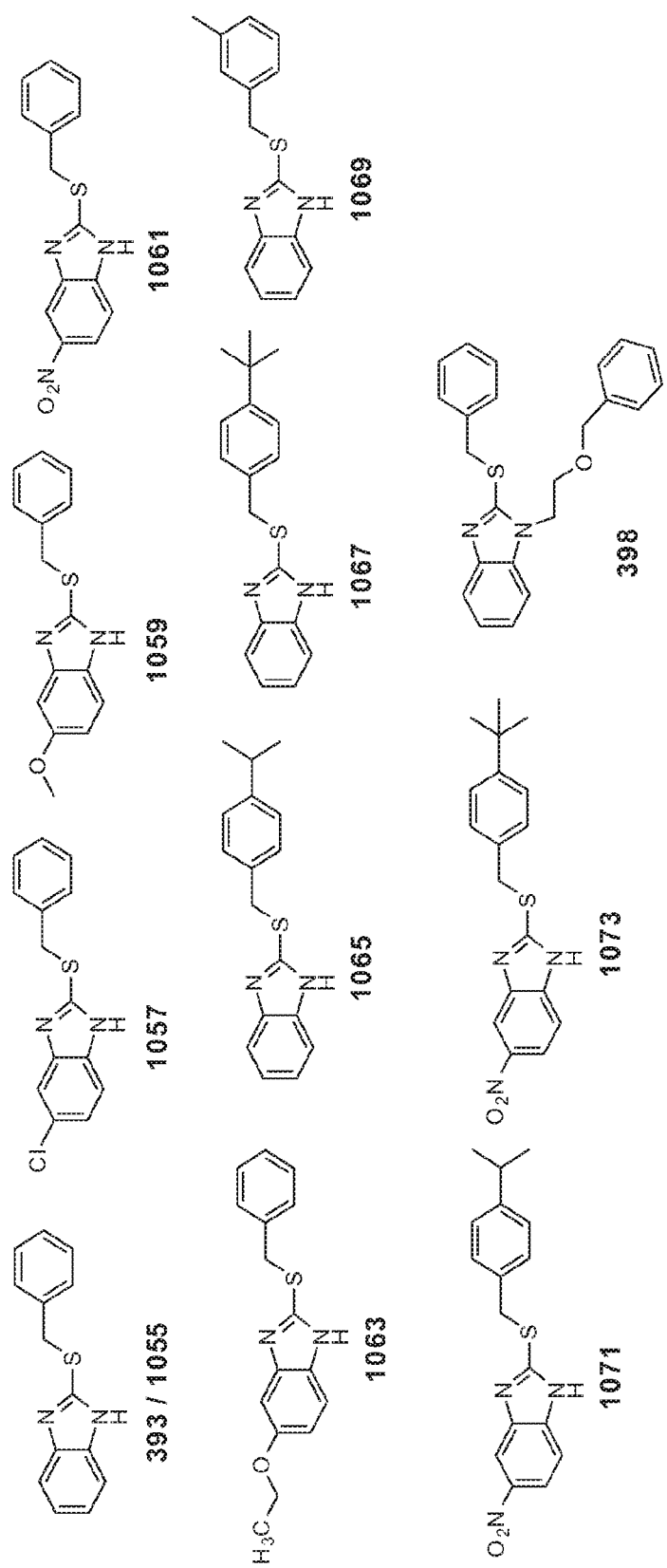
FIGS. 11A, 11B and 11C depicts structures and biodata for additional compounds of Scaffold 2.
Figure 11B:
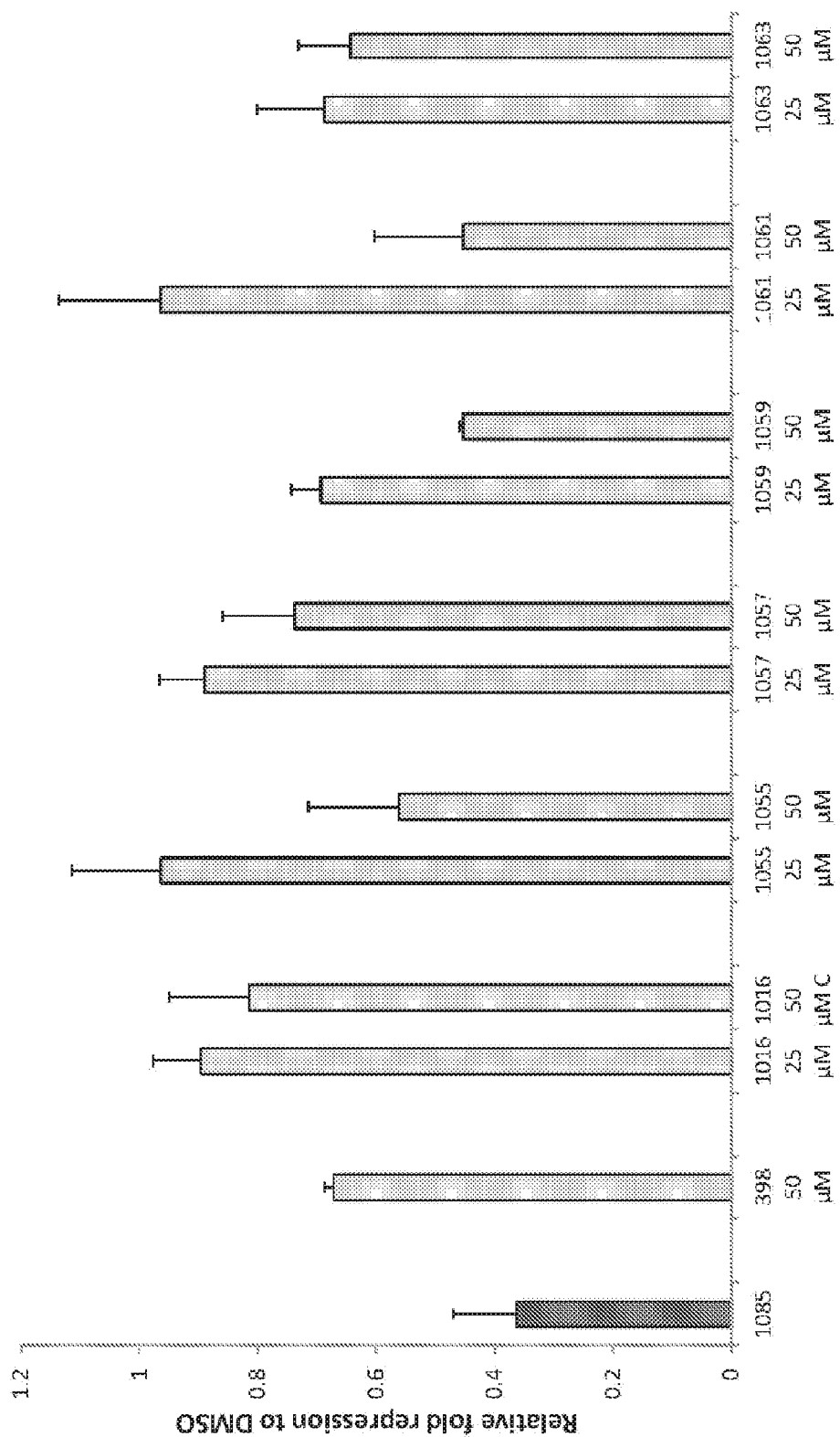
Figure 11C:
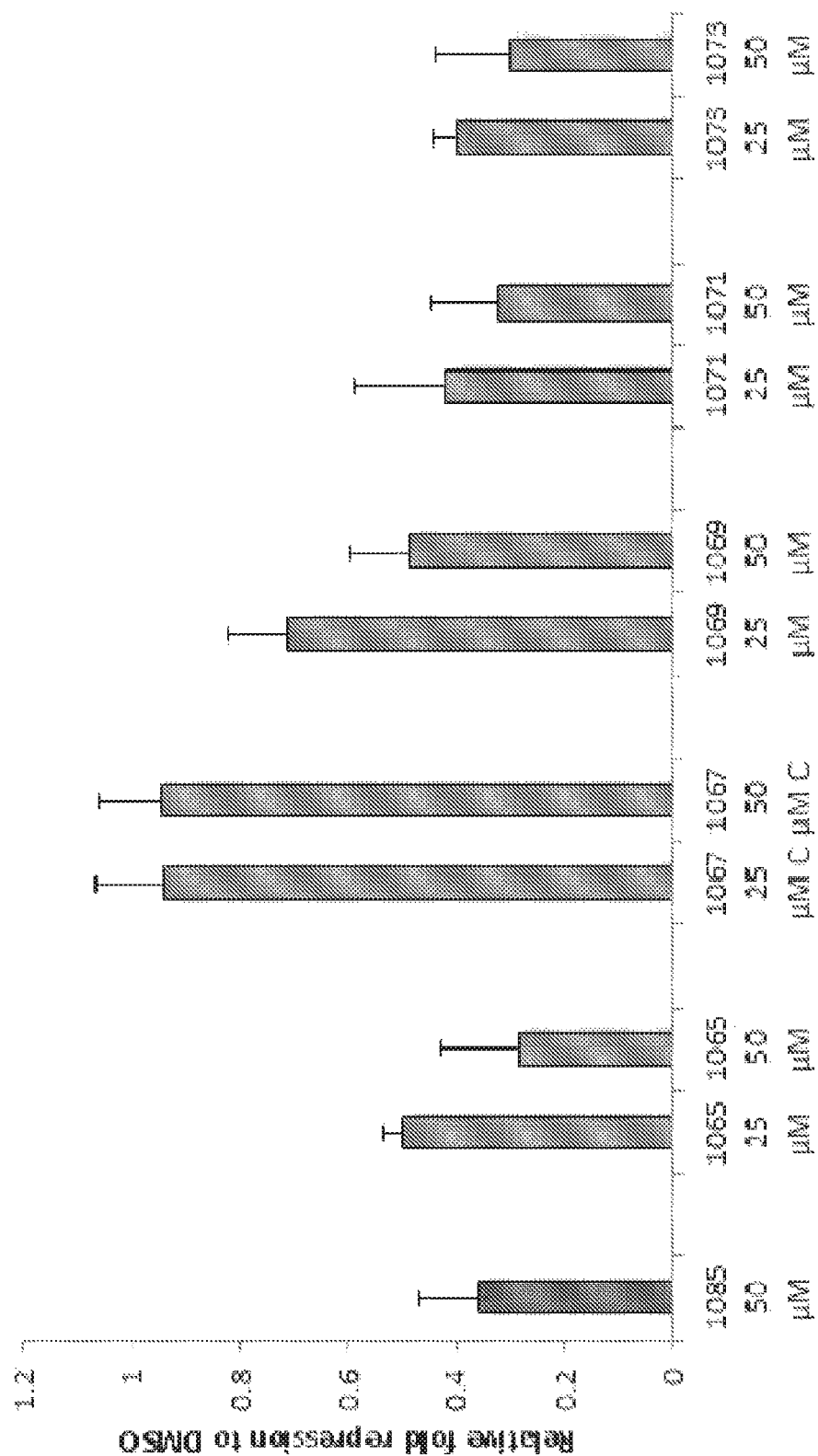

Table 12 presents exemplary structures and Table 13 present biodata for selected representatives of compounds of Scaffold 2. Representative structures are shown in FIG. 11(A) and biodata are provided in FIGS. 11(B) and 11(C).

TABLE 12

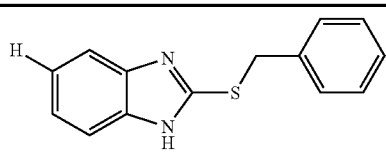
1055

TABLE 12-continued

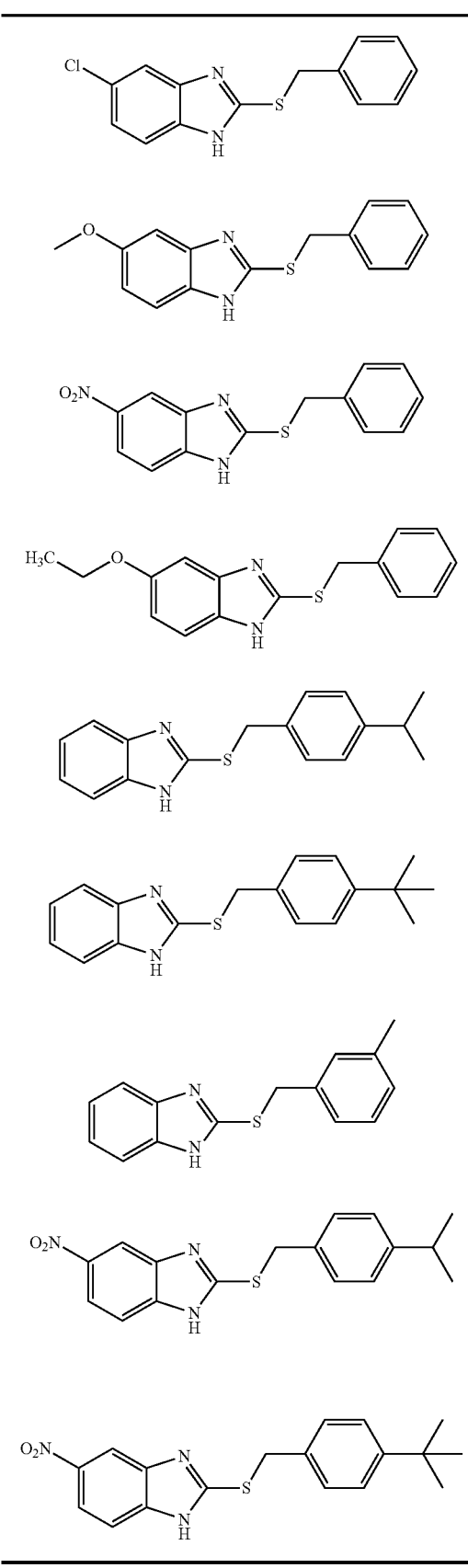

| | |
|---|---|
| 1057 | |
| 1059 | |
| 1061 | |
| 1063 | |
| 1065 | |
| 1067 | |
| 1069 | |
| 1071 | |
| 1073 | |

TABLE 13

| Compound | Kd (µM) | BCL6 independent GI$_{50}$ Toledo (µM) | BCL6 dependent GI$_{50}$ Ly7 (µM) | GI$_{50}$ SUDHL6 (µM) |
|---|---|---|---|---|
| 393 | 174 ± 25 | >125 | >125 | >125 |
| 1057 | 87 ± 12 | >125 | >125 | >125 |
| 1059 | NB | >125 | >125 | >125 |
| 1061 | 180 ± 36 | >125 | 60 | 40 ± 10 |
| 1063 | 315 ± 24 | >125 | >125 | >125 |

Compounds of formula V can be prepared according to synthetic scheme 3, below.

Figure 12:
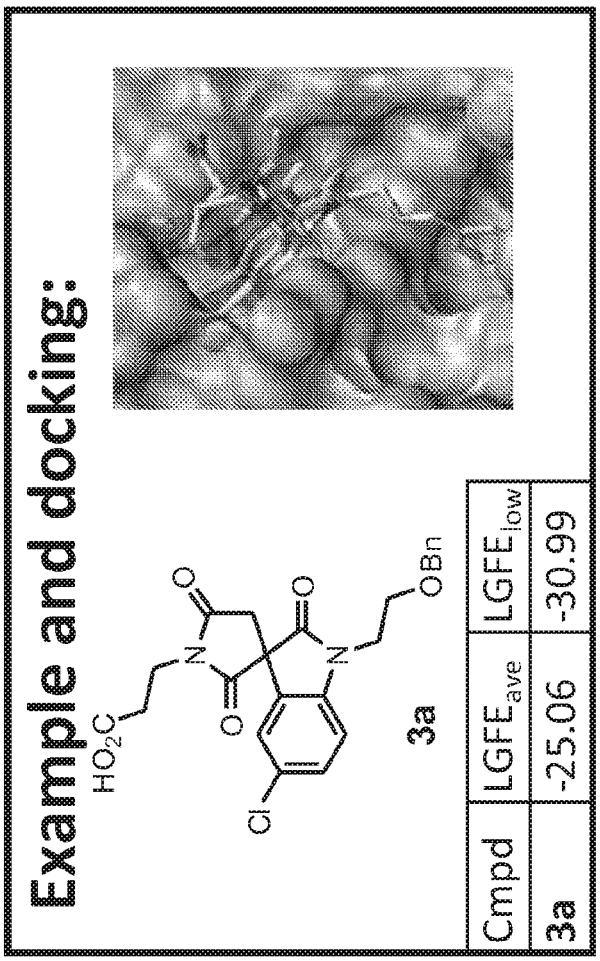
FIG. 12 shows structural and computational data for Scaffold 3.
Figure 12:
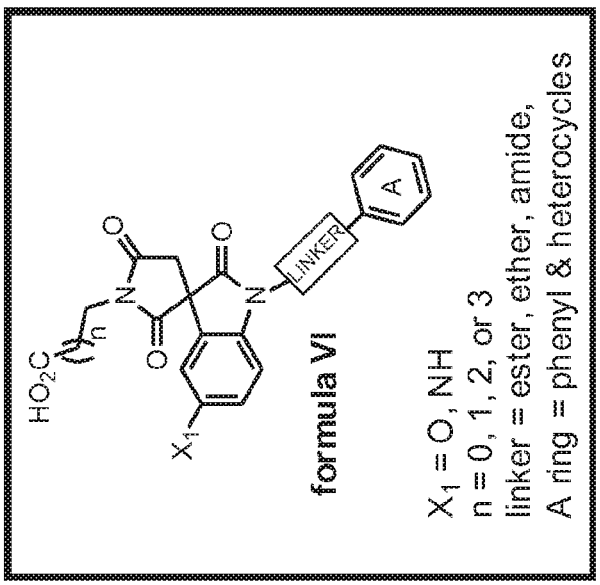

FIG. 12 depicts structural information and computational data for a compound of Scaffold 3 of formula VI

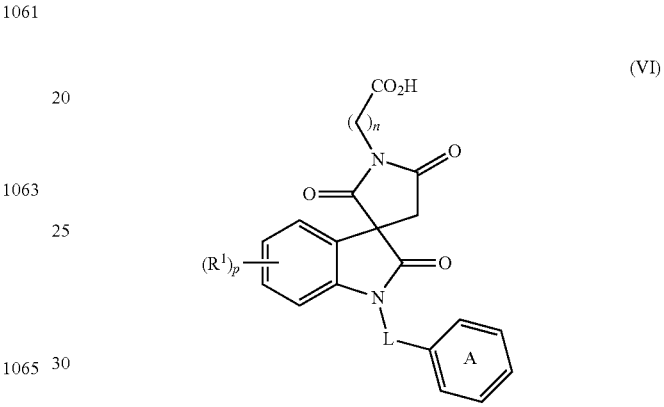

(VI)

wherein the ring labeled A is a substituted or unsubstituted aryl or heteroaryl ring, each $R^1$ is independently selected halo, (C1-C6)alkyl, (C1-C6)alkoxy, nitro, or trifluoromethyl; n=1, 2, or 3; p=0, 1, 2, or 3; L is a linker comprising an alkyl chain optionally comprising one or more ether oxygen atom, ester group, or amide group; or a pharmaceutically acceptable salt thereof.

Compounds of formula VI can be prepared according to Synthetic Scheme 4, below. A "linker", as the term is used herein, refers to a bifunctional chain bonded at each end to the ring labeled A and to the oxindole nitrogen atom, respectively. A linker can be an alkyl chain, optionally comprising ether oxygens atoms, ester groups, amide groups, and the like.

Figure 13:
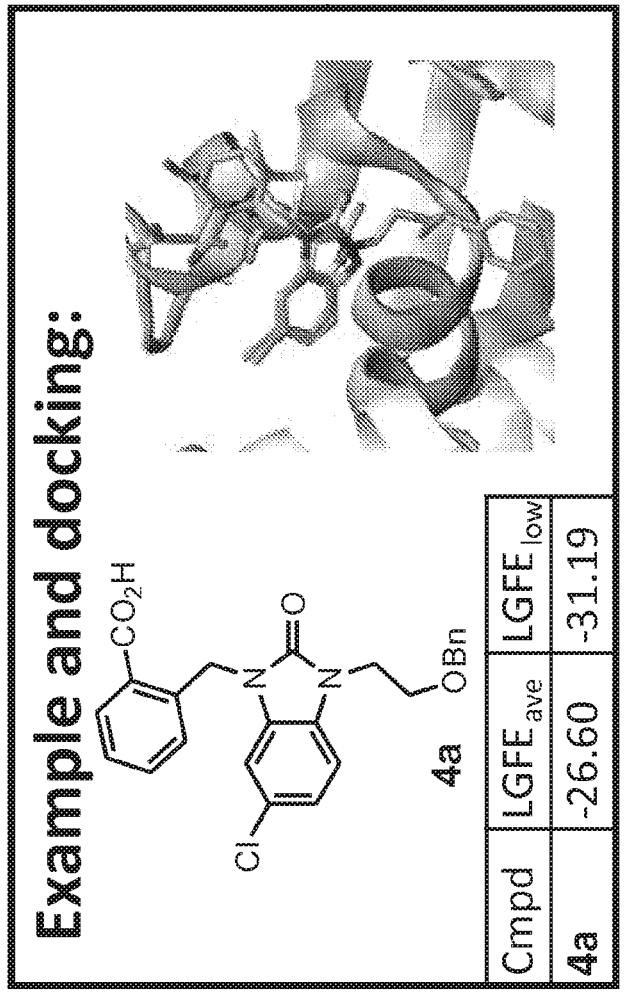
FIG. 13 shows structural and computational data for Scaffold 4.
Figure 13:
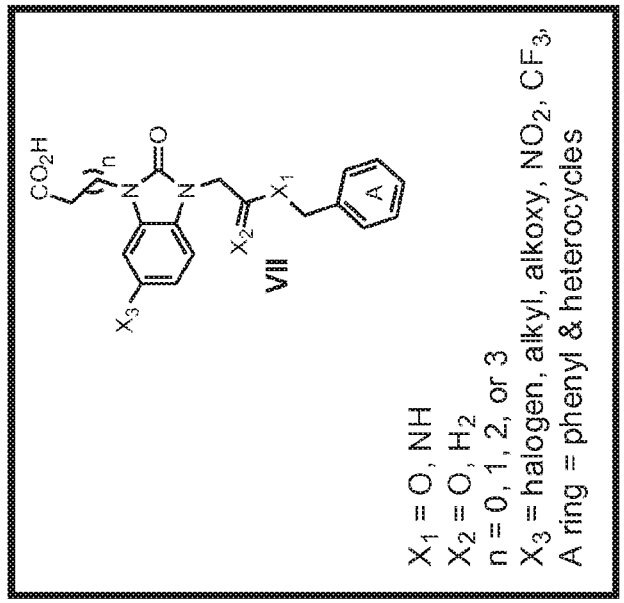

FIG. 13 depicts structural information and computational data for a compound of Scaffold 4 of formula VII

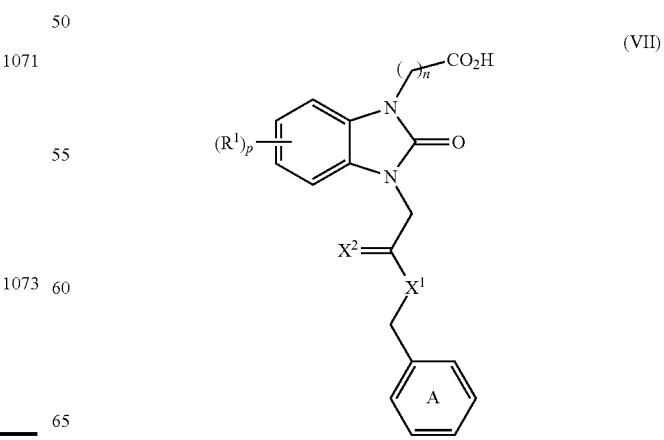

(VII)

wherein the ring labeled A is a substituted or unsubstituted aryl or heteroaryl ring, each $R^1$ is independently selected halo, (C1-C6)alkyl, (C1-C6)alkoxy, nitro, or trifluoromethyl; n=1, 2, or 3; p=0, 1, 2, or 3; $X^1$ is O or NR, $X^2$ is O or $H_2$; R is H or (C1-C6)alkyl; or a pharmaceutically acceptable salt thereof.

Compounds of formula VII can be prepared according to Synthetic Scheme 5, below.

Figure 14:
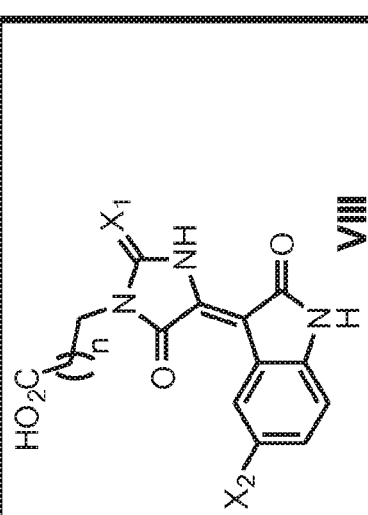
FIG. 14 shows structural and computational data for Scaffold 5.
Figure 14:
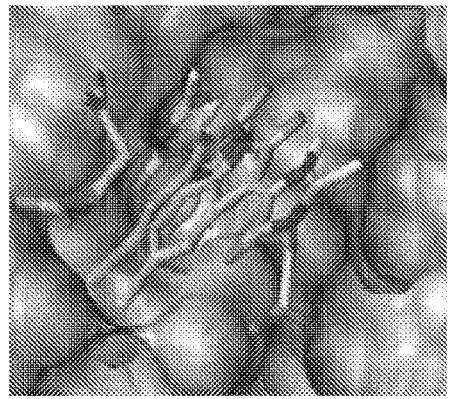
Figure 14:
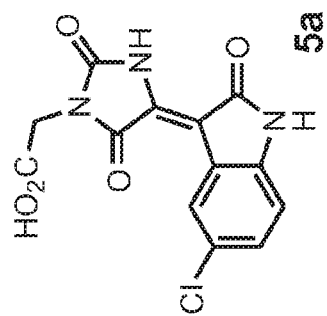

FIG. 14 depicts structural information and computational data for a compound of Scaffold 5, structure VIII,

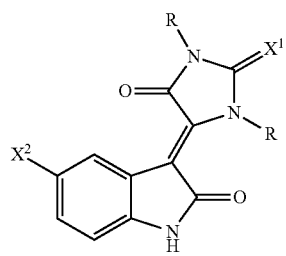

(VIII)

wherein $X^1$ is O or S; R is a group of formula —CH$_2$(CH$_2$)$_n$CO2H or H, provided one and only one R is H; n=0, 1, 2, or 3; $X^2$ is halo, (C1-C6)alkyl, (C1-C6)alkoxy, nitro, or trifluoromethyl; or a pharmaceutically acceptable salt thereof; the compounds of which formula can be prepared according to Synthetic Scheme 6, below. Exemplary compounds of formula VIII include

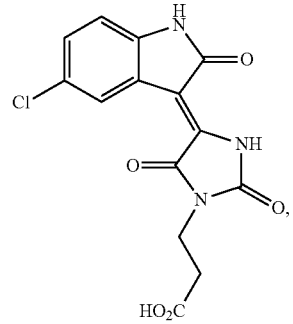

1009

1011

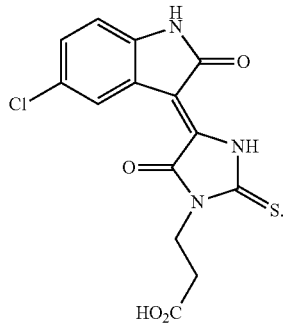

1023

Figure 15:
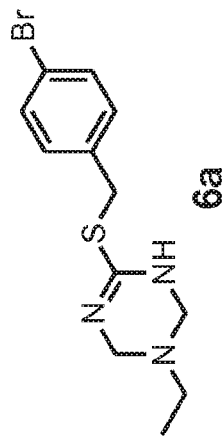
FIG. 15 shows structural and computational data for Scaffold 6.
Figure 15:
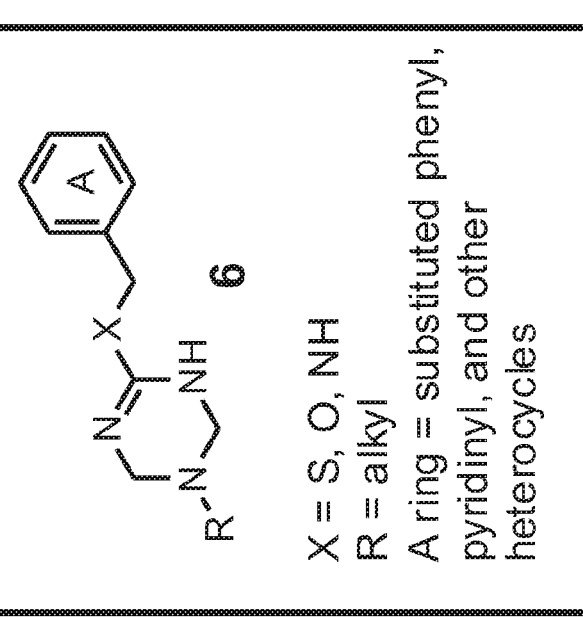
Figure 15:
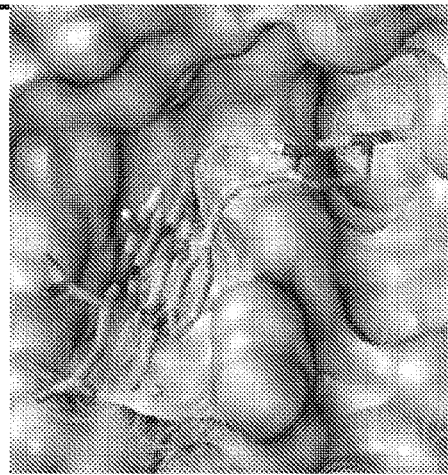

FIG. 15 presents structural information and computational data for a compound of Scaffold 6, structure 6. Compounds can be prepared according to Synthetic Scheme 7.

Figure 16:
FIG. 16 shows structural and computational data for Scaffold 7.
Figure 16:
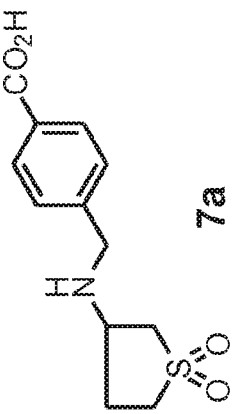
Figure 16:
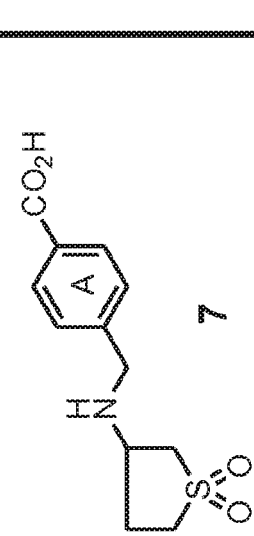

FIG. 16 presents structural information and computational data for a compound of Scaffold 7. Compounds can be prepared according to Synthetic Scheme 8.

Figure 17:
FIG. 17 shows structural and computational data for Scaffold 8.
Figure 17:
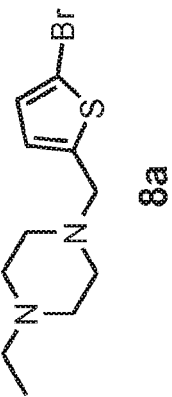
Figure 17:

FIG. 17 present structural information and computational data for a compound of Scaffold 8. Compounds can be prepared according to Synthetic Scheme 9.

Figure 18:
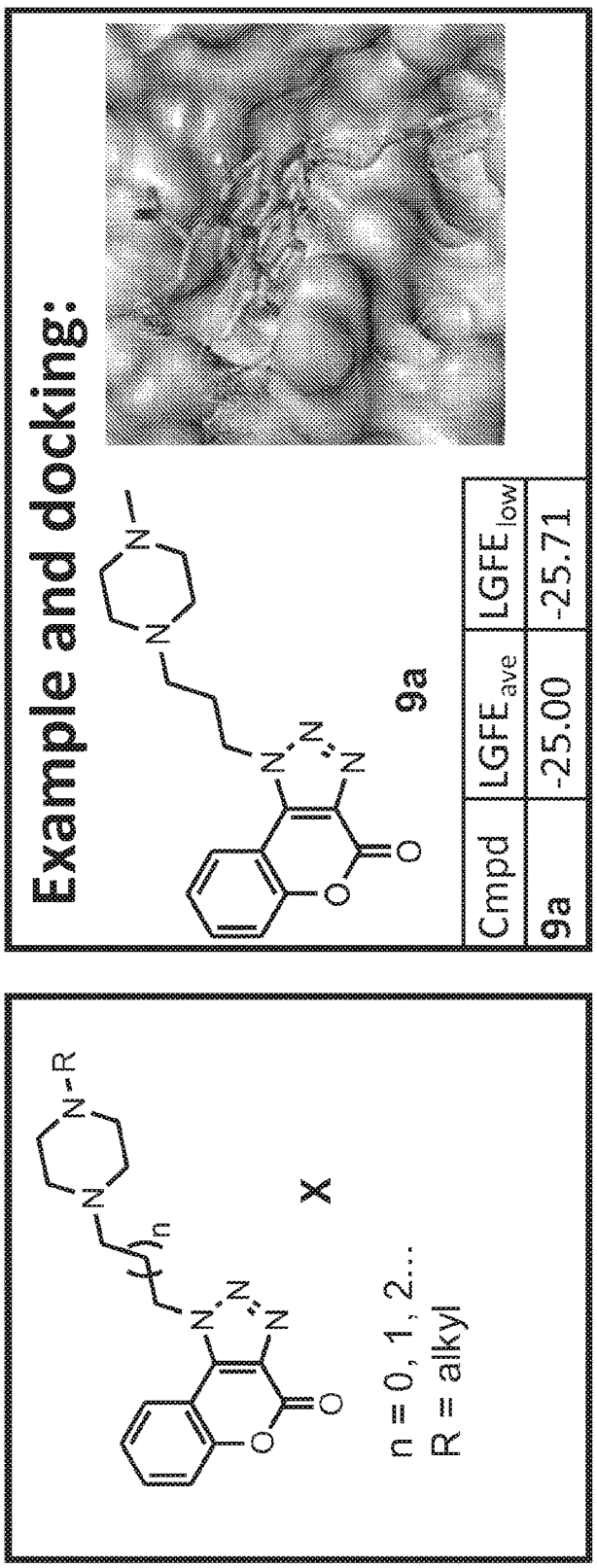
FIG. 18 shows structural and computational data for Scaffold 9.

FIG. 18 presents structural information and computational data for a compound of Scaffold 9, structure X,

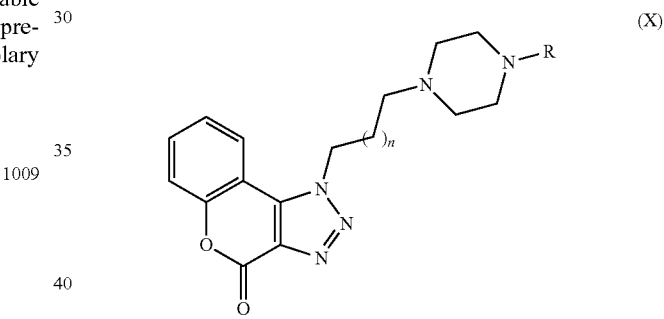

Figure 19:
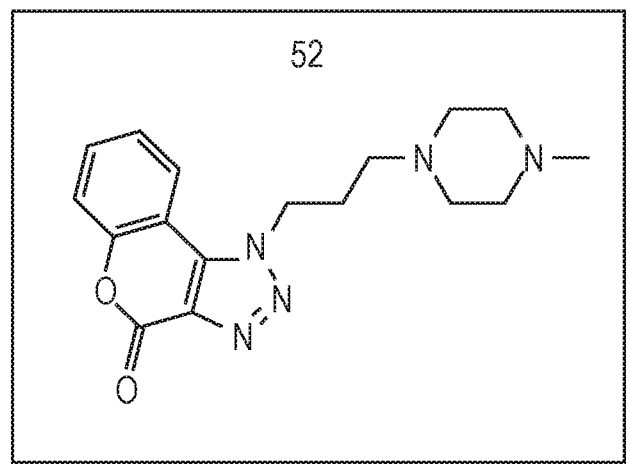
FIG. 19 shows biodata for a compound of Scaffold 9.
Figure 19:
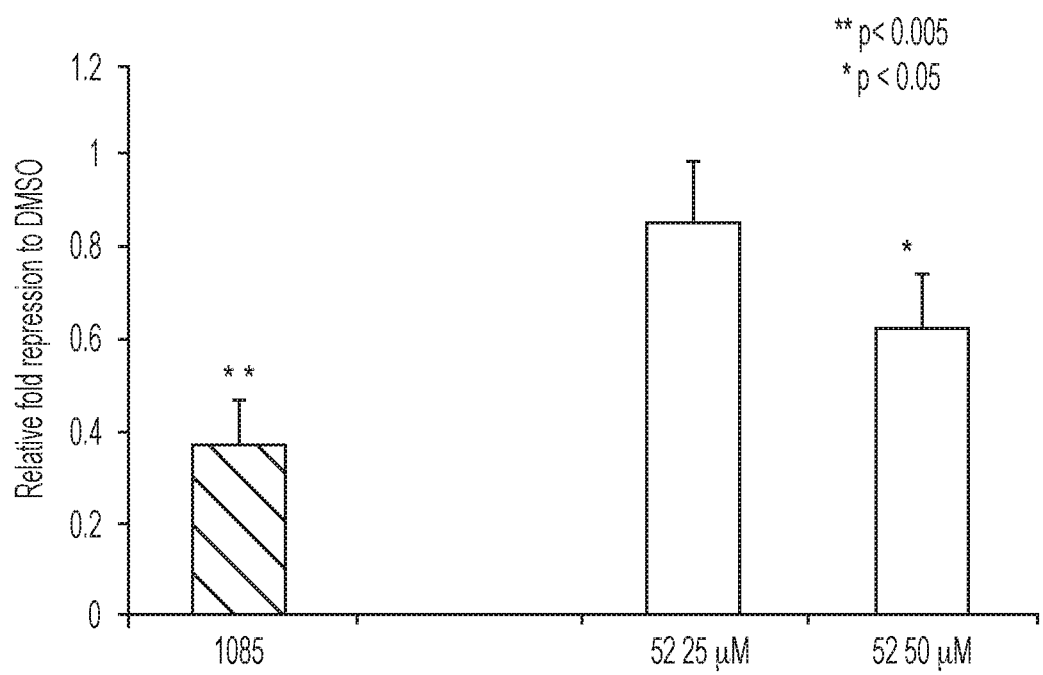

(X)

wherein n=0, 1, 2, or 3, and R is (C1-C6)alkyl, compounds of which type can be prepared according to the Synthetic Scheme 10, below. FIG. 19 presents biodata for an exemplary compound of Scaffold 9.

Figure 20:
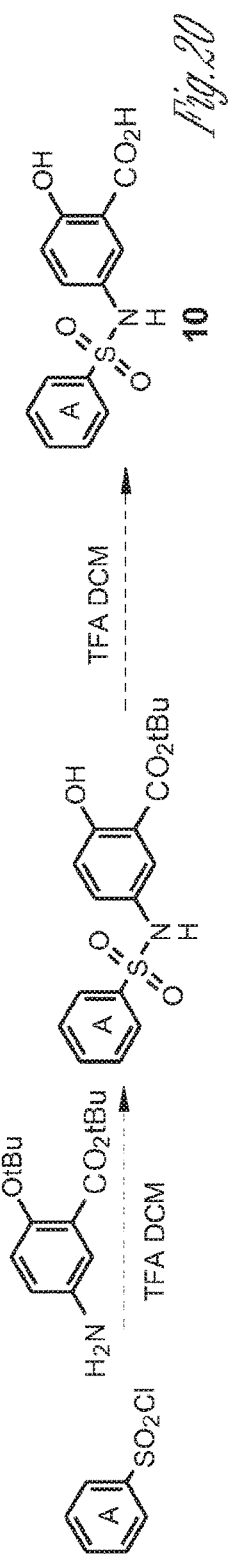
FIG. 20 shows structural and computational data for Scaffold 10.

FIG. 20 presents structural information and computational data for a compound of Scaffold 10. The exemplary compound of structure 34 was found to be inactive. A synthetic route is also shown in FIG. 20.

Figure 21:
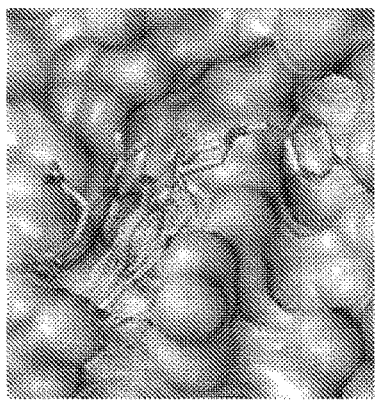
FIG. 21 shows structural and computational data for Scaffold 11.
Figure 21:
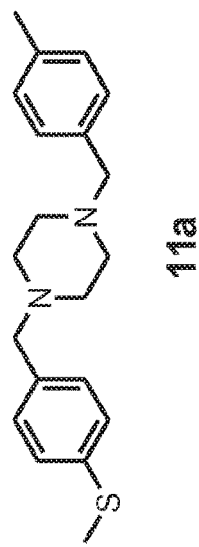
Figure 21:
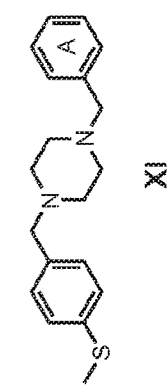
Figure 22:
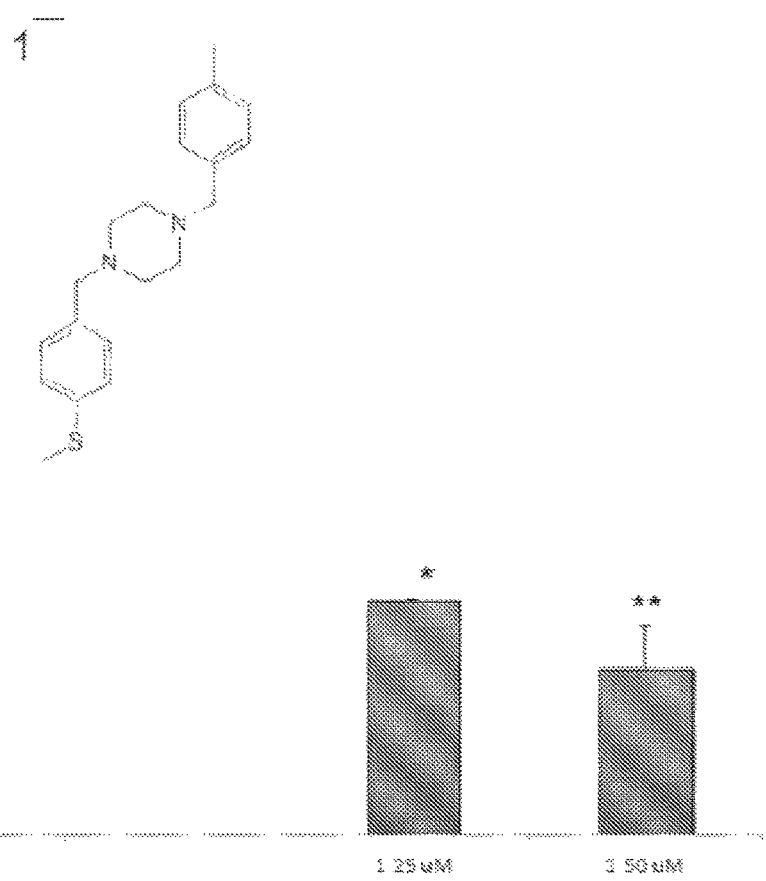
FIG. 22 shows biodata for a compound of Scaffold 11.

FIG. 21 presents structural information and computational data for a compound of Scaffold 11, formula XI

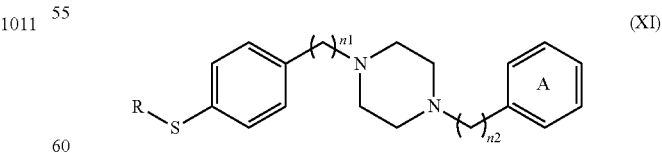

(XI)

wherein the ring labeled A is a substituted or unsubstituted aryl or heteroaryl; R is (C1-C6)alkyl, each of n1 and n2 are independently 1, 2, or 3; or a pharmaceutically acceptable salt thereof Compounds of Scaffold 11 can be prepared according to Synthetic Scheme 11.

FIG. 21 presents biodata for a compound of Scaffold 11.

Figure 23A:
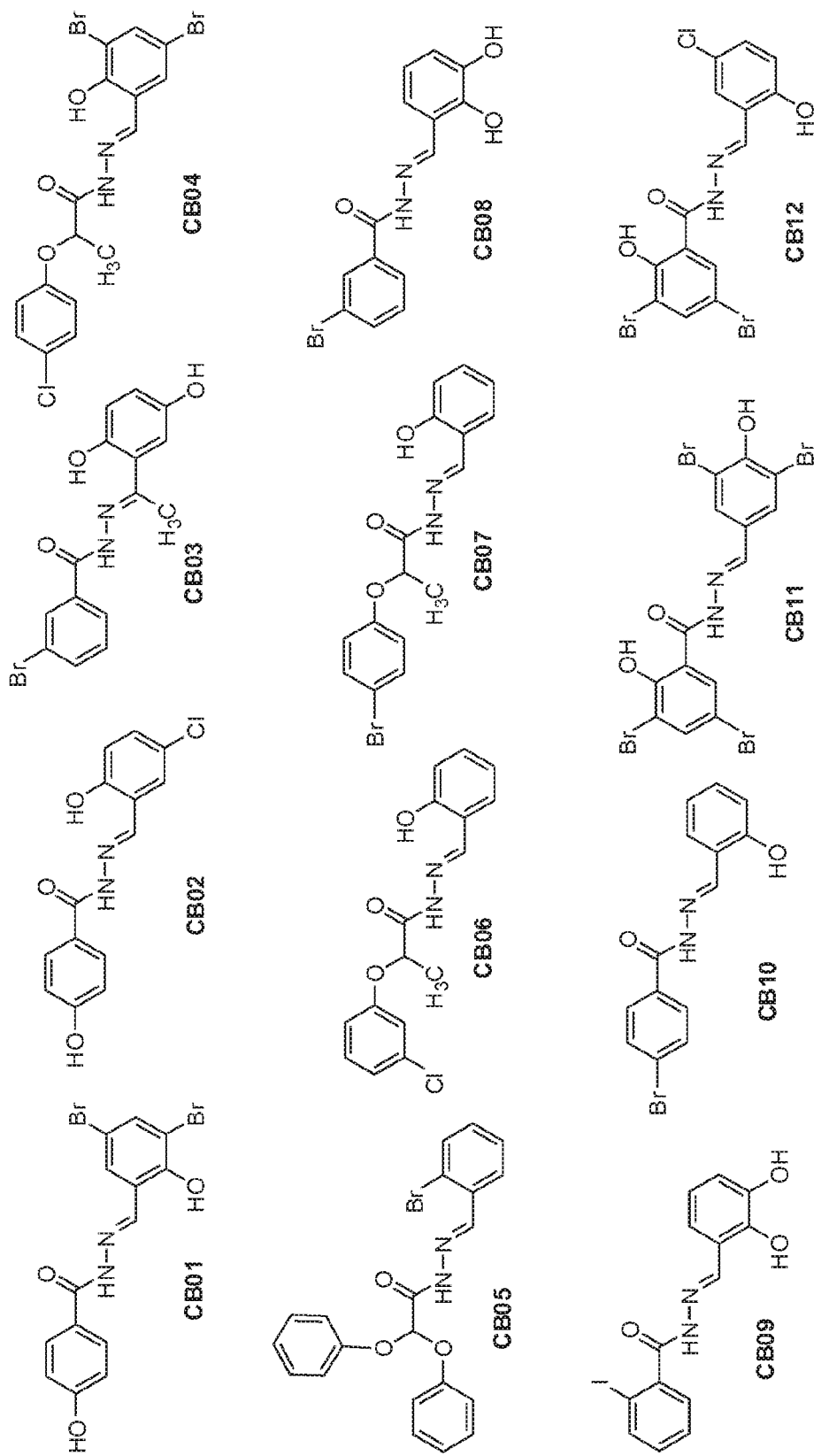
FIGS. 23A-D shows structures of exemplary compounds of Scaffold 12.
Figure 23B:
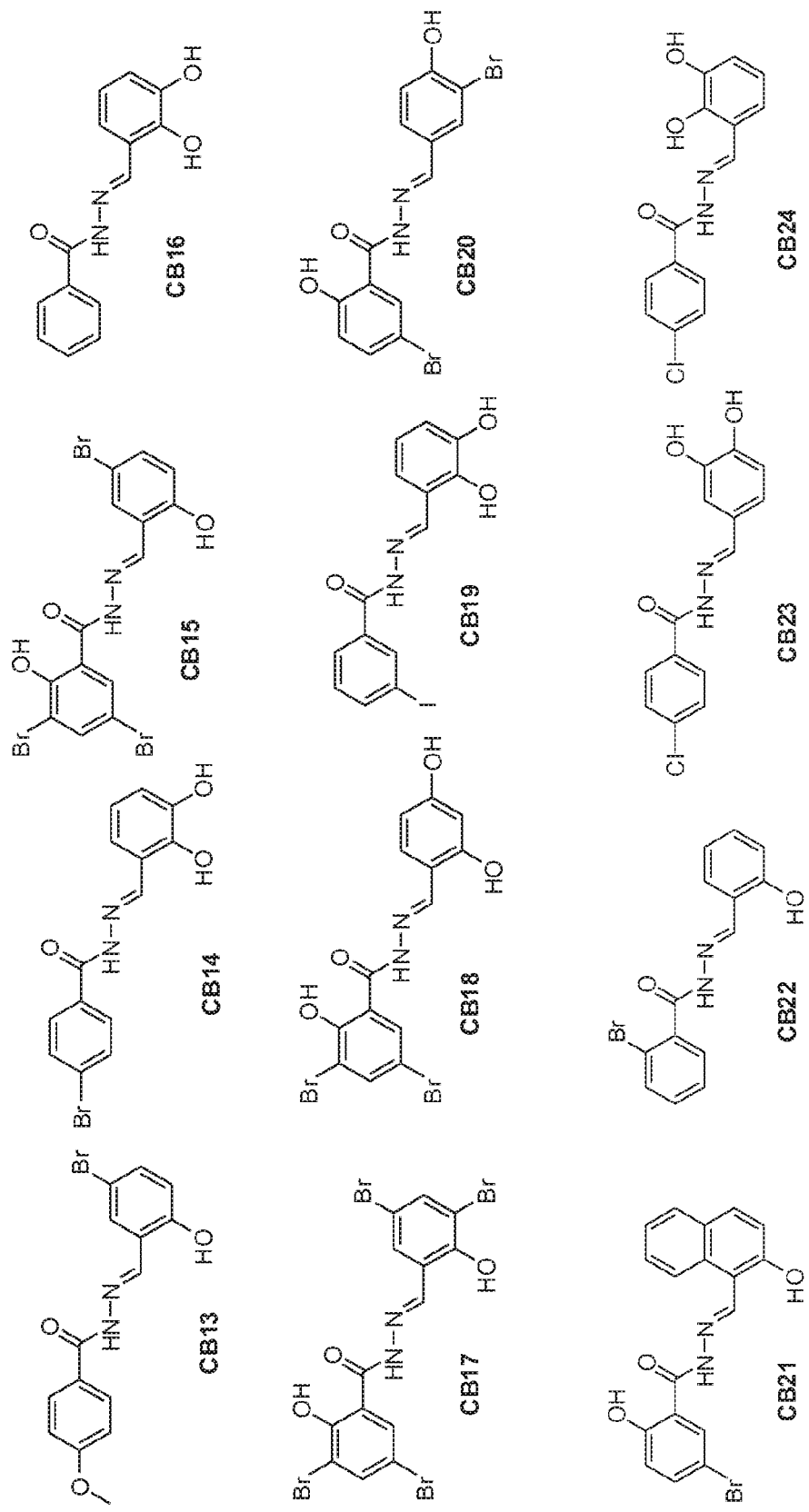
Figure 23C:
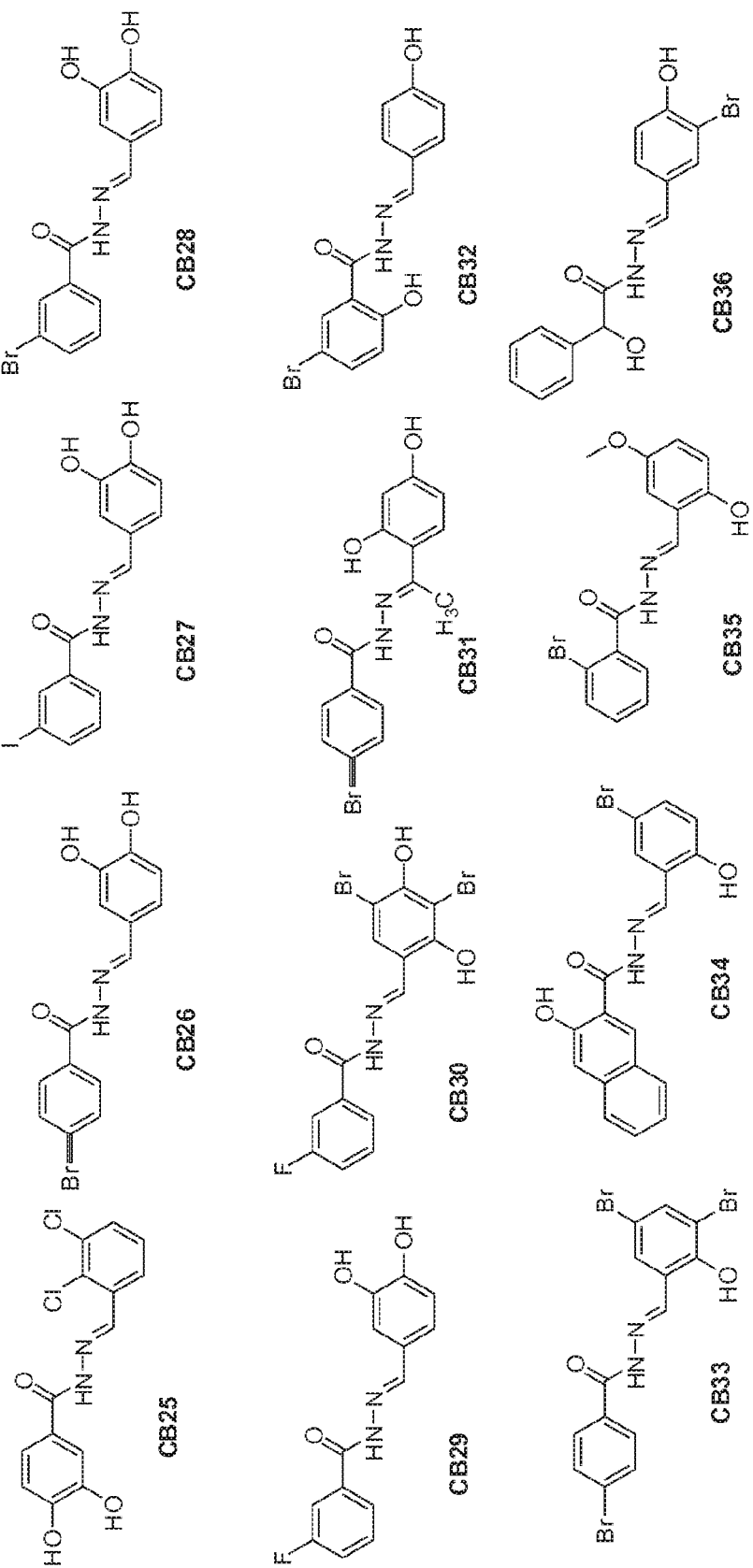
Figure 23D:
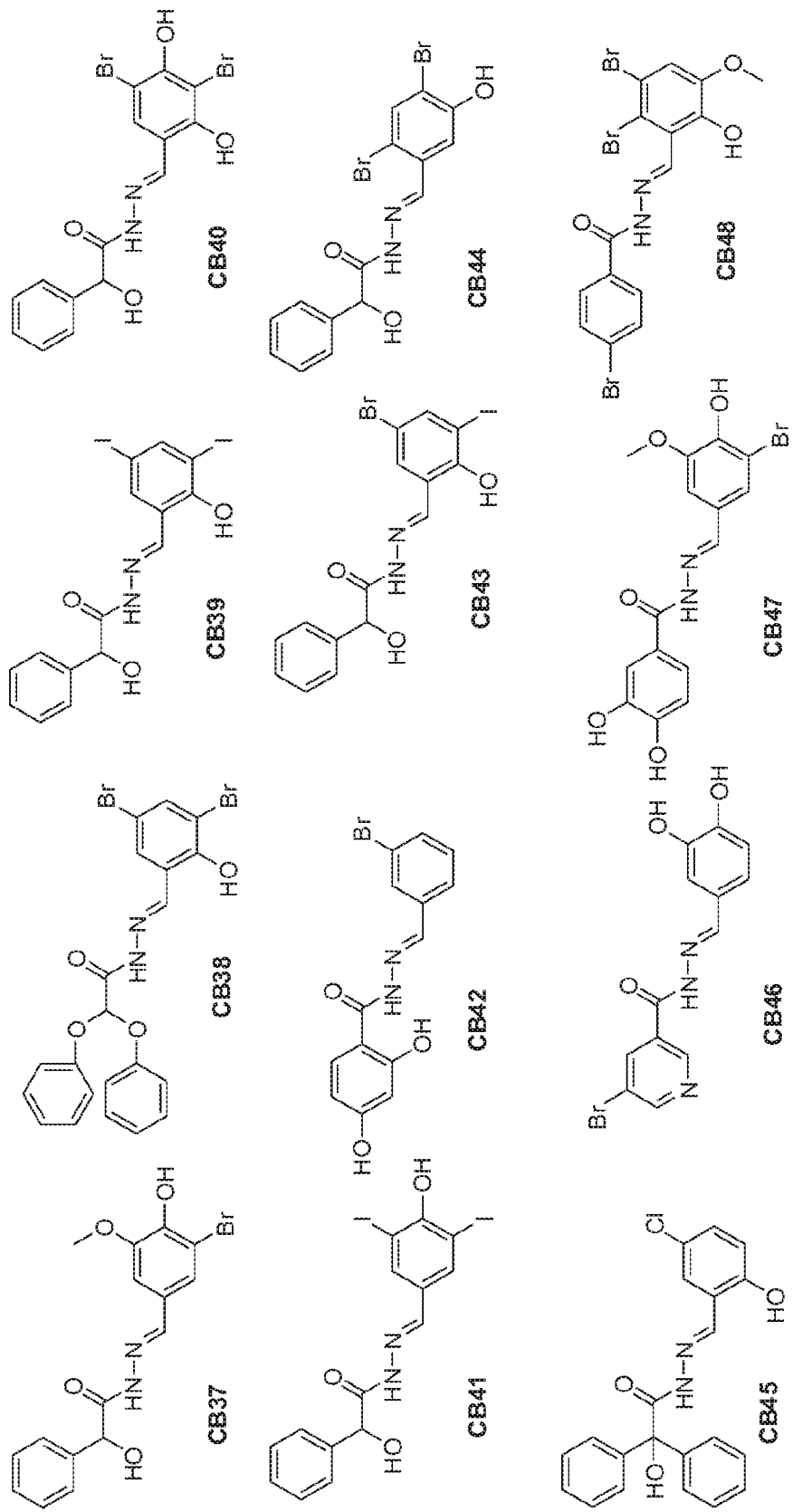
Figure 24:
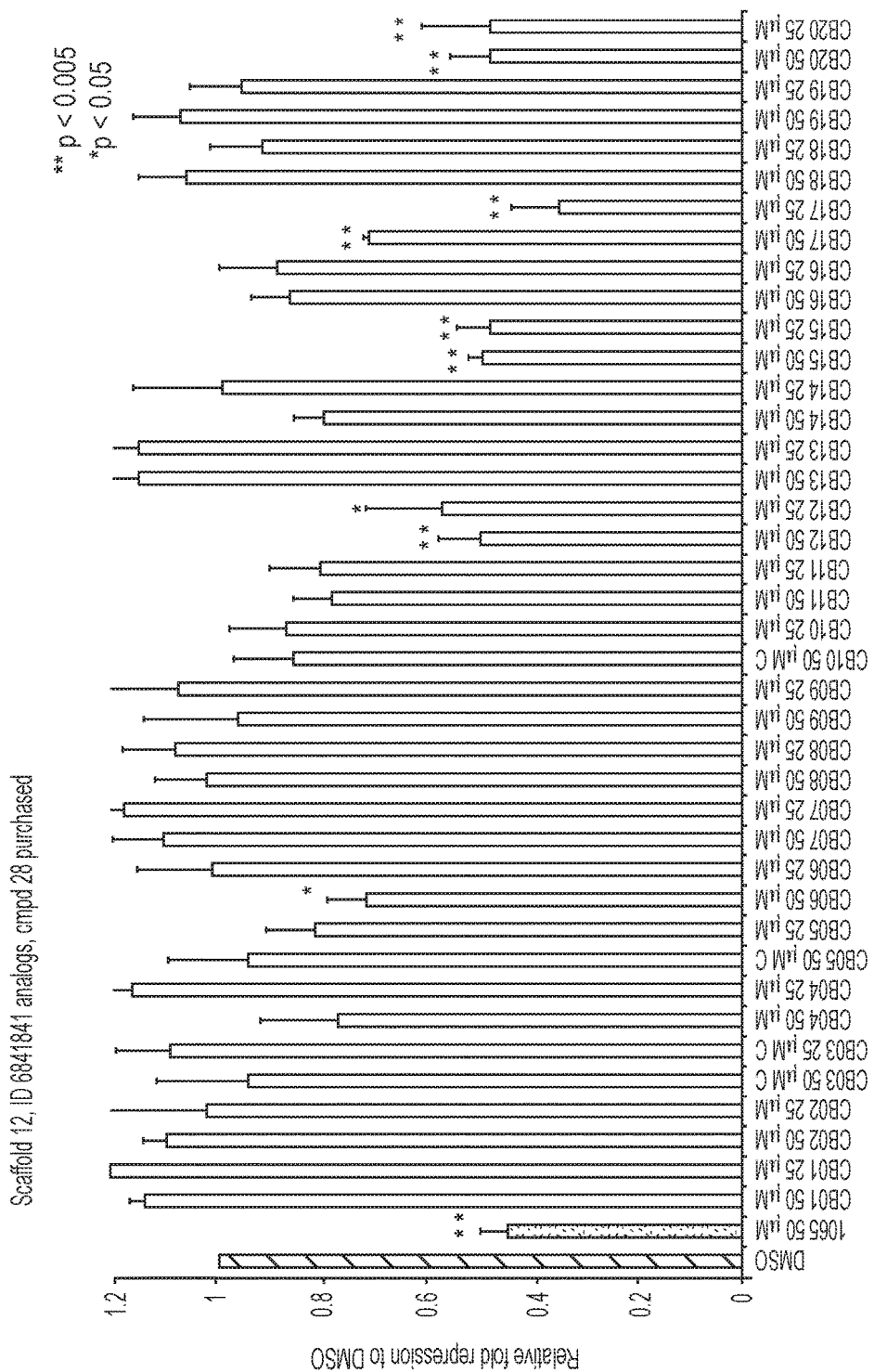
FIGS. 24-27 show biodata for compounds of Scaffold 12, analogous to the results shown for FIG. 1.
Figure 25:
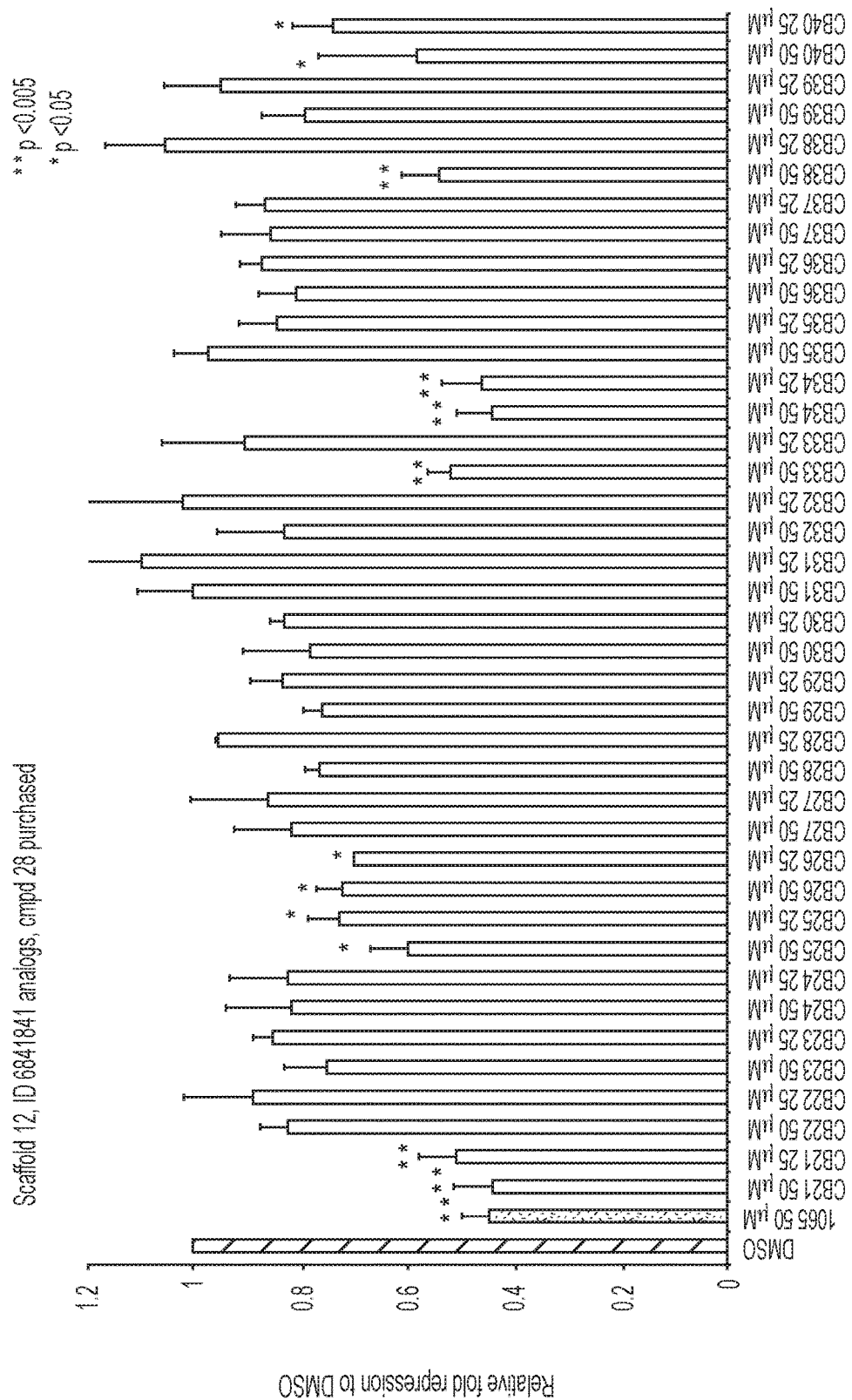
Figure 26:
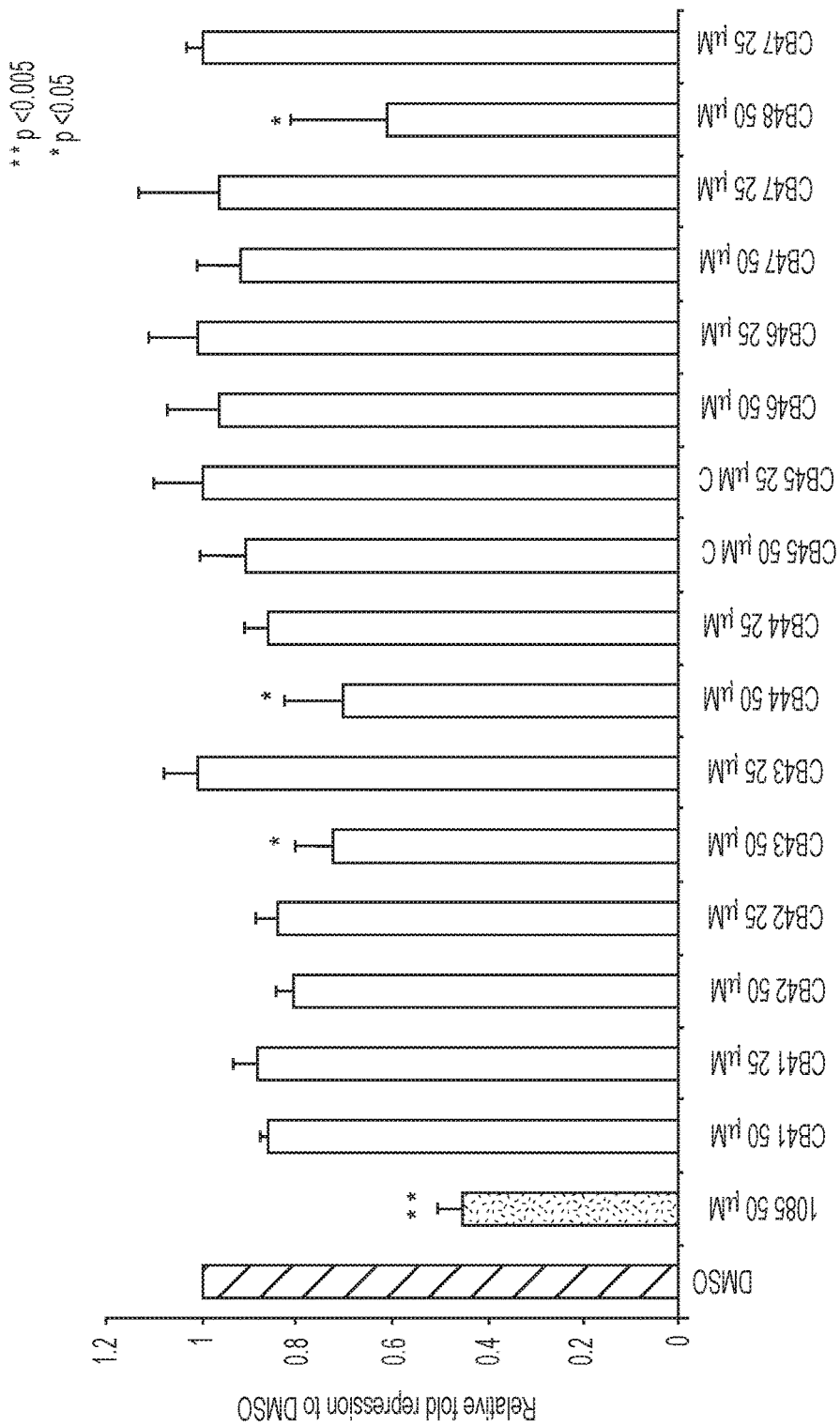
Figure 27:
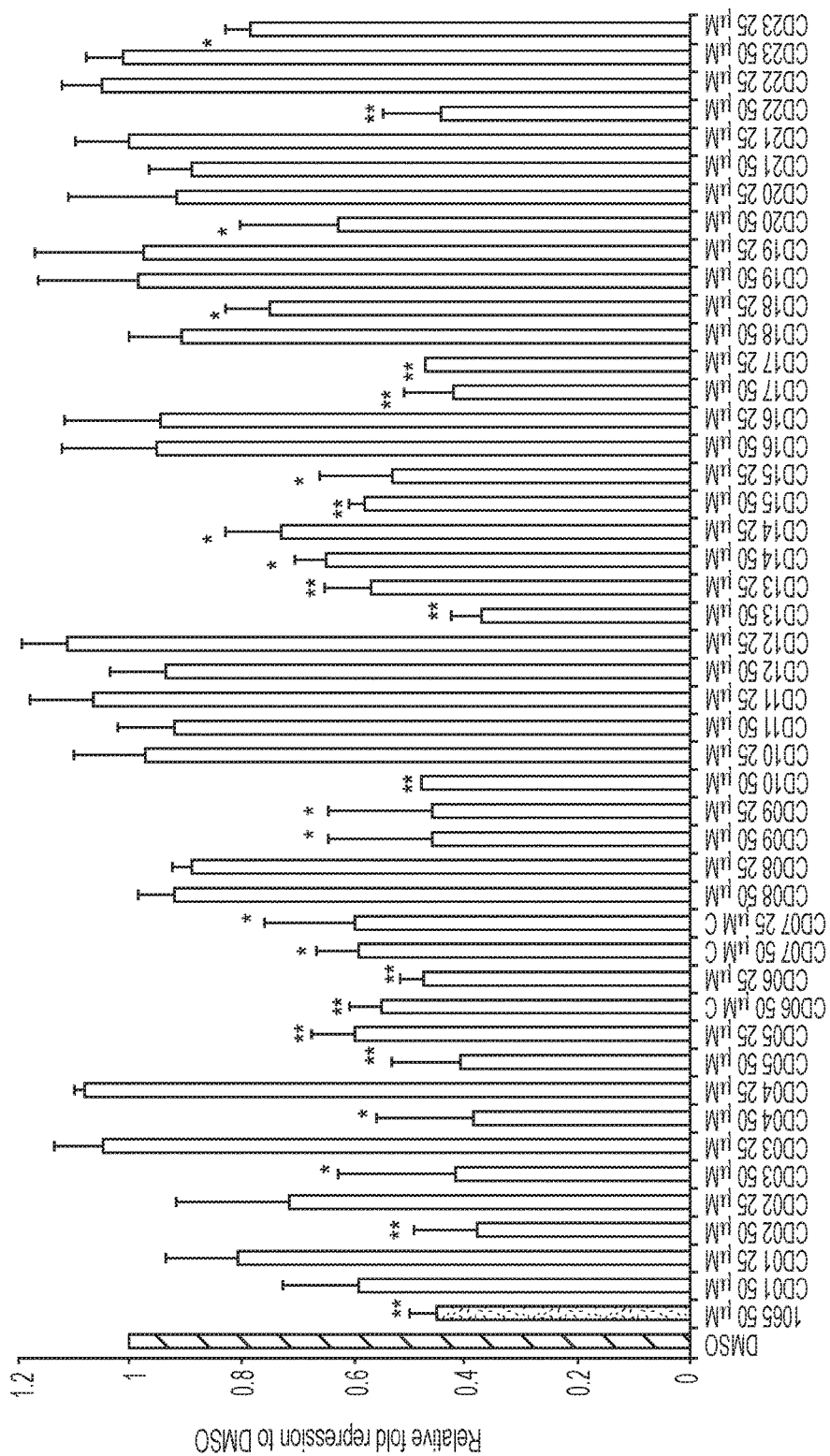

FIGS. 23(A), (B), and (C) show compounds of Scaffold 12.

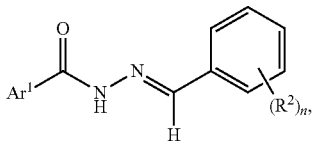

(12)

wherein $Ar^1$ is a substituted or unsubstituted aryl or heteroaryl, $R^2$ is halo, (C1-C6)alkyl, (C1-C6)alkoxy, nitro, or trifluoromethyl; n=0, 1, 2, or 3; or a pharmaceutically acceptable salt thereof. Compounds of Scaffold 12 of formula (12) can be prepared by condensation of a hydrazide and an aldehyde, as shown in Synthetic Scheme 12.

FIGS. 25-28 present biodata for compounds of Scaffold 12.

The invention further provides a method of treatment of a patient afflicted with cancer, comprising administering to the patient an effective dose of a compound that blocks the BTB lateral groove of BCL6, such as compounds of any of the Scaffolds or Examples provided herein, wherein in addition to administration of the compound that blocks the BTB lateral groove of BCL6, an effective amount of a second anticancer agent is administered to the patient.

For instance, the second anticancer agent is doxorubicin, vincristine, dexamethasone, mechloretamine, or comprises a combination of cyclophosphamide, doxorubicin, vincristine, and prednisone (CHOP). Evaluation of the BCL6 groove binding peptide BPI discussed above, in conjunction with doxorubicin, vincristine, dexamethosone, mechloretamine, and the CHOP combination, in cell lines OCI-LY10, OCI-LY7, OCI-LY1, OCI-LY3, Farage, SU-DHL4, and SU-DHL6, showed at least additive and in some cases synergistic efficacies in all combinations except vincristine in OCI-LY10 and dexamethasone in OCI-LY1, where the effect was less than additive.

DOCUMENTS CITED

"A small-molecule inhibitor of BCL6 kills DLBCL cells in vitro and in vivo", Cerchietti L C, Ghetu A F, Zhu X, Da Silva G F, Zhong S, Matthews M, Bunting K L, Polo J M, Fares C, Arrowsmith C H, Yang S N, Garcia M, Coop A, MacKerell A D Jr., Prive G G, Melnick A, *Cancer Cell,* 2010 Apr. 13 17(4); 400-411.

"A peptidomimetic inhibitor of BCL6 with potent antilymphoma effects in vitro and in vivo", Cerchietti L C, Yang S N, Shaknovic R, Hatzi K, Polo J M, Chadburn A, Dowdy S F, Melnick A, *Blood,* 20098 Apr. 9; 113(5); 3397-3405.

"Sequential transcription factor targeting for diffuse large B-cell lymphomas", Cerchietti L C, Polo J M, Da Silva G F, Farinha P, Shaknovich R, Gascoyne R D, Dowdy S F, Melnick A., *Cancer Res.* 2008 May 1; 68(9); 3361-3369.

"Anticancer therapy SMRT-ens up: targeting the BCL6-SMRT interaction in B cell lymphoma", Compton L A, Hiebert S W, *Cancer Cell,* 2010 Apr. 13; 17(4); 315-316. doi"10.1016/j.ccr.2010.03.012.

Examples

Compounds used in practice of methods of the invention can be prepared by the person of ordinary skill based on the synthetic schemes provided herein in conjunction with ordinary knowledge.

Synthesis and Characterization of New Compounds

Synthetic Scheme 1: Compounds of the 1085 and 2099 series

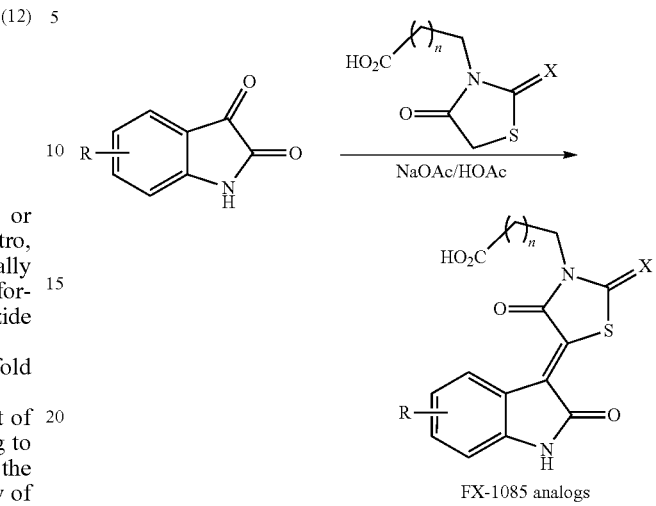

FX-1085 analogs

General Method A: Knoevenagel Condensation.

To a mixture of chloroisatin (1.0 mmol), 3-(4-oxo-2-thioxothiazolidin-3-yl)propanoic acid (205 mg, 1.0 mmol) and NaOAc (820 mg, 10.0 mmol) was added acetic acid (5.0 mL). The reaction was allowed to stir at 105° C. for 30 min-12 h, then cooled to room temperature. To the reaction was added water (15 mL). The resulting mixture was sonicated to give an orange-red slurry. After filtration, the solid was washed with water (75 mL) and dried under high vacuum to yield the corresponding product as a red fine powder (71-92%):

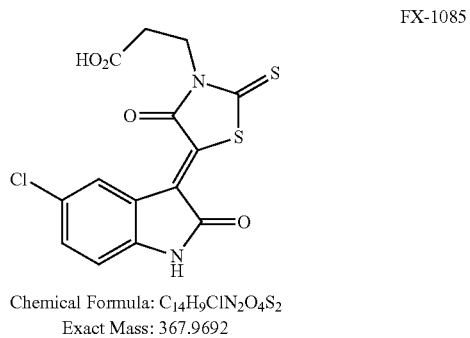 [SMILES: O=C(O)CCN1C(=O)/C(=C2/C(=O)Nc3ccc(Cl)cc32)SC1=S]

FX-1085

Chemical Formula: $C_{14}H_9ClN_2O_4S_2$
Exact Mass: 367.9692

(Z)-3-(5-(5-Chloro-2-oxoindolin-3-ylidene)-4-oxo-2-thioxothiazolidin-3-yl)propanoic acid (FX-1085)

This compound was synthesized using general method A (89%): $^1$H NMR (400 MHz, DMSO-$d_6$) δ 2.60-2.70 (t, J=7.6 Hz, 2H), 4.20-4.30 (t, J=8.0 Hz, 2H), 6.90-7.00 (d, J=8.0 Hz, 1H), 7.40-7.50 (dd, J=2.0, 8.4 Hz, 1H), 8.80-8.81 (d, J=2.0 Hz, 1H), 11.41 (s, 1H), 12.40-12.70 (br s, 1H); $^{13}$C NMR (100 MHz, DMSO-$d_6$) δ 30.8, 112.2, 121.0, 123.8, 126.0, 127.0, 132.3, 132.8, 143.3, 166.6, 167.7, 171.7, 197.1; LC-TOF (M+H$^+$) calcd for $C_{14}H_{10}ClN_2O_4S_2$ 369. found 369.

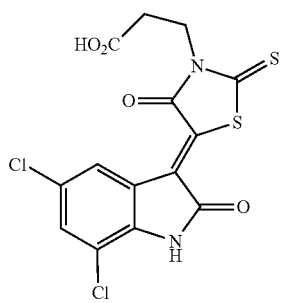

Chemical Formula: $C_{14}H_8Cl_2N_2O_4S_2$
Exact Mass: 401.9303

(Z)-3-(5-(5,7-Dichloro-2-oxoindolin-3-ylidene)-4-oxo-2-thioxothiazolidin-3-yl)propanoic acid (FX-1093)

This compound was synthesized using general method A (80%): $^1$H NMR (400 MHz, DMSO-$d_6$) δ 2.60-2.70 (t, J=7.6 Hz, 2H), 4.25-4.35 (t, J=8.0 Hz, 2H), 7.10-7.15 (d, J=1.6 Hz, 1H), 8.77-8.80 (d, J=1.6 Hz, 1H), 11.86 (s, 1H), 12.40-12.70 (br s, 1H); $^{13}$C NMR (100 MHz, DMSO-$d_6$) δ 30.8, 115.6, 122.2, 123.0, 125.6, 126.3, 131.3, 134.9, 140.9, 166.6, 167.8, 171.7, 196.7; LC-TOF (M+H$^+$) calcd for $C_{14}H_9Cl_2N_2O_4S_2$ 403. found 403.

(Z)-3-(5-(5-Methyl-2-oxoindolin-3-ylidene)-4-oxo-2-thioxothiazolidin-3-yl)propanoic acid (FX-1097)

This compound was synthesized using general method A (90%): $^1$H NMR (400 MHz, DMSO-$d_6$) δ 2.32, (s, 3H), 2.60-2.70 (t, J=7.6 Hz, 2H), 4.20-4.30 (t, J=8.0 Hz, 2H), 6.80-6.90 (d, J=8.0 Hz, 1H), 7.20-7.25 (d, J=8.0 Hz, 1H), 8.64 (s, 1H), 11.16 (s, 1H), 12.40-12.70 (br s, 1H); $^{13}$C NMR (100 MHz, DMSO-$d_6$) δ 20.8, 30.7, 110.4, 119.8, 125.4, 128.1, 130.3, 130.8, 133.6, 142.4, 166.4, 167.9, 171.7, 197.4; LC-TOF (M+H$^+$) calcd for $C_{15}H_{13}N_2O_4S_2$ 349. found 349.

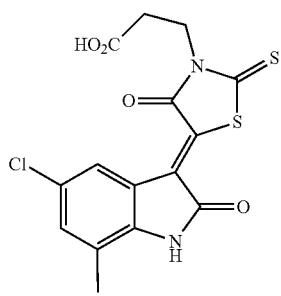

Chemical Formula: $C_{15}H_{11}ClN_2O_4S_2$
Exact Mass: 381.9849

(Z)-3-(5-(5-Chloro-7-methyl-2-oxoindolin-3-ylidene)-4-oxo-2-thioxothiazolidin-3-yl)propanoic acid (FX-1095)

This compound was synthesized using general method A (83%): $^1$H NMR (400 MHz, DMSO-$d_6$) δ 2.23, (s, 3H), 2.60-2.70 (t, J=7.6 Hz, 2H), 4.20-4.30 (t, J=8.0 Hz, 2H), 7.35 (s, 1H), 8.67 (s, 1H), 11.43 (s, 1H), 12.40-12.70 (br s, 1H); $^{13}$C NMR (100 MHz, DMSO-$d_6$) δ 16.6, 31.2, 121.0, 122.6, 124.8, 126.3, 133.7, 142.5, 167.0, 168.6, 172.2, 197.6; LC-TOF (M+H$^+$) calcd for $C_{15}H_{12}ClN_2O_4S_2$ 383. found 383.

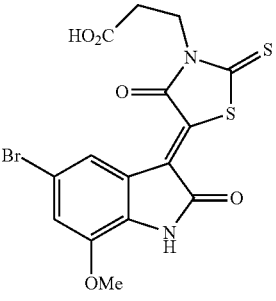

Chemical Formula: $C_{15}H_{11}BrN_2O_5S_2$
Exact Mass: 441.9293

(Z)-3-(5-(5-Bromo-7-methoxy-2-oxoindolin-3-ylidene)-4-oxo-2-thioxothiazolidin-3-yl)propanoic acid (FX-1113)

This compound was synthesized using general method A (85%): $^1$H NMR (400 MHz, DMSO-$d_6$) δ 2.60-2.70 (t, J=7.6 Hz, 2H), 4.20-4.26 (t, J=8.0 Hz, 2H), 4.32 (s, 3H), 7.36 (s, 1H), 8.60 (s, 1H), 11.51 (s, 1H), 12.30-12.70 (br s, 1H); $^{13}$C NMR (100 MHz, DMSO-$d_6$) δ 30.8, 111.6, 114.1, 114.4, 119.3, 119.6, 124.5, 132.7, 141.1, 156.4, 158.7, 166.7, 168.0, 171.8, 197.2; LC-TOF (M+H$^+$) calcd for $C_{15}H_{12}BrN_2O_5S_2$ 443. found 443.

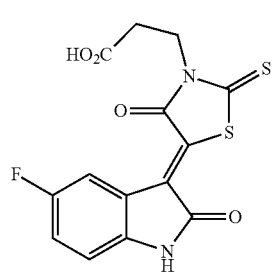

Chemical Formula: $C_{14}H_9FN_2O_4S_2$
Exact Mass: 351.9988

(Z)-3-(5-(5-Fluoro-2-oxoindolin-3-ylidene)-4-oxo-2-thioxothiazolidin-3-yl)propanoic acid (FX-1115)

This compound was synthesized using general method A (86%): $^1$H NMR (400 MHz, DMSO-$d_6$) δ 2.60-2.70 (t, J=7.6 Hz, 2H), 4.20-4.26 (t, J=8.0 Hz, 2H), 6.90-7.00 (dd, J=4.0, 8.0 Hz, 1H), 7.20-7.30 (m, 1H), 8.50-8.60 (d, J=8.0 Hz, 1H), 11.31 (s, 1H), 12.30-12.70 (br s, 1H); $^{13}$C NMR (100 MHz, DMSO-$d_6$) δ 30.8, 111.6, 114.1, 114.4, 119.3, 119.6, 124.5, 132.7, 141.1, 156.4, 158.7, 166.7, 168.0, 171.8, 197.2; LC-TOF (M+H$^+$) calcd for $C_{14}H_{10}FN_2O_4S_2$ 353. found 353.

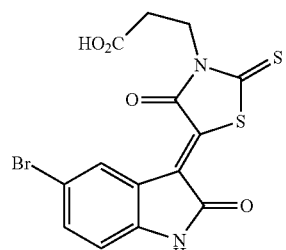

Chemical Formula: $C_{14}H_9BrN_2O_4S_2$
Exact Mass: 411.9187

(Z)-3-(5-(5-Bromo-2-oxoindolin-3-ylidene)-4-oxo-2-thioxothiazolidin-3-yl)propanoic acid (FX-1165)

This compound was synthesized using general method A (85%): $^1$H NMR (400 MHz, DMSO-$d_6$) δ 2.46-2.57 (t, J=7.6 Hz, 2H), 4.20-4.26 (t, J=7.6 Hz, 2H), 6.80-6.90 (d, J=7.6 Hz, 1H), 7.52-7.57 (d, J=8.0 Hz, 1H), 8.93 (s, 1H), 11.39 (s, 1H), 12.30-12.70 (br s, 1H); $^{13}$C NMR (100 MHz, DMSO-$d_6$) δ 30.8, 112.7, 113.7, 121.6, 123.7, 129.8, 135.1, 143.7, 166.7, 167.7, 171.7, 197.1; LC-TOF (M+H$^+$) calcd for $C_{14}H_{10}BrN_2O_4S_2$ 413. found 413.

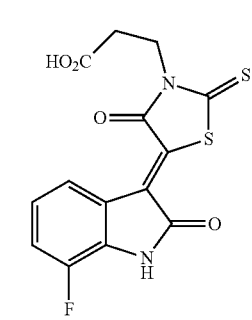

Chemical Formula: $C_{14}H_9FN_2O_4S_2$
Exact Mass: 351.9988

(Z)-3-(5-(7-Fluoro-2-oxoindolin-3-ylidene)-4-oxo-2-thioxothiazolidin-3-yl)propanoic acid (FX-1117)

This compound was synthesized using general method A (92%): $^1$H NMR (400 MHz, DMSO-$d_6$) δ 2.60-2.70 (t, J=7.2 Hz, 2H), 4.20-4.26 (t, J=8.0 Hz, 2H), 7.10-7.20 (m, 1H), 7.36-7.42 (dd, J=8.8, 9.2 Hz, 1H), 11.83 (s, 1H), 12.54 (br s, 1H); $^{13}$C NMR (100 MHz, DMSO-$d_6$) δ 30.8, 119.5, 119.7, 122.5, 122.6, 122.8, 122.9, 123.9, 124.3, 131.5, 131.7, 132.9, 145.5, 147.9, 166.5, 167.9, 171.8, 197.2; LC-TOF (M+H$^+$) calcd for $C_{14}H_{10}FN_2O_4S_2$ 353. found 353.

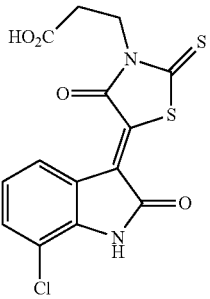

Chemical Formula: $C_{14}H_9ClN_2O_4S_2$
Exact Mass: 367.9692

(Z)-3-(5-(7-Chloro-2-oxoindolin-3-ylidene)-4-oxo-2-thioxothiazolidin-3-yl)propanoic acid (FX-1167)

This compound was synthesized using general method A (90%): $^1$H NMR (400 MHz, DMSO-$d_6$) δ 2.60-2.70 (t, J=8.0 Hz, 2H), 4.20-4.30 (t, J=7.6 Hz, 2H), 7.10-7.15 (t, J=8.0 Hz, 1H), 7.50-7.55 (d, J=7.6 Hz, 1H), 8.70-8.80 (d, J=8.0 Hz, 1H), 11.71 (s, 1H), 12.40-12.80 (br s, 1H); $^{13}$C NMR (100 MHz, DMSO-$d_6$) δ 30.8, 114.9, 121.5, 123.3, 124.3, 126.3, 132.4, 133.0, 141.9, 166.5, 168.0, 171.8, 197.1; LC-TOF (M+H$^+$) calcd for $C_{14}H_{10}ClN_2O_4S_2$ 369. found 369.

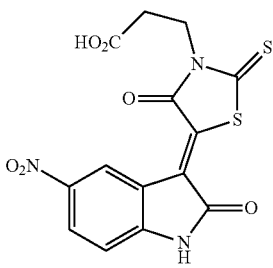

Chemical Formula: C₁₄H₉N₃O₆S₂
Exact Mass: 378.9933

(Z)-3-(5-(5-Nitro-2-oxoindolin-3-ylidene)-4-oxo-2-thioxothiazolidin-3-yl)propanoic acid (FX-1169)

This compound was synthesized using general method A (86%): $^1$H NMR (400 MHz, DMSO-d$_6$) δ 2.60-2.70 (m, 2H), 4.20-4.30 (m, 2H), 7.00-7.10 (d, J=8.4 Hz, 1H), 8.20-8.30 (dd, J=1.6, 8.4 Hz, 1H), 9.50-9.60 (d, J=1.6 Hz, 1H), 11.92 (s, 1H), 13.00-14.00 (br s, 1H); $^{13}$C NMR (100 MHz, DMSO-d$_6$) δ 31.1, 111.4, 120.2, 123.2, 129.0, 135.0, 142.7, 150.1, 167.1, 168.8, 172.1, 197.0; LC-TOF (M+H⁺) calcd for C₁₄H₁₀N₃O₆S₂ 380. found 380.

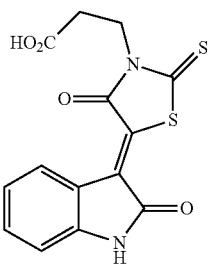

Chemical Formula: C₁₄H₁₀N₂O₄S₂
Exact Mass: 334.0082

(Z)-3-(4-Oxo-5-(2-oxoindolin-3-ylidene)-2-thioxothiazolidin-3-yl)propanoic acid (FX-2001)

This compound was synthesized using general method A (75%): $^1$H NMR (400 MHz, DMSO-d$_6$) δ 1.12-1.16 (t, J=4.0 Hz, 3H), 2.60-2.75 (t, J=8.0 Hz, 2H), 4.00-4.10 (m, 2H), 4.20-4.30 (m, 2H), 6.90-6.95 (d, J=8.0 Hz, 1H), 7.40-7.50 (dd, J=2.0, 8.0 Hz, 1H), 8.75-8.80 (d, J=2.0 Hz, 1H), 11.37 (s, 1H), 13.00-14.00 (br s, 1H); $^{13}$C NMR (100 MHz, DMSO-d$_6$) δ 13.4, 30.3, 59.9, 111.7, 120.5, 123.4, 125.5, 131.8, 132.2, 142.9, 166.1, 167.2, 169.6, 196.6; LC-TOF (M+H⁺) calcd for C₁₄H₁₁N₂O₄S₂ 335. found 335.

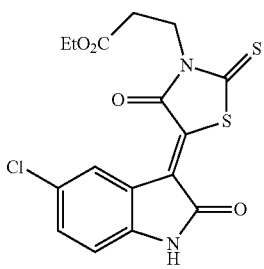

Chemical Formula: C₁₆H₁₃ClN₂O₄S₂
Exact Mass: 396.0005

(Z)-Ethyl 3-(5-(5-chloro-2-oxoindolin-3-ylidene)-4-oxo-2-thioxothiazolidin-3-yl)propanoate (FX-2003)

This compound was synthesized using general method A (74%): $^1$H NMR (400 MHz, DMSO-d$_6$) δ 1.12-1.16 (t, J=4.0 Hz, 3H), 2.60-2.75 (t, J=8.0 Hz, 2H), 4.00-4.10 (m, 2H), 4.20-4.30 (m, 2H), 6.90-6.95 (d, J=8.0 Hz, 1H), 7.40-7.50 (dd, J=2.0, 8.0 Hz, 1H), 8.75-8.80 (d, J=2.0 Hz, 1H), 11.37 (s, 1H), 13.00-14.00 (br s, 1H); $^{13}$C NMR (100 MHz, DMSO-d$_6$) δ 13.4, 30.3, 59.9, 111.7, 120.5, 123.4, 125.5, 131.8, 132.2, 142.9, 166.1, 167.2, 169.6, 196.6; LC-TOF (M+H⁺) calcd for C₁₆H₁₄ClN₂O₄S₂ 398. found 398.

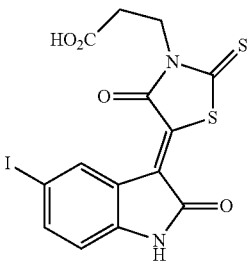

(Z)-3-(5-(5-Iodo-2-oxoindolin-3-ylidene)-4-oxo-2-thioxothiazolidin-3-yl)propanoic acid (FX-2005)

This compound was synthesized using general method A (88%): $^1$H NMR (400 MHz, DMSO-d$_6$) δ 2.60-2.70 (t, J=8.0 Hz, 2H), 4.20-4.30 (m, 2H), 6.80-6.85 (d, J=8.0 Hz, 1H), 7.70-7.75 (d, J=8.0 Hz, 1H), 9.12 (s, 1H), 11.40 (s, 1H), 13.00-14.00 (br s, 1H); $^{13}$C NMR (100 MHz, DMSO-d$_6$) δ 30.8, 85.2, 113.1, 122.0, 123.6, 132.6, 135.5, 140.9, 144.1, 166.7, 167.5, 171.8, 197.2; LC-TOF (M+H⁺) calcd for C₁₀H₁₆N₂O₄ 229. found 229.

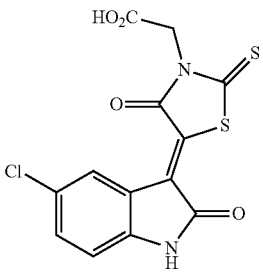

Chemical Formula: C₁₃H₇ClN₂O₄S₂
Exact Mass: 353.9536

(Z)-2-(5-(5-Chloro-2-oxoindolin-3-ylidene)-4-oxo-2-thioxothiazolidin-3-yl)acetic acid (FX-2031)

This compound was synthesized using general method A (85%): $^1$H NMR (400 MHz, DMSO-d$_6$) δ 4.76 (s, 2H), 6.90-6.96 (d, J=8.8 Hz, 1H), 7.40-7.45 (dd, J=1.6, 8.0 Hz, 1H), 8.70 (s, 1H), 11.39 (s, 1H), 13.00-14.00 (br s, 1H); $^{13}$C NMR (100 MHz, DMSO-d$_6$) δ 45.2, 112.7, 121.4, 125.5, 126.5, 127.4, 131.7, 133.1, 144.1, 166.8, 167.6, 167.6, 168.0, 197.4; LC-TOF (M+H⁺) calcd for C₁₃H₈ClN₂O₄S₂ 355. found 355.

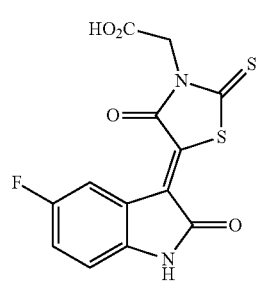

FX-2033

Chemical Formula: C₁₃H₇FN₂O₄S₂
Exact Mass: 337.9831

(Z)-2-(5-(5-Fluoro-2-oxoindolin-3-ylidene)-4-oxo-2-thioxothiazolidin-3-yl)acetic acid (FX-2033)

This compound was synthesized using general method A (85%): $^1$H NMR (400 MHz, DMSO-d$_6$) δ 4.76 (s, 2H), 6.90-7.00 (dd, J=4.0, 8.0 Hz, 1H), 7.26-7.30 (m, 1H), 8.40-8.50 (dd, J=2.8, 10.0 Hz, 1H), 11.29 (s, 1H), 13.00-14.00 (br s, 1H); $^{13}$C NMR (100 MHz, DMSO-d$_6$) δ 44.9, 1118, 114.3, 114.5, 119.8, 120.1, 125.8, 131.2, 141.5, 156.5, 158.8, 166.5, 167.3, 168.0, 197.2; LC-TOF (M+H$^+$) calcd for C₁₃H₈FN₂O₄S₂ 339. found 339.

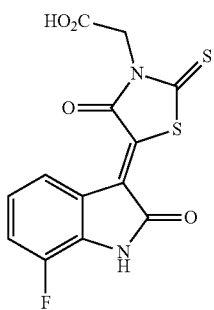

FX-2035

Chemical Formula: C₁₃H₇FN₂O₄S₂
Exact Mass: 337.9831

(Z)-2-(5-(7-Fluoro-2-oxoindolin-3-ylidene)-4-oxo-2-thioxothiazolidin-3-yl)acetic acid (FX-2035)

This compound was synthesized using general method A (72%): $^1$H NMR (400 MHz, DMSO-d$_6$) δ 4.78 (s, 2H), 7.00-7.15 (m, 1H), 7.36-7.41 (m, 1H), 8.50-8.65 (d, J=7.6 Hz, 1H), 11.84 (s, 1H), 13.00-14.00 (br s, 1H); $^{13}$C NMR (100 MHz, DMSO-d$_6$) δ 45.1, 120.2, 120.4, 122.7, 123.2, 124.2, 125.7, 131.6, 132.3, 145.8, 148.2, 166.4, 167.6, 168.0, 197.3; LC-TOF (M+H$^+$) calcd for C₁₃H₈FN₂O₄S₂ 339. found 339.

FX-2037

Chemical Formula: C₁₃H₇ClN₂O₄S₂
Exact Mass: 353.9536

(Z)-2-(5-(7-Chloro-2-oxoindolin-3-ylidene)-4-oxo-2-thioxothiazolidin-3-yl)acetic acid (FX-2037)

This compound was synthesized using general method A (75%): $^1$H NMR (400 MHz, DMSO-d$_6$) δ 4.78 (s, 2H), 7.08-7.12 (dd, J=8.0, 8.0 Hz, 1H), 7.49-7.51 (d, J=8.0 Hz, 1H), 8.70-8.75 (d, J=8.0 Hz, 1H), 11.72 (s, 1H), 13.00-14.00 (br s, 1H); $^{13}$C NMR (100 MHz, DMSO-d$_6$) δ 45.1, 115.3, 121.8, 123.6, 125.8, 126.6, 131.7, 133.1, 142.6, 166.4, 167.5, 168.2, 197.3; LC-TOF (M+H$^+$) calcd for C₁₃H₈ClN₂O₄S₂ 355. found 355.

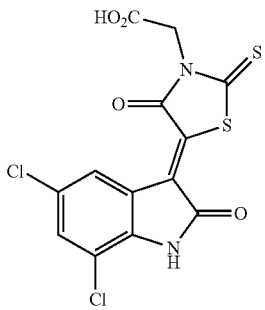

FX-2039

Chemical Formula: C₁₃H₆Cl₂N₂O₄S₂
Exact Mass: 387.9146

(Z)-2-(5-(5,7-Dichloro-2-oxoindolin-3-ylidene)-4-oxo-2-thioxothiazolidin-3-yl)acetic acid (FX-2039).

This compound was synthesized using general method A (71%): $^1$H NMR (400 MHz, DMSO-d$_6$) δ 4.81 (s, 2H), 7.70 (s, 1H), 8.74 (s, 1H), 8.85 (s, 1H), 11.90 (s, 1H), 13.00-14.00 (br s, 1H); $^{13}$C NMR (100 MHz, DMSO-d$_6$) δ 44.4, 115.7, 122.1, 124.3, 125.6, 131.6, 133.2, 141.3, 165.9, 166.3, 166.9, 167.2, 167.7, 194.6, 196.7; LC-TOF (M+H$^+$) calcd for C₁₃H₇Cl₂N₂O₄S₂ 389. found 389.

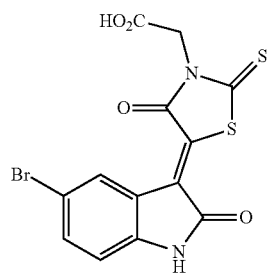

Chemical Formula: $C_{13}H_7BrN_2O_4S_2$
Exact Mass: 397.9031

(Z)-2-(5-(5-Bromo-2-oxoindolin-3-ylidene)-4-oxo-2-thioxothiazolidin-3-yl)acetic acid (FX-2041)

This compound was synthesized using general method A (72%): $^1$H NMR (400 MHz, DMSO-$d_6$) δ 4.77 (s, 2H), 6.87-6.89 (d, J=8.0 Hz, 1H), 7.55-7.57 (d, J=7.6 Hz, 1H), 8.85 (s, 1H), 11.40 (s, 1H), 13.00-14.00 (br s, 1H); $^{13}$C NMR (100 MHz, DMSO-$d_6$) δ 45.2, 113.2, 114.2, 121.9, 125.3, 127.3, 130.2, 131.8, 135.8, 144.5, 166.8, 167.7, 167.9, 197.4; LC-TOF (M+H$^+$) calcd for $C_{13}H_8BrN_2O_4S_2$ 399. found 399.

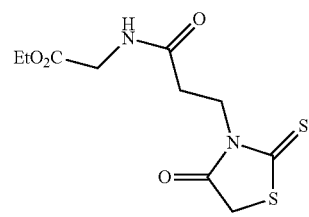

3019

Chemical Formula: $C_{10}H_{14}N_2O_4S_2$
Exact Mass: 290.0395

Ethyl 2-(3-(4-oxo-2-thioxothiazolidin-3-yl)propanamido)acetate (FX-3019)

To a mixture of 3-(4-oxo-2-thioxothiazolidin-3-yl)propanoic acid (205 mg, 1.0 mmol), H$_2$N-Gly-OEt hydrochloride (140 mg, 1.0 mmol) and EDC (192 mg, 1.0 mmol) in DMF (5.0 mL) was added triethylamine (140 μL, 1.0 mmol). The reaction mixture was stirred at room temperature for 16 h, and then concentrated. The crude product was purified by flash chromatography (EtOAc/Hexanes 1:2-1:1) to give FX-3019 as a white solid (276 mg, 0.95 mmol, 95%): $^1$H NMR (400 MHz, DMSO-$d_6$) δ 1.25-1.30 (t, J=6.8 Hz, 3H), 2.64-2.70 (t, J=7.6 Hz, 2H), 4.01 (s, 3H), 4.20-4.25 (dd, J=7.2, 14.0 Hz, 2H), 4.25-4.35 (t, J=8.0 Hz, 2H), 6.04 (s, 1H); $^{13}$C NMR (100 MHz, DMSO-$d_6$) δ 14.1, 32.7, 35.4, 40.6, 41.4, 61.7, 169.4, 169.8, 173.6, 201.0; LC-TOF (M+H$^+$) calcd for $C_{10}H_{15}N_2O_4S_2$ 291. found 291.

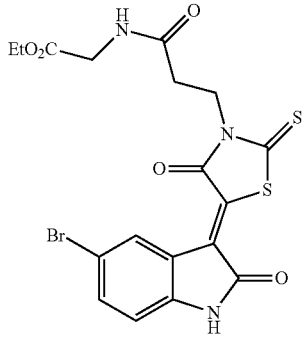

Chemical Formula: $C_{18}H_{16}BrN_3O_5S_2$
Exact Mass: 496.9715

(Z)-ethyl 2-(3-(5-(5-Bromo-2-oxoindolin-3-ylidene)-4-oxo-2-thioxothiazolidin-3-yl)propanamido) acetate (FX-3021)

This compound was synthesized using general method A (75%): $^1$H NMR (400 MHz, DMSO-$d_6$) δ 1.15-1.20 (t, J=7.2 Hz, 3H), 2.50-2.65 (t, J=7.6 Hz, 2H), 3.76-3.80 (d, J=5.6 Hz, 2H), 4.04-4.10 (dd, J=6.8, 15.0 Hz, 2H), 4.20-4.30 (m, 2H), 6.97-7.00 (d, J=7.6 Hz, 1H), 7.47-7.49 (d, J=7.6 Hz, 1H), 8.50 (s, 1H), 8.83 (s, 1H), 11.41 (s, 1H); $^{13}$C NMR (100 MHz, DMSO-$d_6$) δ 14.1, 31.7, 40.4, 40.7, 60.4, 112.2, 121.1, 123.7, 126.0, 127.0, 132.2, 133.0, 143.3, 166.7, 167.8, 169.6, 169.7, 197.1; LC-TOF (M+H$^+$) calcd for $C_{18}H_{17}BrN_3O_5S_2$ 498. found 498.

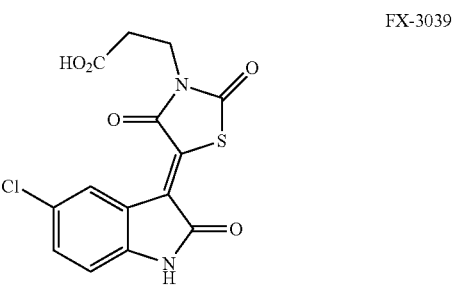

Chemical Formula: $C_{14}H_9ClN_2O_5S$
Exact Mass: 351.9921

(Z)-3-(5-(5-Chloro-2-oxoindolin-3-ylidene)-2,4-dioxothiazolidin-3-yl)propanoic acid (FX-3039)

This compound was synthesized using general method A (71%): $^1$H NMR (400 MHz, DMSO-$d_6$) δ 2.60-2.70 (t, J=7.6 Hz, 2H), 3.80-3.90 (t, J=7.6 Hz, 2H), 6.90-7.00 (d, J=8.0 Hz, 1H), 7.40-7.50 (dd, J=2.4, 8.0 Hz, 1H), 8.79-8.80 (d, J=2.4 Hz, 1H), 11.37 (s, 1H), 12.42 (br s, 1H); $^{13}$C NMR (100 MHz, DMSO-$d_6$) δ 31.4, 37.0, 112.0, 121.1, 125.9, 127.2, 132.0, 142.6, 165.4, 168.1, 169.5, 171.9; LC-TOF (M+H$^+$) calcd for $C_{14}H_{10}ClN_2O_5S$ 353. found 353.

Compounds of the 2071/3033 series can be prepared according to the following Scheme, in conjunction with ordinary skill and knowledge.

Synthetic Scheme 2: Compounds of the 2071/3033 series
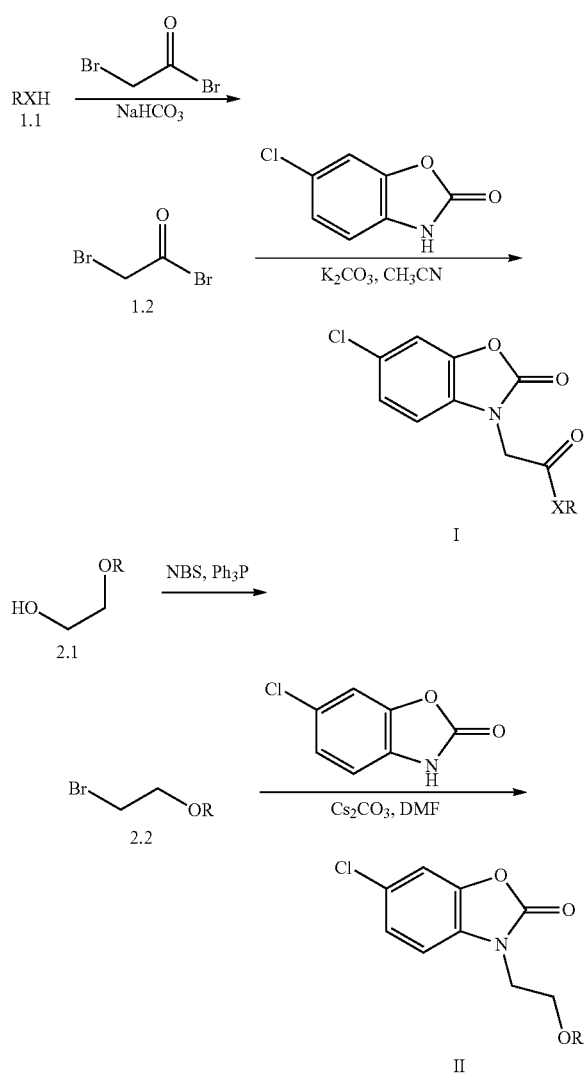
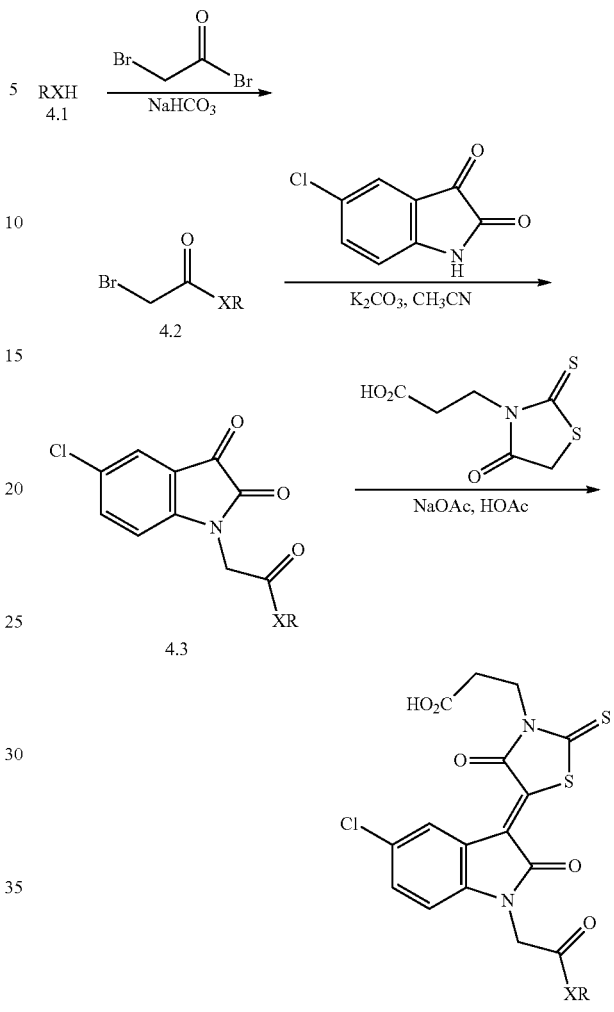
Synthetic Scheme 3: Compounds of Scaffold 2
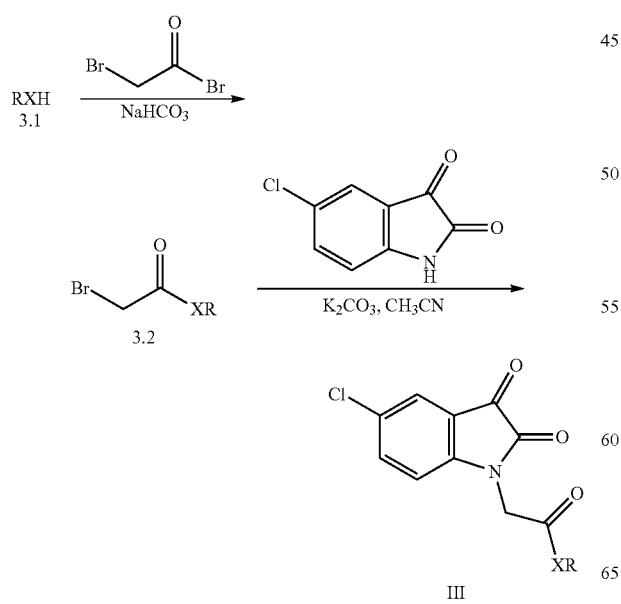

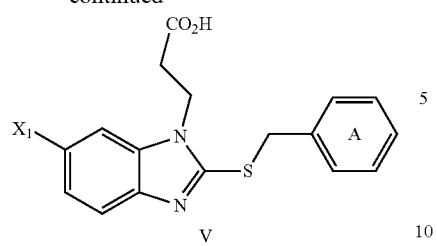
V
Synthetic Scheme 4: Compounds of Scaffold 3
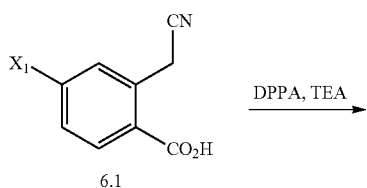
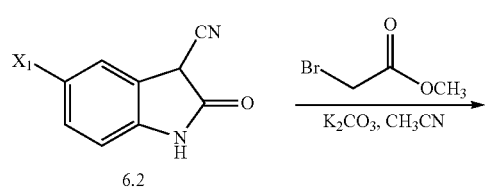
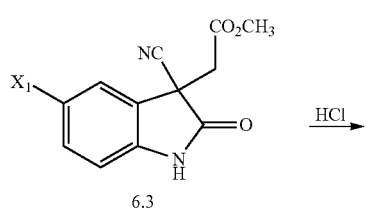
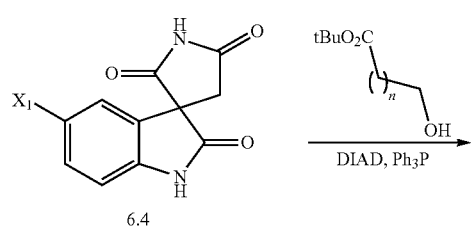
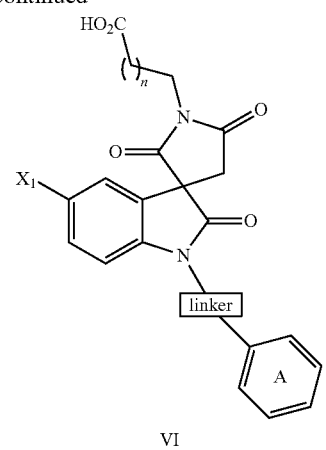
VI
$X_1$ = O, NH
n = 0, 1, 2, or 3
linker = ester, ether, amide,
A ring = phenyl & heterocycles
Synthetic Scheme 5: Compounds of Scaffold 4
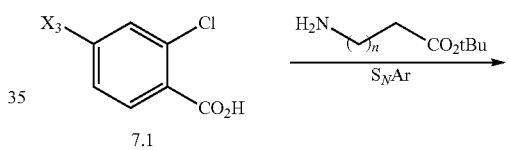
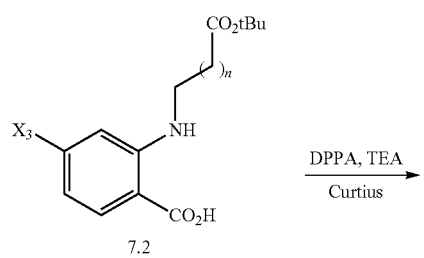
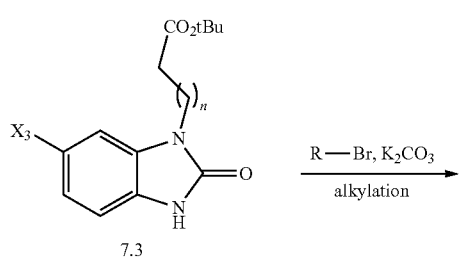
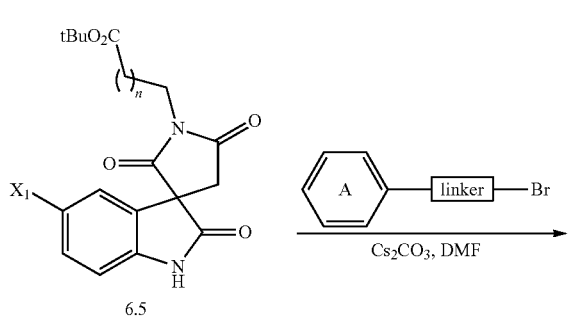

65
-continued
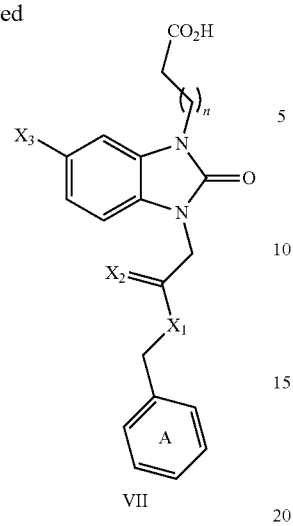
VII
$X_1$ = O, NH
$X_2$ = O, $H_2$
n = 0, 1, 2, or 3
$X_3$ = halogen, alkyl, alkoxy, $NO_2$, $CF_3$,
A ring = phenyl & heterocycles
Synthetic Scheme 6: Compounds of Scaffold 5
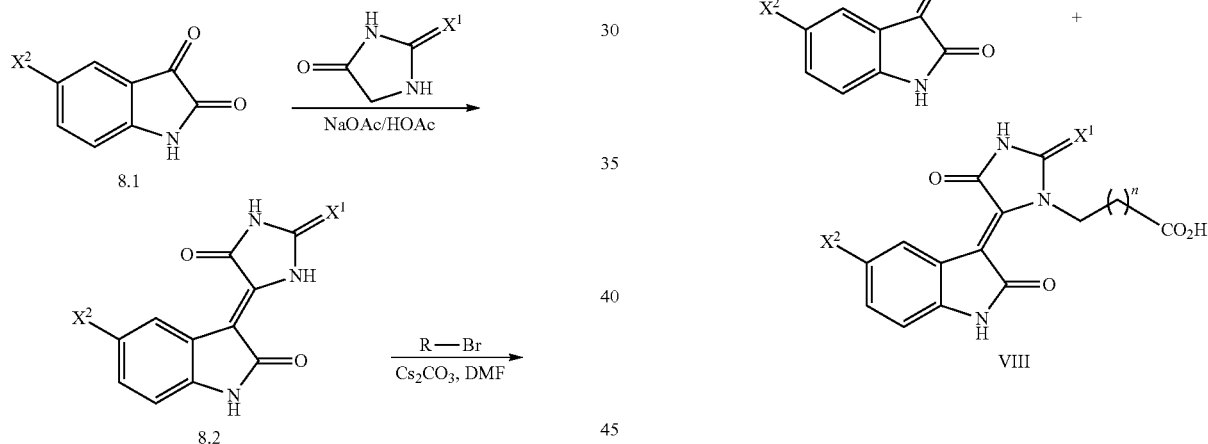
66
-continued
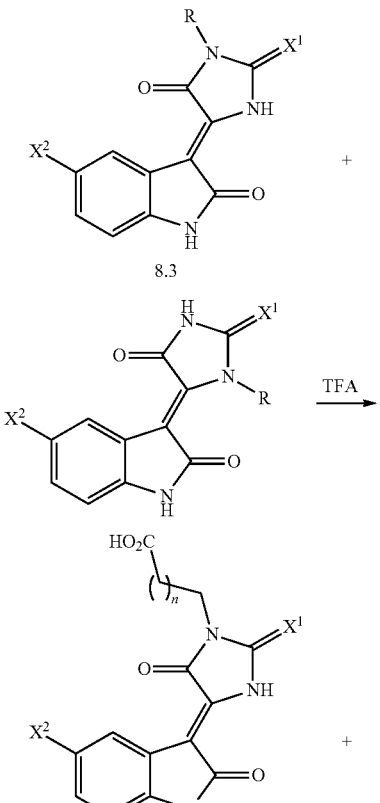
VIII
Synthetic Scheme 7: Compounds of Scaffold 6
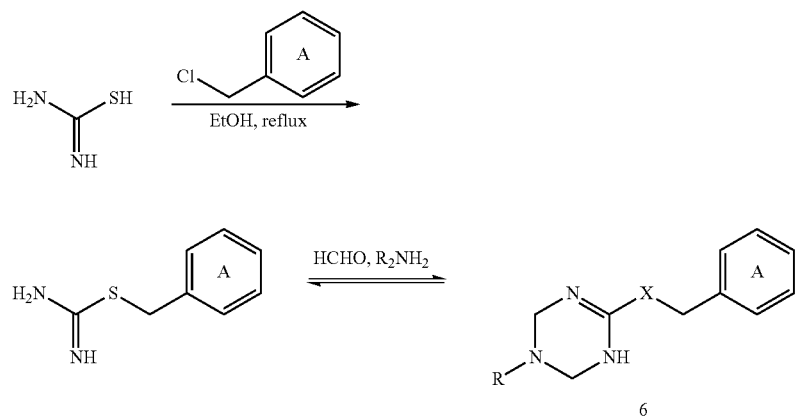

Synthetic Scheme 8: Compounds of Scaffold 7

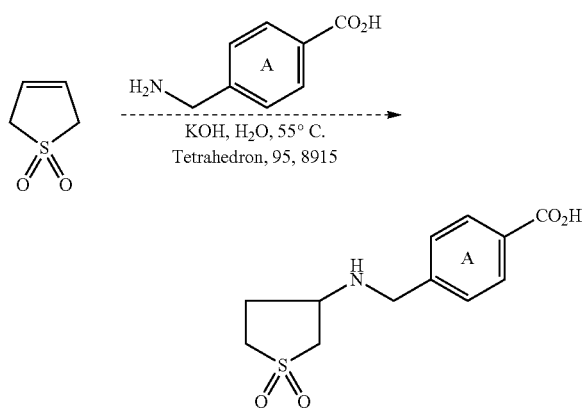

Synthetic Scheme 9: Compounds of Scaffold 8

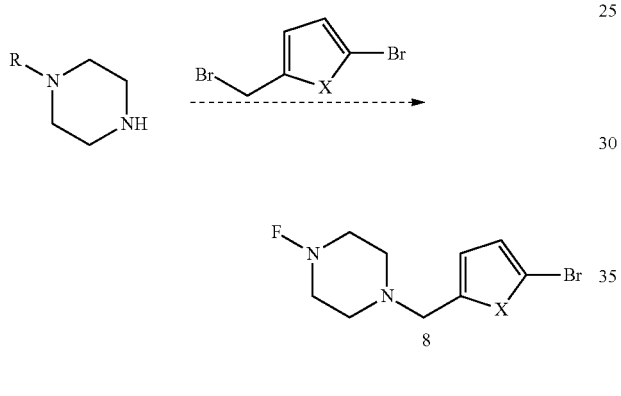

Synthetic Scheme 10: Compounds of Scaffold 9

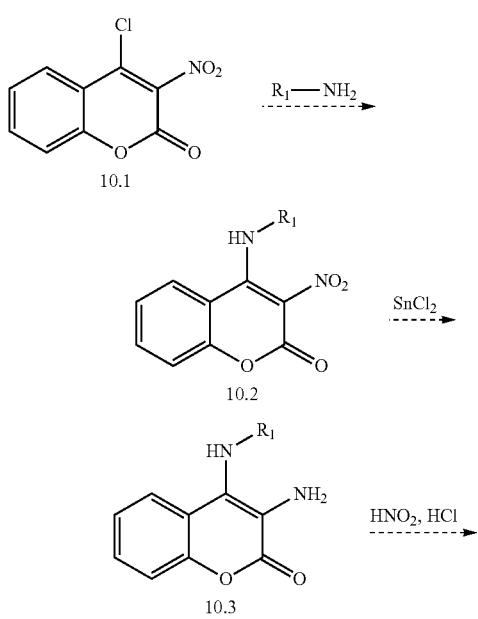

-continued

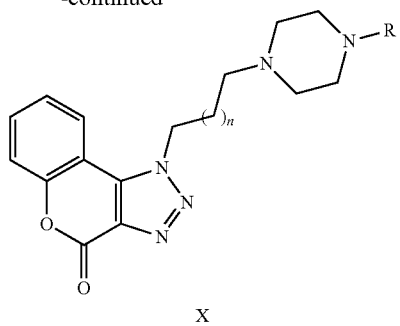

Synthetic Scheme 11: Compounds of Scaffold 11

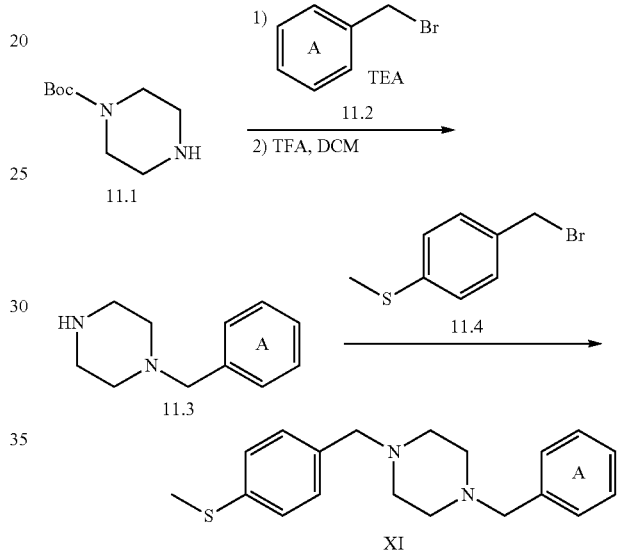

Synthetic Scheme 12: Compounds of Scaffold 12

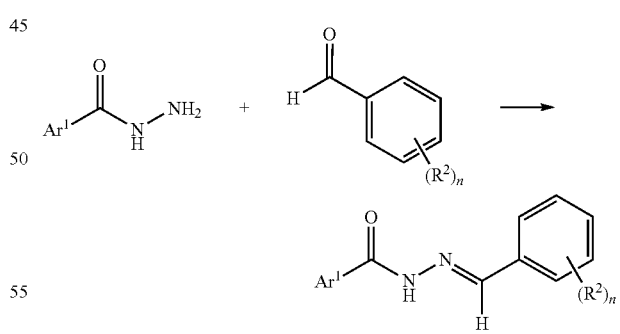

Cell Culture 293T cells were grown in Dulbecco's modified Eagles medium supplemented with 10% fetal bovine serum (FBS) (Gemini Bio-Products, Woodland, Calif.) and 1% penicillin-streptomycin. DLBCL cell lines OCI-Ly1, OCI-Ly1-B50, OCI-Ly7, OCI-Ly10 and OCI-Ly19 were grown in 80% Iscove's medium, 20% FBS and penicillin G/streptomycin. DLBCL cell lines Toledo, Farage, SU-DHL4, DOHH-2, SC-1, RCK8, TMD8, HBL-1, Ly3, Karpas 422 and SU- DHL6 were cultured in 90% RPMI medium, 10% FBS, 2 mM glutamine, 10 mM Hepes and penicillin G/streptomycin. All cell lines were cultured at 37° C. in a humidified atmosphere of 5% CO2.

MicroScale Thermophoresis Measurements:

Recombinant BCL6-BTB was labeled using the RED-NHS Labeling kit (NanoTemper Technologies). The labeling reaction was performed according to the manufacturer's instructions in the supplied labeling buffer applying a concentration of 20 μM protein (molar dye:protein ratio≈2:1) at RT for 30 min. Unreacted dye was removed with the supplied dye removal columns equilibrated with PBS buffer (PBS, 0.005% Tween-80). The label:protein ratio was determined using photometry at 650 nm and Bradford reagent. Thereby, a ratio of 0.8 was typically achieved. The labeled BCL6-BTB was adjusted to 400 nM with PBS (Thermo) buffer supplemented with 0.05% Tween-80 (Fisher scientific). SMRT, 79-6 and 1085 were dissolved in PBS buffer supplemented with 0.05% Tween-80 and 10% DMSO and a series of 16 1:1 dilutions were prepared in the identical buffer, producing ligand concentrations ranging from 19 pM to 625 μM. For thermophoresis, each ligand dilution was mixed with one volume of labeled BCL6-BTB, which leads to a final concentration of fluorescently labeled BCL6-BTB of 200 nM and final ligand concentrations ranging from 9 pM to 312 nM in a 5% DMSO final concentration. After 10 min incubation, approximately 4 μL of each solution was filled into Monolith NT Standard Treated Capillaries (NanoTemper Technologies GmbH). Thermophoresis was measured using a Monolith NT.115 instrument (NanoTemper Technologies GmbH) at an ambient temperature of 25° C. with 5 s/30 s/5 s laser off/on/off times, respectively. Instrument parameters were adjusted with 90% LED power and 40% MST power. Data of three independent experiments were analyzed (NT.Analysis software version 1.5.41, NanoTemper Technologies) using the signal from Thermophoresis.

Luciferase Reporter Assays

For screening of the synthesized small molecules we transfected 5×10$^5$ 293 T cells in a 6-well plate using polyethylenimine (PEI) with a luciferase reporter vector containing five binding sites for the yeast GAL4 DNA binding domain and a thymidine kinase (TK) promoter, (GAL4) 5TK-Luc (Polo et al., 2004) and an internal control TK-renilla reporter vector, pRL-TK (Promega) at a 10:1 ratio. Cells were also transfected with 250 ng of a plasmid expressing the GAL4 DNA binding domain (DBD) alone (pBXG1) or GAL4-DBD fused to the BCL6-BTB. Alternatively, cells were transfected with 1320 ng of plasmid containing the Kaiso-BTB domain fused to GAL4-DBD, 500 ng HIC-BTB-GAL4-DBD (Polo et al., 2004), 500 ng PLZF-BTB-GAL4-DBD (Polo et al., 2004), or 500-1320 ng GAL4-DBD alone. Twenty-four hours after transfection cells were harvested and redistributed to 96-well plates at a density of 20,000 cells per well, respectively, after which cells were treated in quadruplicate with 50 or 100 μM concentrations of different compounds or DMSO for 24 hr. Cell lysates were examined for the abundance of firefly luciferase relative to renilla luciferase (in counts per second) with the Dual-Luciferase Reporter Assay kit (Promega, Madison, Wis.) according to the manufacturer's protocol and a Synergy4 plate reader (BioTek Instruments, Winooski, Vt.). The repressor activity of each BTB domain was calculated as the relative fold change in repression compared with the GAL4 DBD plasmid control under the same treatment conditions.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of disrupting BCL6 BTB domain interactions with corepressors, in B-cells, comprising exposing the B cells to an effective concentration of a compound that blocks the lateral groove of BCL6; wherein the compound that blocks the lateral groove of BCL6 is a compound of formula (I)

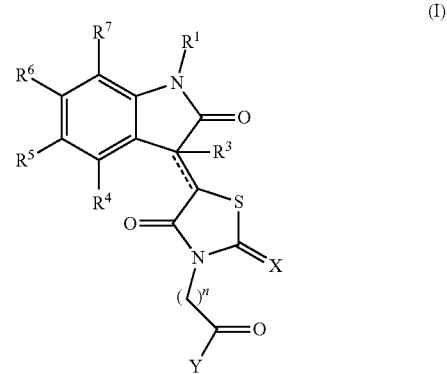

wherein a dashed line indicates that a double bond can be present or absent; when a double bond is present, R$^3$ is absent; R$^1$ is H, (C1-C6)alkyl, benzyl, 2-propenyl or 2-propynyl, or R$^1$ is a group of formula —CH$_2$CO$_2$R or —CH$_2$C(=O)OCH(R)—Ar$^1$, wherein R is H or (C1-C6)alkyl, Ar$^1$ is phenyl substituted with 0, 1, or 2 independently selected substituents from the group consisting of (C1-C6)alkyl, (C1-C6)alkoxy, halo, and (C1-C6)haloalkyl; n=2; R$^3$ is H or OH; R$^4$ and R$^6$ are H, R$^5$ is Cl, and R$^7$ is H or Cl; X is O or S; and Y is OH or O(C1-C6)alkyl; or a pharmaceutically acceptable salt thereof.

2. A method of inhibiting diffuse large B-cell lymphoma (DLBCL) tumor growth, or causing DLBCL tumor regression, or both, in a mammal, comprising administering to the mammal in need thereof an effective dose of a compound that blocks the BTB lateral groove of BCL6; wherein the compound that blocks the lateral groove of BCL6 is a compound of formula (I)

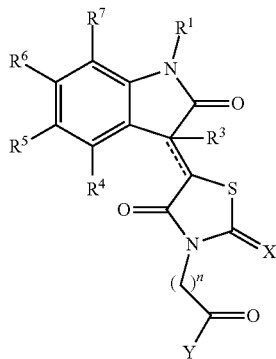

wherein a dashed line indicates that a double bond can be present or absent; when a double bond is present, $R^3$ is absent; $R^1$ is H, (C1-C6)alkyl, benzyl, 2-propenyl or 2-propynyl, or $R^1$ is a group of formula —CH$_2$CO$_2$R or —CH$_2$C(=O)OCH(R)—Ar$^1$, wherein R is H or (C1-C6)alkyl, Ar$^1$ is phenyl substituted with 0, 1, or 2 independently selected substituents from the group consisting of (C1-C6)alkyl, (C1-C6)alkoxy, halo, and (C1-C6)haloalkyl; n=2; $R^3$ is H or OH; $R^4$ and $R^6$ are H, $R^5$ is Cl, and $R^7$ is H or Cl; X is O or S; and Y is OH or O(C1-C6)alkyl; or a pharmaceutically acceptable salt thereof.

3. A method of inhibiting transcriptional repression induced by a complex of BCL6 with SMRT or other corepressor proteins in cancer cells, comprising exposing the cancer cells to an effective concentration of a compound that blocks the BTB lateral groove of BCL6; wherein the compound that blocks the lateral groove of BCL6 is a compound of formula (I)

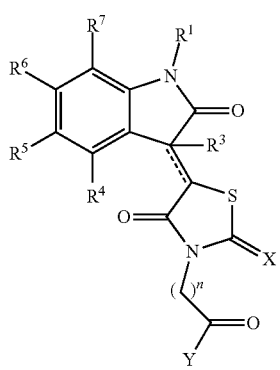

wherein a dashed line indicates that a double bond can be present or absent; when a double bond is present, $R^3$ is absent; $R^1$ is H, (C1-C6)alkyl, benzyl, 2-propenyl or 2-propynyl, or $R^1$ is a group of formula —CH$_2$CO$_2$R or —CH$_2$C(=O)OCH(R)—Ar$^1$, wherein R is H or (C1-C6)alkyl, Ar$^1$ is phenyl substituted with 0, 1, or 2 independently selected substituents from the group consisting of (C1-C6)alkyl, (C1-C6)alkoxy, halo, and (C1-C6)haloalkyl; n=2; $R^3$ is H or OH; $R^4$ and $R^6$ are H, $R^5$ is Cl, and $R^7$ is H or Cl; X is O or S; and Y is OH or O(C1-C6)alkyl; or a pharmaceutically acceptable salt thereof.

4. A method of alleviating the symptoms of cancer in a patient in need thereof, comprising administering to the patient an effective dose of a compound that blocks the BTB lateral groove of BCL6; wherein the compound that blocks the lateral groove of BCL6 is a compound of formula (I)

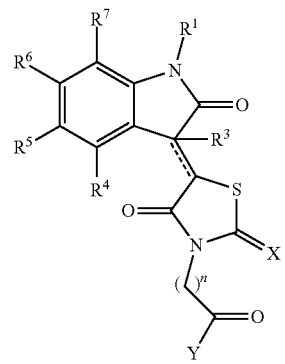

wherein a dashed line indicates that a double bond can be present or absent; when a double bond is present, $R^3$ is absent; $R^1$ is H, (C1-C6)alkyl, benzyl, 2-propenyl or 2-propynyl, or $R^1$ is a group of formula —CH$_2$CO$_2$R or —CH$_2$C(=O)OCH(R)—Ar$^1$, wherein R is H or (C1-C6)alkyl, Ar$^1$ is phenyl substituted with 0, 1, or 2 independently selected substituents from the group consisting of (C1-C6)alkyl, (C1-C6)alkoxy, halo, and (C1-C6)haloalkyl; n=2; $R^3$ is H or OH; $R^4$ and $R^6$ are H, $R^5$ is Cl, and $R^7$ is H or Cl; X is O or S; and Y is OH or O(C1-C6)alkyl; or a pharmaceutically acceptable salt thereof.

5. The method of any one of claims 1-4, wherein the compound of formula (I) is any one of

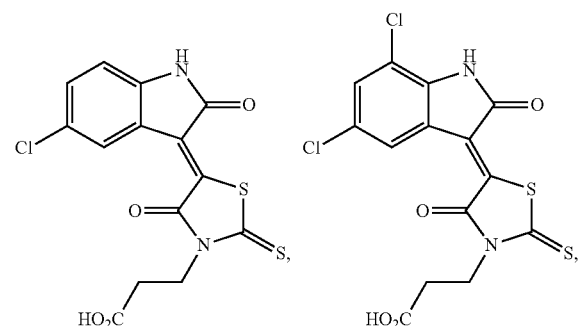

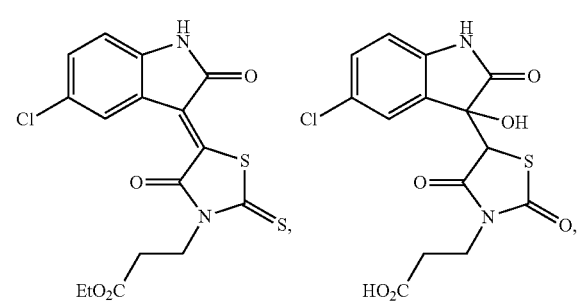 [SMILES: CCOC(=O)CCN1C(=O)/C(=C2/C(=O)Nc3ccc(Cl)cc32)SC1=S ; O=C(O)CCN1C(=O)SC(C2(O)C(=O)Nc3ccc(Cl)cc32)C1=O]

73
-continued
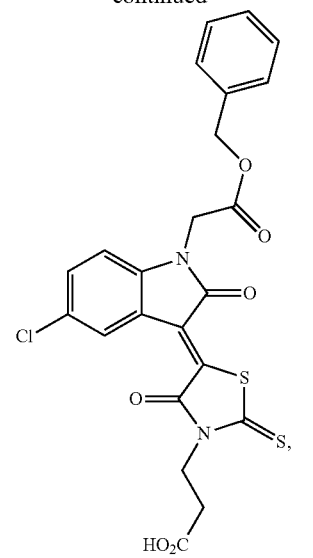
74
-continued
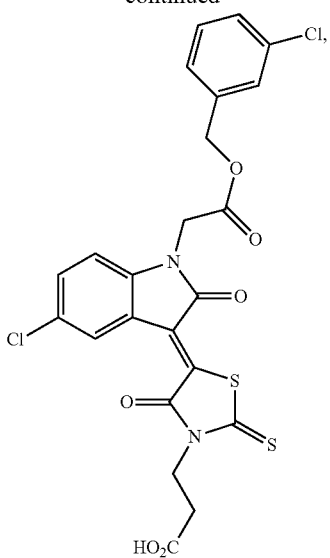
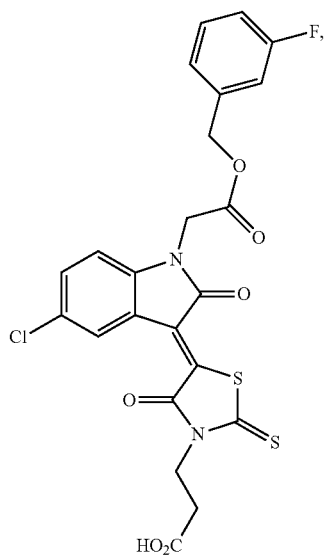

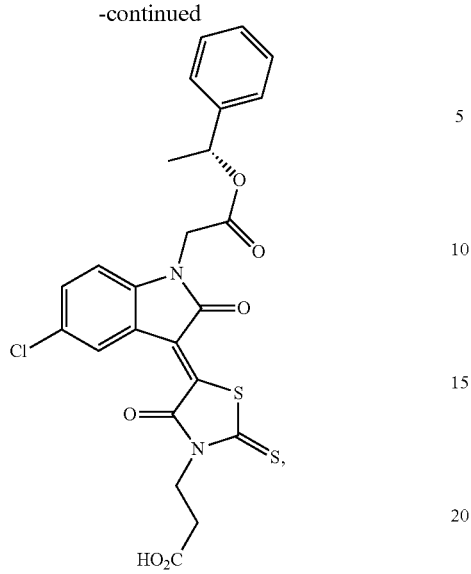

or a pharmaceutically acceptable salt thereof.

6. The method of claim 4, wherein in addition to administration of the compound that blocks the BTB lateral groove of BCL6, an effective amount of a second anticancer agent is administered to the patient.

7. The method of claim 6, wherein the second anticancer agent is doxorubicin, vincristine, dexamethasone, or mechloretamine, or comprises a combination of cyclophosphamide, doxorubicin, vincristine, and prednisone (CHOP).

* * * * *

UNITED STATES PATENT AND TRADEMARK OFFICE
CERTIFICATE OF CORRECTION

PATENT NO. : 9,943,506 B2
APPLICATION NO. : 14/899083
DATED : April 17, 2018
INVENTOR(S) : Melnick et al.

Page 1 of 2

It is certified that error appears in the above-identified patent and that said Letters Patent is hereby corrected as shown below:

On the Title Page

In item (57), in "Abstract", in Column 2, Line 8, delete "involvedoncogene" and insert --involved oncogene-- therefor In item (57), in "Abstract", in Column 2, Line 8, delete "B-celllymphomas" and insert --B-cell lymphomas-- therefor In the Claims In Column 70, Line 52, in Claim 1, delete "(C1-C6)alkyl," and insert --$(C_1-C_6)$alkyl,-- therefor In Column 70, Line 54, in Claim 1, delete "(C1-C6)alkyl," and insert --$(C_1-C_6)$alkyl,-- therefor In Column 70, Lines 56-57, in Claim 1, delete "(C1-C6)alkyl, (C1-C6)alkoxy," and insert --$(C_1-C_6)$alkyl, $(C_1-C_6)$alkoxy,-- therefor In Column 70, Line 57, in Claim 1, delete "(C1-C6)haloalkyl;" and insert --$(C_1-C_6)$haloalkyl;-- therefor In Column 70, Line 59, in Claim 1, delete "O(C1-C6)alkyl;" and insert --O$(C_1-C_6)$alkyl;-- therefor In Column 71, Line 20, in Claim 2, delete "(C1-C6)alkyl," and insert --$(C_1-C_6)$alkyl,-- therefor In Column 71, Line 22, in Claim 2, delete "(C1-C6)alkyl," and insert --$(C_1-C_6)$alkyl,-- therefor In Column 71, Lines 24-25, in Claim 2, delete "(C1-C6)alkyl, (C1-C6)alkoxy," and insert --$(C_1-C_6)$alkyl, $(C_1-C_6)$alkoxy,-- therefor Signed and Sealed this
Fourteenth Day of April, 2020

Andrei Iancu
*Director of the United States Patent and Trademark Office*

CERTIFICATE OF CORRECTION (continued)
U.S. Pat. No. 9,943,506 B2

In Column 71, Line 25, in Claim 2, delete "(C1-C6)haloalkyl;" and insert --$(C_1-C_6)$haloalkyl;-- therefor In Column 71, Line 27, in Claim 2, delete "O(C1-C6)alkyl;" and insert --O$(C_1-C_6)$alkyl;-- therefor In Column 71, Line 56, in Claim 3, delete "(C1-C6)alkyl," and insert --$(C_1-C_6)$alkyl,-- therefor In Column 71, Line 58, in Claim 3, delete "(C1-C6)alkyl," and insert --$(C_1-C_6)$alkyl,-- therefor In Column 71, Lines 60-61, in Claim 3, delete "(C1-C6)alkyl, (C1-C6)alkoxy," and insert --$(C_1-C_6)$alkyl, $(C_1-C_6)$alkoxy,-- therefor In Column 71, Line 61, in Claim 3, delete "(C1-C6)haloalkyl;" and insert --$(C_1-C_6)$haloalkyl;-- therefor In Column 71, Line 63, in Claim 3, delete "O(C1-C6)alkyl;" and insert --O$(C_1-C_6)$alkyl;-- therefor In Column 72, Line 24, in Claim 4, delete "(C1-C6)alkyl," and insert --$(C_1-C_6)$alkyl,-- therefor In Column 72, Line 26, in Claim 4, delete "(C1-C6)alkyl," and insert --$(C_1-C_6)$alkyl,-- therefor In Column 72, Lines 28-29, in Claim 4, delete "(C1-C6)alkyl, (C1-C6)alkoxy," and insert --$(C_1-C_6)$alkyl, $(C_1-C_6)$alkoxy,-- therefor In Column 72, Line 29, in Claim 4, delete "(C1-C6)haloalkyl;" and insert --$(C_1-C_6)$haloalkyl;-- therefor In Column 72, Line 31, in Claim 4, delete "O(C1-C6)alkyl;" and insert --O$(C_1-C_6)$alkyl;-- therefor